(12) United States Patent
Toste et al.

(10) Patent No.: US 9,856,427 B2
(45) Date of Patent: Jan. 2, 2018

(54) METHOD TO CONVERT FERMENTATION MIXTURE INTO FUELS

(75) Inventors: F. Dean Toste, Piedmont, CA (US);
Pazhamalai Anbarasan, Berkeley, CA (US); Joseph B. Binder, Naperville, IL (US); Paul A. Willems, Naperville, IL (US); Douglas S. Clark, Orinda, CA (US); Zach Baer, Berkeley, CA (US); Sanil Sreekumar, Thrissur (IN); Harvey W. Blanch, San Francisco, CA (US)

(73) Assignees: The Regents of the University of California, Oakland, CA (US); BP Corporation North America Inc., Houston, TX (US)

( * ) Notice: Subject to any disclaimer, the term of this patent is extended or adjusted under 35 U.S.C. 154(b) by 532 days.

(21) Appl. No.: 14/123,064

(22) PCT Filed: Apr. 26, 2012

(86) PCT No.: PCT/US2012/035306
§ 371 (c)(1),
(2), (4) Date: Feb. 6, 2014

(87) PCT Pub. No.: WO2012/166267
PCT Pub. Date: Dec. 6, 2012

(65) Prior Publication Data
US 2014/0137465 A1    May 22, 2014

Related U.S. Application Data

(60) Provisional application No. 61/491,141, filed on May 27, 2011.

(51) Int. Cl.
*C10L 1/02* (2006.01)
*C07C 45/71* (2006.01)
(Continued)

(52) U.S. Cl.
CPC ............... *C10L 1/02* (2013.01); *C07C 45/71* (2013.01); *C10L 1/026* (2013.01); *C12P 7/16* (2013.01);
(Continued)

(58) Field of Classification Search
CPC .......... C07C 45/71; C07C 49/04; C10L 1/02; C10L 1/026; C12P 7/26; C12P 7/28; C12P 7/16; Y02E 50/10
(Continued)

(56) References Cited

U.S. PATENT DOCUMENTS 2,434,631 A    1/1948 Winkler et al.
3,781,307 A  * 12/1973 Chabardes et al. ..... C07C 45/71
                                                              549/498
(Continued)

FOREIGN PATENT DOCUMENTS

CN    101440381 A    5/2009
CN    101787378 A    7/2010
(Continued)

OTHER PUBLICATIONS

International Search Report and Written Opinion received for PCT Patent Application No. PCT/US2012/035306, dated Feb. 13, 2013, 16 pages.
(Continued)

*Primary Examiner* — Latosha Hines
(74) *Attorney, Agent, or Firm* — Morrison & Foerster LLP

(57) ABSTRACT

The present disclosure provides methods to produce ketones suitable for use as fuels and lubricants by catalytic conversion of an acetone-butanol-ethanol (ABE) fermentation product mixture that can be derived from biomass.

14 Claims, 18 Drawing Sheets

(51) Int. Cl.
  *C12P 7/26* (2006.01)
  *C12P 7/28* (2006.01)
  *C12P 7/16* (2006.01)
(52) U.S. Cl.
  CPC .................. *C12P 7/26* (2013.01); *C12P 7/28* (2013.01); *Y02E 50/10* (2013.01)
(58) Field of Classification Search
  USPC .......................................................... 44/438
  See application file for complete search history.

(56) References Cited

U.S. PATENT DOCUMENTS

| | | | |
|---|---|---|---|
| 4,250,259 A * | 2/1981 | Hou | ........................ C12N 1/30 435/148 |
| 8,075,642 B2 | 12/2011 | Dumesic et al. | |
| 2005/0089979 A1 | 4/2005 | Ezeji et al. | |
| 2007/0275447 A1 | 11/2007 | Lewis et al. | |
| 2008/0015395 A1 | 1/2008 | D'Amore et al. | |
| 2008/0015397 A1 | 1/2008 | D'Amore et al. | |
| 2008/0103337 A1 | 5/2008 | D'Amore et al. | |
| 2008/0132730 A1 | 6/2008 | Manzer et al. | |
| 2008/0244961 A1 | 10/2008 | Rusek et al. | |
| 2008/0248540 A1* | 10/2008 | Yang | ........................ C12P 7/16 435/160 |
| 2009/0030239 A1 | 1/2009 | D'Amore et al. | |
| 2009/0036716 A1 | 2/2009 | D'Amore et al. | |
| 2010/0076233 A1 | 3/2010 | Cortright et al. | |
| 2010/0077655 A1 | 4/2010 | Bauldreay et al. | |
| 2010/0204526 A1 | 8/2010 | Kouba et al. | |
| 2010/0263265 A1 | 10/2010 | Delfort et al. | |
| 2010/0268005 A1 | 10/2010 | Rusek et al. | |
| 2010/0330633 A1 | 12/2010 | Walther et al. | |
| 2011/0172475 A1 | 7/2011 | Peters et al. | |
| 2011/0237833 A1 | 9/2011 | Koltermann et al. | |
| 2011/0306801 A1 | 12/2011 | Schucker et al. | |

FOREIGN PATENT DOCUMENTS

| | | | |
|---|---|---|---|
| DE | 2257675 | 5/1974 | |
| DE | 2257675 A1 * | 5/1974 | ............. C07C 45/71 |
| EP | 0719751 A1 | 7/1996 | |
| EP | 828558 B1 | 12/2001 | |
| GB | 400384 A | 10/1933 | |
| GB | 723280 | 2/1955 | |
| WO | 1998/051813 A1 | 11/1998 | |
| WO | WO 9851813 A1 * | 11/1998 | ................ C12P 7/06 |
| WO | 2007/149397 A2 | 12/2007 | |
| WO | 2008/066579 A1 | 6/2008 | |
| WO | 2008/066581 A1 | 6/2008 | |
| WO | 2008/109877 A1 | 9/2008 | |
| WO | 2008/111941 A2 | 9/2008 | |
| WO | 2008/156320 A1 | 12/2008 | |
| WO | 2009/152495 A2 | 12/2009 | |
| WO | 2010/098694 A2 | 9/2010 | |
| WO | 2011/077242 A1 | 6/2011 | |
| WO | 2011/143392 A1 | 11/2011 | |
| WO | 2012/001416 A1 | 1/2012 | |
| WO | 2012/001417 A1 | 1/2012 | |
| WO | 2012/166267 A2 | 12/2012 | |
| WO | 2012/166267 A3 | 4/2013 | |

OTHER PUBLICATIONS

International Preliminary Report on Patentability received for PCT Patent Application No. PCT/US2012/035306, dated Dec. 12, 2013, 11 pages.
Das et al., "Influence of the Metal Function in the "One-Pot" Synthesis of 4-Methyl-2-Pentanone (Methyl Isobutyl Ketone) from Acetone over Palladium Supported on Mg(Al)O Mixed Oxides Catalysts", Catalysis Letters, vol. 71, No. 3-4, 2001, pp. 181-185.
Demirbas, A., "The Importance of Bioethanol and Biodiesel from Biomass", Energy Sources, Part B, vol. 3, 2008, pp. 177-185.
He et al., "One-Step Synthesis of 2-Pentanone from Ethanol over K-Pd/MnOx—ZrO2—ZnO Catalyst", Journal of Molecular Catalysis A: Chemical, vol. 226, 2005, pp. 89-92.
International Search Report and Written Opinion received for PCT Patent Application No. PCT/US2014/035545, dated Nov. 24, 2014, 18 pages.
Alonso et al., "The α-Alkylation of Methyl Ketones with Primary Alcohols Promoted by Nickel Nanoparticles under Mild and Ligandless Conditions", Synlett, No. 12, Georg Thieme Verlag Stuttgart, 2007, pp. 1877-1880.
Debecker et al., "Exploring, Tuning, and Exploiting the Basicity of Hydrotalcites for Applications in Heterogeneous Catalysis", Chemistry A European Journal, vol. 15, 2009, pp. 3920-3935.
Hamid et al., "Borrowing Hydrogen in the Activation of Alcohols", Advanced Synthesis & Catalysis, vol. 349, No. 10, Jul. 2, 2007, pp. 1555-1575.
Kim et al., "Recyclable Gold Nanoparticle Catalyst for the Aerobic Alcohol Oxidation and C—C Bond Forming Reaction between Primary Alcohols and ketones Under Ambient Conditions", Tetrahedron, vol. 65, No. 7, Feb. 14, 2009, pp. 1461-1466.
Kwon et al., "Recyclable Palladium Catalyst for Highly Selective α Alkylation of Ketones with Alcohols", Angewandte Chemie, vol. 44, 2005, pp. 6913-6915.
Roffler et al., "Design and Mathematical Description of Differential Contactors Used in Extractive Fermentations", Biotechnology and Bioengineering, vol. 32, 1988, pp. 192-204.
Roffler et al., "In Situ Extractive Fermentation of Acetone and Butanol", Biotechnology and Bioengineering, vol. 31, 1988, pp. 135-143.
Roffler et al., "In-Situ Recovery of Butanol During Fermentation", Part 1, Bioprocess Engineering, vol. 2, No. 1, Mar. 1987, pp. 1-12.
Roffler et al., "In-Situ Recovery of Butanol During Fermentation", Part 2, Bioprocess Engineering, vol. 2, No. 4, Dec. 1987, pp. 181-190.
Shimizu et al., "Direct C—C Cross-Coupling of Secondary and Primary Alcohols Catalyzed by a γ-Alumina-Supported Silver Subnanocluster", Angewandte Chemie International Edition, vol. 48, 2009, pp. 3982-3986.
Yamada et al., "A Solid-Phase Self-Organized Catalyst of Nanopalladium with Main-Chain Viologen Polymers: α-Alkylation of Ketones with Primary Alcohols", Organic Letters, vol. 8, No. 7, Mar. 2006, pp. 1375-1378.
Yamada et al., "Development of a Convoluted Polymeric Nanopalladium Catalyst: α-alkylation of Ketones and Ring-Opening Alkylation of Cyclic 1,3-Diketones with Primary Alcohols", Tetrahedron, vol. 63, No. 35, Aug. 27, 2007, pp. 8492-8498.
Ekeley et al., "The Condensation Products of Diethyl Ketone", Journal of the American Chemical Society, vol. 46, Feb. 1924, pp. 446-450, 5 pages.
International Preliminary Report on Patentability received for PCT Application No. PCT/US2015/022086, dated Oct. 6, 2016, 9 pages.
International Search Report and Written Opinion received for PCT Patent Application No. PCT/US2015/022086, dated Sep. 29, 2015, 14 pages.
Requirement for Restriction/Election received for U.S. Appl. No. 14/786,153, dated Aug. 30, 2016, 10 pages.
Seebald et al., "Reaktionen an Aluminiumoxiden. 2. Mitt.: Umsetzungen Von Butan-2-on an Aluminiumoxid", Arch. Pharmaz., vol. 305, No. 10, 1972, 18 pages (9 pages of English Translation and 9 pages of Original Copy).
Shuikin et al., "Activity of Copper- and Iron-Containing Catalysts in the Reaction of Isophorone with Ammonia and Hydrogen", Petroleum Chemistry, vol. 36, No. 2, 1996, pp. 174-179.
Non Final Office Action received for U.S. Appl. No. 14/786,153, dated Feb. 17, 2017, 10 pages.
Shimizu et al. "Direct C—C Cross-Coupling of Secondary and Primary Alcohols Catalyzed by a γ-Alumina-Supported Silver Subnanocluster", Angew. Chem., vol. 121, 2009, pp. 4042-4046.

* cited by examiner

METHOD TO CONVERT FERMENTATION MIXTURE INTO FUELS

CROSS-REFERENCE TO RELATED APPLICATIONS

This is a U.S. National Phase patent application of PCT/US2012/035306, filed Apr. 26, 2012, which claims priority to U.S. Provisional Patent Application No. 61/491,141 filed May 27, 2011, each of which is incorporated herein by reference in its entirety.

FIELD

The present disclosure generally relates to the production of fuels from biomass. More specifically, the present disclosure relates to the catalytic conversion of the products arising from the fermentation of biomass-derived saccharides, such as an acetone-butanol-ethanol (ABE) fermentation product mixture, into ketones suitable for use as fuels.

BACKGROUND

Producing fuels from renewable sources has become increasingly important as a means of reducing the production of greenhouse gases and of reducing the imports of petroleum. See L. D. Gomez, C. G. Steele-King, S. J. McQueen-Mason, New Phytologist, 178, 473-485, (2008). Lignocellulosic biomass is typically made up of cellulose, hemicellulose, and lignin. These biomass components are non-edible, carbohydrate-rich polymers that may serve as a renewable source of energy. They typically make up to approximately 75% of the dry weight of biomass. As such, conversion of these non-edible biomass components into bio-fuels is of ongoing interest that can benefit the environment and reduce petroleum imports. See A. Demirbas, Energy Sources, Part B: Economics, Planning and Policy, 3(2) 177-185 (2008).

Currently, several approaches are available for converting biomass into fuels. For example, chemical processing routes may involve high temperature pyrolysis or biomass liquefaction; pyrolysis products (syngas) can be converted via Fischer-Tropsch chemistry to higher carbon number fuels. Biological routes typically first hydrolyze the polysaccharide content of biomass to monosaccharides using cellulase enzymes. These monosaccharides are then microbially converted to fuels.

Early efforts to biologically produce fuels from biomass included the fermentation of both starch-derived and lignocellulosic-derived carbohydrates to bio-alcohols such as bio-ethanol and bio-butanol. See Blanch, H. W. and C. R. Wilke, Sugars and Chemicals from Cellulose, Reviews in Chemical Engineering, eds., N. E. Amundson and D. Luss, vol 1, 1 (1982). These natural biological routes to produce alcohols (e.g., ethanol and butanol) from carbohydrates typically yield low molecular weight compounds that are generally more suitable as gasoline additives than as jet and diesel fuel compounds. While advances in metabolic engineering have enabled biological production of several higher molecular weight jet and diesel fuel compounds, these processes typically suffer from low titers and yields.

More recent efforts have focused on the carbohydrate source obtained from lignocellulosic biomass. Cellulose and hemicellulose obtained from lignocellulosic biomass after pre-treatment and hydrolysis affords hexoses and pentoses, respectively. Subsequent dehydration of these sugars into furfural and 5-hydroxymethylfurfural (HMF) may be achieved by chemical processes. Biological routes can ferment the hexoses and pentoses to short chain alcohols (e.g., ethanol and butanols) or to higher carbon number alkanes and alkenes, terpenes and fatty acids that can be esterified for use as diesel fuels.

While there are efficiencies of hexose and pentose conversion to short-chain alcohols, current microbial routes to higher carbon number products often have low yields and product titers. These products are currently not economically attractive as fungible fuels that can be employed as gasoline, jet and diesel fuel additives or replacements.

Thus, what is needed in the art is a commercially-viable process of producing fungible fuels, such as transportation fuels, and other chemicals from biomass, which allows for the control of product selectively. Moreover, what is needed in the art is a commercially-viable process for producing higher molecular weight fuel compounds and other chemicals from a saccharide-derived from biomass, such as an acetone-butanol-ethanol (ABE) mixture.

BRIEF SUMMARY

The present disclosure addresses this need by providing a process that converts a fermentation product mixture, such as an ABE fermentation mixture, obtained from biomass-derived carbohydrates into ketones suitable for use as fuels (e.g., transportation fuels) and lubricants.

In certain embodiments, when an ABE fermentation mixture is provided, acetone harbors a nucleophilic α-carbon that is amenable to C—C bond formation with electrophilic alcohols, such as ethanol and butanol. Using the reaction conditions described herein, higher molecular weight hydrocarbons suitable for use as jet and diesel fuels can be produced from the ABE fermentation mixture. Thus, the methods provided herein can integrate biological and chemocatalytic routes to convert ABE fermentation products into ketones of varying lengths by a palladium-catalyzed alkylation. Further, the methods provided herein allow for selectively producing in high yields gasoline, jet and diesel fuel compounds from biomass, such as lignocellulosic and cane sugars.

One aspect of the present disclosure provides a method A of producing one or more compounds of Formula I,

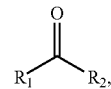

(Formula I)

in which each $R_1$ and $R_2$ is independently an optionally substituted alkyl, alkenyl, alkynyl, cycloalkyl, heterocycloalkyl, aryl, heteroaryl, or arylalkyl; in which the method includes: a) providing a fermentation product mixture that includes acetone and one or more optionally substituted alcohols; b) combining the fermentation product mixture with a metal-based catalyst in the presence of a base; and c) producing one or more compounds of Formula I, wherein at least one of the one or more compounds of Formula I is a double-alkylated compound.

In one embodiment of method A, each $R_1$ and $R_2$ may independently be an optionally substituted alkyl, cycloalkyl, heterocycloalkyl, aryl, heteroaryl, or arylalkyl. In another embodiment, each $R_1$ and $R_2$ may independently be an optionally substituted alkyl, alkenyl, or alkynyl. In another embodiment, each $R_1$ and $R_2$ is independently an optionally substituted alkyl. In another embodiment, each $R_1$ and $R_2$ is independently an optionally substituted C1-C30 alkyl. In another embodiment, each $R_1$ and $R_2$ is independently an optionally substituted C1-C20 alkyl. In another embodiment, each $R_1$ and $R_2$ is independently an optionally substituted C1-C15 alkyl. In yet another embodiment, each $R_1$ and $R_2$ is independently an optionally substituted C1-C9 alkyl. In yet another embodiment, each $R_1$ and $R_2$ is independently an optionally substituted C1-C8 alkyl. In yet another embodiment, each $R_1$ and $R_2$ is independently an optionally substituted C1-C5 alkyl.

In certain embodiments of method A, each $R_1$ and $R_2$ is independently an unsubstituted C1-C9 alkyl. In certain embodiments, each $R_1$ and $R_2$ is independently methyl, ethyl, propyl, isopropyl, butyl, pentyl, hexyl, heptyl, octyl or nonyl. In other embodiments, the C1-C9 alkyl may be unbranched or branched. In yet another embodiment, each $R_1$ and $R_2$ is independently an unsubstituted C1-C5 alkyl. In some embodiments, each $R_1$ and $R_2$ is independently methyl, ethyl, propyl, isopropyl, butyl, or pentyl. In certain embodiments, each $R_1$ and $R_2$ is independently methyl, propyl, isopropyl, or pentyl. In other embodiments, the unsubstituted C1-C5 alkyl may be unbranched or branched. In some embodiments, $R_1$ and $R_2$ may be the same or different.

In some embodiments of method A, the providing of the fermentation product mixture includes: providing a saccharide; and contacting the saccharide with a fermentation host to produce the fermentation product mixture. In some embodiments, the saccharide may include C5 saccharides, C6 saccharides, or a mixture thereof. In certain embodiments, the saccharide may include glucose, sucrose, cellobiose, and xylose, or a combination thereof. In certain embodiments, the saccharides may be derived from biomass. The biomass may include cellulose, hemicellulose, and/or lignin. In certain embodiments, the providing of the fermentation product mixture further includes contacting the saccharide and the fermentation host with an extractant. In some embodiments, the extractant has one or more of the following properties: i) is non-toxic to fermentation host (e.g., *Clostridium*); ii) has partition coefficients for acetone and butanol equal to or greater than 1; and iii) has a partition coefficient for ethanol of less than 0.5. In other embodiments, the extractant is selected from glyceryl tributyrate, glyceryl tripropionate, oleyl alcohol, and polypropylene glycol, or a combination thereof. In yet other embodiments, the fermentation product mixture has less than about 5 wt %, about 4 wt %, about 3 wt %, about 2 wt %, or about 1 wt % water.

In some embodiments of method A, each of the one or more optionally substituted alcohols is independently a primary alcohol or a secondary alcohol. In yet another embodiment, each of the one or more optionally substituted alcohols is independently a C1-C20 primary alcohol or a C1-C20 secondary alcohol. In yet another embodiment, each of the one or more optionally substituted alcohols is independently a C1-C15 primary alcohol or a C1-C15 secondary alcohol. In yet another embodiment, each of the one or more optionally substituted alcohols is independently a C1-C8 primary alcohol or a C1-C8 secondary alcohol. In yet another embodiment, each of the one or more optionally substituted alcohols is independently a C1-C5 primary alcohol or a C1-C5 secondary alcohol. In some embodiments, the one or more optionally substituted alcohols are two unsubstituted primary alcohols, two unsubstituted secondary alcohols, or one unsubstituted primary alcohol and one substituted secondary alcohol.

In some embodiments of method A, the fermentation product mixture is made up of acetone and one optionally substituted alcohol. In other embodiments of method A, the fermentation product mixture is made up of acetone and two optionally substituted alcohols. In yet other embodiments of method A, the fermentation product mixture is made up of acetone and two or more optionally substituted alcohols. In certain embodiments, the optionally substituted alcohols are C1-C20 primary alcohols. In other embodiments, the fermentation product mixture is made up of acetone and two or more optionally substituted C1-C15 primary alcohols. In other embodiments, the fermentation product mixture is made up of acetone and two or more optionally substituted C1-C8 primary alcohols. In yet other embodiments, the fermentation product mixture is made up of acetone and two or more optionally substituted C1-C4 primary alcohols. In yet other embodiments, the fermentation product mixture is made up of acetone, a first C1-C4 primary alcohol, and a second C1-C4 primary alcohol. In other embodiments, the fermentation product mixture is made up of acetone, butanol, and ethanol.

In certain embodiments of method A, the acetone, the first C1-C4 primary alcohol, and the second C1-C4 primary alcohol are present in the fermentation product mixture in a weight ratio of about 2-4 acetone to about 5-7 first primary alcohol to about 0.01-2 second primary alcohol. In some embodiments, the acetone, butanol, and ethanol are present in the fermentation product mixture in a weight ratio of about 2-4 acetone to about 5-7 butanol to about 0.01-2 ethanol. In other embodiments, the acetone, butanol, and ethanol are present in the fermentation product mixture in a weight ratio of about 3 to about 6 to about 0.01-1. In yet other embodiments, the acetone, butanol, and ethanol are present in the fermentation product mixture in a weight ratio of about 3 to about 6 to about 1.

In yet other embodiments of method A, the fermentation product mixture is made up of acetone, a C1-C4 primary alcohol, and a C1-C6 secondary alcohol. In other embodiments, the fermentation product mixture is made up of acetone, butanol, and hexanol. In one embodiment, the fermentation product mixture is made up of acetone, unbranched butanol, and branched hexanol (e.g., 2-methylhexan-1-ol, 2-ethylhexan-1-ol).

In certain embodiments of method A in which the fermentation product mixture is made up of acetone, butanol, and ethanol, the amount of base to butanol and ethanol is between 0.3 to 1.5 mole equivalents. In other embodiments, the amount of base to butanol and ethanol is between 0.32 to 1.3 mole equivalents. In yet other embodiments, the amount of base to butanol and ethanol is between 0.95 to 1.3 mole equivalents.

In some embodiments that may be combined with any of the preceding embodiments of method A, the metal-based catalyst may include nickel, ruthenium, rhodium, palladium, rhenium, iridium, platinum, or copper, or a combination of these metals. In certain embodiments, the metal-based catalyst may be [Ir(COD)Cl]$_2$, RuCl$_2$(COD), PtCl$_2$(COD), [Rh(COD)Cl]$_2$, Ni/Si-Alumina, Ru/C, Rh/C, Pt/C, or Pd/C, or a combination of these metal-based catalysts. In yet other embodiments, the metal-based catalyst may include a palladium-based catalyst, such as Pd(OAc)$_2$, Pd$_2$(dba)$_3$, Pd(OH)$_2$/C, Pd/C, Pd/CaCO$_3$, Pd/Alumina, or Pd-polyethylenimines on silica, or a combinations of these palladium-based catalysts.

In some embodiments that may be combined with any of the preceding embodiments of method A, the base may be K₃PO₄, KOH, Ba(OH)₂·8H₂O, K₂CO₃, KOAc, KH₂PO₄, Na₂HPO₄, pyridine, or Et₃N, or a combination of these bases.

In other embodiments that may be combined with any of the preceding embodiments of method A, the method further includes combining the fermentation product mixture in step (b) with a solvent. In some embodiments, the solvent is an organic solvent. In certain embodiments, the solvent may be toluene, ethyl acetate, diethylene glycol dimethyl ether, monoglyme, butanol, diethylene glycol dibutyl ether, oleyl alcohol, dibutyl phthalate, or mixtures of these solvents. In yet other embodiments, method A is performed neat.

In some embodiments that may be combined with any of the preceding embodiments of method A, the method further includes heating the reaction mixture of step (b) to a temperature sufficient to form the one or more compounds of Formula I. In certain embodiments, the temperature is between 100° C. to 200° C. In other embodiments, the temperature is between 110° C. to 180° C. In yet other embodiments, the temperature is between 110° C. to 145° C. In yet other embodiments, the temperature is between 140° C. to 220° C.

In some embodiments that may be combined with any of the preceding embodiments of method A, the one or more compounds of Formula I may include pentanone, heptanone, nonanone, and undecanone. In certain embodiments, the one or more compounds of Formula I may include unbranched or branched pentanone, unbranched or branched heptanone, unbranched or branched nonanone, unbranched or branched undecanone, unbranched or branched tridecanone, and/or unbranched or branched pentadecanone.

In some embodiments, the one or more compounds of Formula I may include 2-pentanone, 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and/or 5-butyl-7-ethylundecan-6-one. In certain embodiments, the one or more compounds of Formula I may include 2-pentanone, 4-heptanone, 2-heptanone, 4-nonanone, 2-methyl-4-nonanone, and 6-undecanone. In yet other embodiments, the one or more compounds of Formula I may include 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and 5-butyl-7-ethylundecan-6-one.

In certain embodiments, the one or more compounds of Formula I is a mixture of compounds selected from 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and/or 5-butyl-7-ethylundecan-6-one.

In some embodiments that may be combined with any of the preceding embodiments of method A, the yield of the one or more compounds of Formula I relative to the amount of acetone present in the fermentation product mixture is at least 35%, at least 40%, at least 50%, at least 60%, at least 75%, at least 80%, at least 85%, at least 90%, at least 95%, or at least 99%. In other embodiments, the yield of the one or more compounds of Formula I relative to the amount of acetone present in the fermentation product mixture is between about 35-95%, between about 50-95%, between about 60-90%, or between about 70-85%.

In some embodiments of method A, the method produces two or more compounds of Formula I, in which at least two of the two or more compounds of Formula I are double-alkylated compounds. In some embodiments, the yield of the two or more compounds of Formula I relative to the amount of acetone present in the fermentation mixture is at least 10%, at least 15%, at least 20%, at least 30%, at least 40%, at least 50%, at least 60%, at least 70%, at least 75%, at least 80%, at least 85%, or at least 90%. In some embodiments, the yield of the double-alkylated compounds of Formula I relative to the amount of acetone present in the fermentation product mixture is at least 10%, at least 15%, at least 20%, at least 30%, at least 40%, at least 50%, at least 60%, at least 70%, at least 75%, at least 80%, at least 85%, or at least 90%. In other embodiments, the yield of the double-alkylated compounds of Formula I relative to the amount of acetone present in the fermentation product mixture is between about 10-90%, between about 10-85%, between about 15-70%, or between about 15-65%.

In other embodiments that may be combined with any of the preceding embodiments of method A, the one or more products of Formula I may serve as one or more precursors for fuel additives. In yet other embodiments that may be combined with any of the preceding embodiments, the one or more products of Formula I may serve as one or more precursors for fuel. In yet other embodiments that may be combined with any of the preceding embodiments, the one or more products of Formula I may serve as one or more precursors for lubricants.

In yet other embodiments that may be combined with any of the preceding embodiments of method A, the method further includes adding one or more compounds to the fermentation product mixture, in which the one or more compounds may be a ketone or an alcohol. In certain embodiments, the one or more compounds added to the fermentation product mixture may include $R^aC(=O)R^b$, $(R^c)H_2COH$, $(R^d)_2HCOH$, or $(R^e)_3COH$, in which $R^a$, $R^b$, $R^c$, $R^d$ and $R^e$ at each occurrence may be independently an optionally substituted alkyl, alkenyl, alkynyl, cycloalkyl, heterocycloalkyl, aryl, heteroaryl, or arylalkyl. In some embodiments, $R^a$, $R^b$, $R^c$, $R^d$ and $R^e$ at each occurrence may be independently an optionally substituted C1-C20 alkyl, C1-C20 alkenyl, or C1-C20 alkynyl. In some embodiments, $R^a$, $R^b$, $R^c$, $R^d$ and $R^e$ at each occurrence may be independently an optionally substituted C1-C15 alkyl. In one embodiment, at least one of $R^a$, $R^b$, $R^c$, $R^d$ and $R^e$ is methyl. In some embodiments, the one or more compounds added to the fermentation product mixture are obtained from a biological process or a renewable source. In some embodiments, the one or more compounds are added to the fermentation product mixture before combination with the metal-based catalyst and the base.

In another embodiment that may be combined with any of the preceding embodiments of method A, the method further includes hydrogenating, deformylating, isomerizing, hydrodeoxygenating, or catalytic reforming the one or more compounds of Formula I produced by the methods described herein. In one embodiment, the hydrogenating, deformylating, isomerizing, hydrodeoxygenating, or catalytic reforming of the one or more compounds of Formula I involves a one-pot, multi-step process. In other embodiments of method A, the method further includes combining the one or more compounds of Formula I with a second metal-based catalyst. In some embodiments, the second metal-based catalyst includes a metal selected from the group consisting of platinum, nickel, molybdenum, tungsten, cobalt, and combinations of these metals. In certain embodiments, the second metal-based catalyst includes platinum, nickel-molybdenum (Ni—Mo), nickel-tungsten (Ni—W), cobalt-molybdenum (Co—Mo), and combinations of these metals. In specific embodiments, the second metal-based catalyst may be Pd/C, NiO—MoO$_3$/Al$_2$O$_3$, Pt/SiO$_2$—Al$_2$O$_3$, or combinations of these catalysts. In other embodiments, the combining of the one or more compounds of Formula I with the second metal-based catalyst converts the one or more compounds of Formula I into one or more alcohols. In yet other embodiments, the combining of the one or more compounds of Formula I with the second metal-based catalyst converts the one or more compounds of Formula I into one or more alkanes.

In some embodiments of method A, a fuel is produced following the hydrogenating, deformylating, isomerizing, hydrodeoxygenating, or catalytic reforming steps. In some embodiments of method A, a lubricant is produced following the hydrogenating, deformylating, isomerizing, hydrodeoxygenating, or catalytic reforming steps.

Another aspect of the present disclosure provides the use of the one or more compounds of Formula I produced by method A for the manufacture of a fuel or a lubricant.

Another aspect of the present disclosure provides a composition A that includes:
  a fermentation product mixture that includes acetone and one or more optionally substituted alcohols;
  a metal-based catalyst; and
  a base.

In certain embodiments of composition A, each of the one or more optionally substituted alcohols in the fermentation product mixture is independently a C1-C20 primary alcohol or a C1-C20 secondary alcohol. In yet another embodiment, each of the one or more optionally substituted alcohols is independently a C1-C15 primary alcohol or a C1-C15 secondary alcohol. In yet another embodiment, each of the one or more optionally substituted alcohols is independently a C1-C8 primary alcohol or a C1-C8 secondary alcohol. In yet another embodiment, each of the one or more optionally substituted alcohols is independently a C1-C5 primary alcohol or a C1-C5 secondary alcohol. In some embodiments, the one or more optionally substituted alcohols are two unsubstituted primary alcohols, two unsubstituted secondary alcohols, or one unsubstituted primary alcohol and one unsubstituted secondary alcohol.

In some embodiments of composition A, the fermentation product mixture is made up of acetone and one optionally substituted alcohol. In other embodiments of composition A, the fermentation product mixture is made up of acetone and two optionally substituted alcohols. In yet other embodiments of composition A, the fermentation product mixture is made up of acetone and two or more optionally substituted alcohols. In certain embodiments, the optionally substitute alcohols are C1-C20 primary alcohols. In other embodiments, the fermentation product mixture is made up of acetone and two or more optionally substituted C1-C15 primary alcohols. In other embodiments, the fermentation product mixture is made up of acetone and two or more optionally substituted C1-C8 primary alcohols. In yet other embodiments, the fermentation product mixture is made up of acetone and two or more optionally substituted C1-C5 primary alcohols. In yet other embodiments, the fermentation product mixture is made up of acetone, a first C1-C5 primary alcohol, and a second C1-C5 primary alcohol. In some embodiments, the fermentation product mixture is made up acetone, a first optionally substituted primary alcohol, and a second optionally substituted primary alcohol. In some embodiments, the fermentation product mixture is made up of acetone, a first optionally substituted C1-C4 primary alcohol, and a second optionally substituted C1-C4 primary alcohol. In other embodiments, the fermentation product mixture is made up of acetone, butanol, and ethanol.

In certain embodiments of composition A, the acetone, the first optionally substituted primary alcohol, and the second optionally substituted primary alcohol are present in the fermentation product mixture in a weight ratio of about 2-4 acetone to about 5-7 first optionally substituted primary alcohol to about 0.01-2 second optionally substituted primary alcohol. In some embodiments, the acetone, butanol, and ethanol are present in the fermentation product mixture in a weight ratio of about 2-4 acetone to about 5-7 butanol to about 0.01-2 ethanol. In other embodiments, the acetone, butanol, and ethanol are present in the fermentation product mixture in a weight ratio of about 3 to about 6 to about 0.01-1. In yet other embodiments, the acetone, butanol, and ethanol are present in the fermentation product mixture in a weight ratio of about 3 to about 6 to about 1.

In certain embodiments of the composition in which the fermentation product mixture is made up of acetone, butanol, and ethanol, the amount of base to butanol and ethanol is between 0.3 to 1.5 mole equivalents. In other embodiments, the amount of base to butanol and ethanol is between 0.32 to 1.3 mole equivalents. In yet other embodiments, the amount of base to butanol and ethanol is between 0.95 to 1.3 mole equivalents.

In some embodiments that may be combined with any of the preceding embodiments, the metal-based catalyst may include nickel, ruthenium, rhodium, palladium, rhenium, iridium, platinum, copper, or combinations of these metals. In certain embodiments, the metal-based catalyst may be [Ir(COD)Cl]$_2$, RuCl$_2$(COD), PtCl$_2$(COD), [Rh(COD)Cl]$_2$, Ni/Si-Alumina, Ru/C, Rh/C, Pt/C, or Pd/C, or a combination of these metal-based catalysts. In yet other embodiments, the metal-based catalyst may include a palladium-based catalyst, such as Pd(OAc)$_2$, Pd$_2$(dba)$_3$, Pd(OH)$_2$/C, Pd/C, Pd/CaCO$_3$, Pd/Alumina, or Pd-polyethylenimines on silica, or a combination of these palladium-based catalysts.

In some embodiments that may be combined with any of the preceding embodiments, the base may be K$_3$PO$_4$, KOH, Ba(OH)$_2$.8H$_2$O, K$_2$CO$_3$, KOAc, KH$_2$PO$_4$, Na$_2$HPO$_4$, pyridine, or Et$_3$N, or a combination of these bases.

In other embodiments that may be combined with any of the preceding embodiments, the composition further includes a solvent. In some embodiments, the solvent is an organic solvent. In certain embodiments, the solvent may be toluene, ethyl acetate, diethylene glycol dimethyl ether, monoglyme, butanol, diethylene glycol dibutyl ether, oleyl alcohol, or dibutyl phthalate, or a mixture of these solvents.

In yet other embodiments that may be combined with any of the preceding embodiments, the composition further includes one or more compounds that may be a ketone or an alcohol. In certain embodiments, the one or more compounds added to the fermentation product mixture may include $R^aC(=O)R^b$, $(R^c)H_2COH$, $(R^d)_2HCOH$, or $(R^e)_3COH$, in which $R^a$, $R^b$, $R^c$, $R^d$ and $R^e$ at each occurrence may be independently an optionally substituted alkyl, alkenyl, alkynyl, cycloalkyl, heterocycloalkyl, aryl, heteroaryl, or arylalkyl. In some embodiments, $R^a$, $R^b$, $R^c$, $R^d$ and $R^e$ at each occurrence may be independently an optionally substituted C1-C20 alkyl, C1-C20 alkenyl, or C1-C20 alkynyl. In some embodiments, $R^a$, $R^b$, $R^c$, $R^d$ and $R^e$ at each occurrence may be independently an optionally substituted C1-C15 alkyl. In one embodiment, at least one of $R^a$, $R^b$, $R^c$, $R^d$ and $R^e$ is methyl. In some embodiments, the one or more compounds are obtained from a biological process or a renewable source. In some embodiments, the one or more compounds are added to the fermentation product mixture before combination with the metal-based catalyst and the base.

Another aspect of the present disclosure provides a method B of producing one or more compounds of Formula I,

(Formula I)

in which each $R_1$ and $R_2$ is independently an optionally substituted alkyl, alkenyl, alkynyl, cycloalkyl, heterocycloalkyl, aryl, heteroaryl, or arylalkyl; and in which the method includes: a) providing the composition A described above; and b) heating the composition to a temperature sufficient to form the one or more compounds of Formula I, in which at least one of the one or more compounds of Formula I is a double-alkylated compound.

In one embodiment of method B, each $R_1$ and $R_2$ is independently an optionally substituted alkyl, cycloalkyl, heterocycloalkyl, aryl, heteroaryl, or arylalkyl. In another embodiment, each $R_1$ and $R_2$ may independently be an optionally substituted alkyl, alkenyl, or alkynyl. In another embodiment, each $R_1$ and $R_2$ is independently an optionally substituted alkyl. In another embodiment, each $R_1$ and $R_2$ is independently an optionally substituted C1-C30 alkyl. In another embodiment, each $R_1$ and $R_2$ is independently an optionally substituted C1-C20 alkyl. In another embodiment, each $R_1$ and $R_2$ is independently an optionally substituted C1-C15 alkyl. In yet another embodiment, each $R_1$ and $R_2$ is independently an optionally substituted C1-C9 alkyl. In yet another embodiment, each $R_1$ and $R_2$ is independently an optionally substituted C1-C8 alkyl. In yet another embodiment, each $R_1$ and $R_2$ is independently an optionally substituted C1-C5 alkyl. In yet other embodiments, each $R_1$ and $R_2$ is independently an unsubstituted C1-C5 alkyl. In yet other embodiments, each $R_1$ and $R_2$ is independently methyl, ethyl, propyl, isopropyl, butyl, or pentyl. In yet other embodiments, each $R_1$ and $R_2$ is independently methyl, propyl, isopropyl, or pentyl. In some embodiments, $R_1$ and $R_2$ may be the same or different.

In some embodiments that may be combined with any of the preceding embodiments of method B, the temperature is between 110° C. to 145° C. In certain embodiments, the temperature is between 100° C. to 200° C. In other embodiments, the temperature is between 110° C. to 180° C. In yet other embodiments, the temperature is between 110° C. to 145° C. In yet other embodiments, the temperature is between 140° C. to 220° C.

In some embodiments that may be combined with any of the preceding embodiments of method B, the one or more compounds of Formula I may include pentanone, heptanone, nonanone, and undecanone. In certain embodiments, the one or more compounds of Formula I may include unbranched or branched pentanone, unbranched or branched heptanone, unbranched or branched nonanone, unbranched or branched undecanone, unbranched or branched tridecanone, and/or unbranched or branched pentadecanone.

In some embodiments, the one or more compounds of Formula I may include 2-pentanone, 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and/or 5-butyl-7-ethylundecan-6-one. In certain embodiments, the one or more compounds of Formula I may include 2-pentanone, 4-heptanone, 2-heptanone, 4-nonanone, 2-methyl-4-nonanone, and 6-undecanone. In yet other embodiments, the one or more compounds of Formula I may include 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and 5-butyl-7-ethylundecan-6-one.

In certain embodiments, the one or more compounds of Formula I is a mixture of compounds selected from 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and/or 5-butyl-7-ethylundecan-6-one.

In some embodiments that may be combined with any of the preceding embodiments of method B, the yield of the one or more compounds of Formula I relative to the amount of acetone present in the fermentation product mixture is at least 35%, at least 40%, at least 50%, at least 60%, at least 75%, at least 80%, at least 85%, at least 90%, at least 95%, or at least 99%. In other embodiments, the yield of the one or more compounds of Formula I relative to the amount of acetone present in the fermentation product mixture is between about 35-95%, between about 50-95%, between about 60-90%, between about 70-85%.

In some embodiments of method B, the method produces two or more compounds of Formula I, in which at least two of the two or more compounds of Formula I are double-alkylated compounds. In some embodiments, the yield of the two or more compounds of Formula I relative to the amount of acetone present in the fermentation mixture is at least 10%, at least 15%, at least 20%, at least 30%, at least 40%, at least 50%, at least 60%, at least 70%, at least 75%, at least 80%, at least 85%, or at least 90%. In some embodiments, the yield of the double-alkylated compounds of Formula I relative to the amount of acetone present in the fermentation product mixture is at least 10%, at least 15%, at least 20%, at least 30%, at least 40%, at least 50%, at least 60%, at least 70%, at least 75%, at least 80%, at least 85%, or at least 90%. In other embodiments, the yield of the double-alkylated compounds of Formula I relative to the amount of acetone present in the fermentation product mixture is between about 10-90%, between about 10-85%, between about 15-70%, or between about 15-65%.

In other embodiments that may be combined with any of the preceding embodiments of method B, the one or more products of Formula I may serve as one or more precursors for fuel additives. In yet other embodiments that may be combined with any of the preceding embodiments, the one or more products of Formula I may serve as one or more precursors for fuel. In yet other embodiments that may be combined with any of the preceding embodiments, the one or more products of Formula I may serve as one or more precursors for lubricants.

In yet other embodiments that may be combined with any of the preceding embodiments of method B, the method further includes adding one or more compounds to the fermentation product mixture, in which the one or more compounds may be a ketone or an alcohol. In certain embodiments, the one or more compounds added to the fermentation product mixture may include $R^aC(\!=\!O)R^b$, $(R^c)H_2COH$, $(R^d)_2HCOH$, or $(R^e)_3COH$, in which $R^a$, $R^b$, $R^c$, $R^d$ and $R^e$ at each occurrence may be independently an optionally substituted alkyl, alkenyl, alkynyl, cycloalkyl, heterocycloalkyl, aryl, heteroaryl, or arylalkyl. In some embodiments, $R^a$, $R^b$, $R^c$, $R^d$ and $R^e$ at each occurrence may be independently an optionally substituted C1-C20 alkyl, C1-C20 alkenyl, or C1-C20 alkynyl. In some embodiments, $R^a$, $R^b$, $R^c$, $R^d$ and $R^e$ at each occurrence may be independently an optionally substituted C1-C15 alkyl. In one embodiment, at least one of $R^a$, $R^b$, $R^c$, $R^d$ and $R^e$ is methyl. In some embodiments, the one or more compounds added to the fermentation product mixture are obtained from a biological process or a renewable source. In some embodiments, the one or more compounds are added to the fermentation product mixture before combination with the metal-based catalyst and the base.

In another embodiment that may be combined with any of the preceding embodiments of method B, the method further includes hydrogenating, deformylating, isomerizing, hydrodeoxygenating, or catalytic reforming the one or more compounds of Formula I produced by the methods described herein. In one embodiment, the hydrogenating, deformylating, isomerizing, hydrodeoxygenating, or catalytic reforming of the one or more compounds of Formula I involves a one-pot, multi-step process. In other embodiments of method B, the method further includes combining the one or more compounds of Formula I with a second metal-based catalyst. In some embodiments, the second metal-based catalyst includes a metal selected from the group consisting of platinum, nickel, molybdenum, tungsten, cobalt, and combinations of these metals. In certain embodiments, the second metal-based catalyst includes platinum, nickel-molybdenum (Ni—Mo), nickel-tungsten (Ni—W), cobalt-molybdenum (Co—Mo), and combinations of these metals. In specific embodiments, the second metal-based catalyst may be Pd/C, NiO—MoO$_3$/Al$_2$O$_3$, Pt/SiO$_2$—Al$_2$O$_3$, or combinations of these catalysts. In other embodiments, the combining of the one or more compounds of Formula I with the second metal-based catalyst converts the one or more compounds of Formula I into one or more alcohols. In yet other embodiments, the combining of the one or more compounds of Formula I with the second metal-based catalyst converts the one or more compounds of Formula I into one or more alkanes.

In some embodiments of method B, a fuel is produced following the hydrogenating, deformylating, isomerizing, hydrodeoxygenating, or catalytic reforming steps. In some embodiments of method B, a lubricant is produced following the hydrogenating, deformylating, isomerizing, hydrodeoxygenating, or catalytic reforming steps.

Another aspect of the present disclosure provides the use of the one or more compounds of Formula I produced by method B for the manufacture of a fuel or a lubricant.

Another aspect of the present disclosure provides a method C of producing one or more compounds of Formula II or III,

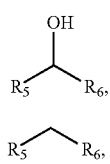
(Formula II)

(Formula III)

in which the method includes: a) providing a fermentation product mixture that includes acetone and one or more optionally substituted alcohols; b) combining the fermentation product mixture with a metal-based catalyst in the presence of a base; c) producing one or more compounds of Formula I,

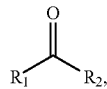
(Formula I)

in which at least one of the one or more compounds of Formula I is a double-alkylated compound; and d) converting the one or more compounds of Formula I into one or more compounds of Formula II or III, in which each $R_1$, $R_2$, $R_5$ and $R_6$ is independently an optionally substituted alkyl, alkenyl, alkynyl, cycloalkyl, heterocycloalkyl, aryl, heteroaryl, or arylalkyl. In some embodiments of method C, the converting in step (d) employs hydrogenating, deformylating, isomerizing, hydrodeoxygenating, or catalytic reforming the one or more compounds of Formula I to produce one or more compounds of Formula II or III.

In some embodiments that may be combined with any of the preceding embodiments of method C, each $R_1$ and $R_2$ may independently be an optionally substituted alkyl, alkenyl, or alkynyl. In another embodiment, each $R_1$ and $R_2$ is independently an optionally substituted C1-C20 alkyl, or C1-C20 alkenyl. In one embodiment, each $R_1$ and $R_2$ is independently an optionally substituted alkyl. In another embodiment, each $R_1$ and $R_2$ is independently an optionally substituted C1-C30 alkyl. In another embodiment, each $R_1$ and $R_2$ is independently an optionally substituted C1-C20 alkyl. In another embodiment, each $R_1$ and $R_2$ is independently an optionally substituted C1-C15 alkyl. In yet another embodiment, each $R_1$ and $R_2$ is independently an optionally substituted C1-C9 alkyl. In yet another embodiment, each $R_1$ and $R_2$ is independently an optionally substituted C1-C8 alkyl. In yet another embodiment, each $R_1$ and $R_2$ is independently an optionally substituted C1-C5 alkyl. In yet other embodiments, each $R_1$ and $R_2$ is independently an unsubstituted C1-C5 alkyl. In yet other embodiments, each $R_1$ and $R_2$ is independently methyl, ethyl, propyl, isopropyl, butyl, or pentyl. In yet other embodiments, each $R_1$ and $R_2$ is independently methyl, propyl, isopropyl, or pentyl. In some embodiments, $R_1$ and $R_2$ may be the same or different.

In one embodiment that may be combined with any of the preceding embodiments of method C, each $R_5$ and $R_6$ is independently an optionally substituted alkyl, cycloalkyl, heterocycloalkyl, aryl, heteroaryl, or arylalkyl. In one embodiment, each $R_5$ and $R_6$ is independently an optionally substituted alkyl. In another embodiment, each $R_5$ and $R_6$ is independently an optionally substituted C1-C20 alkyl. In another embodiment, each $R_1$ and $R_2$ is independently an optionally substituted C1-C15 alkyl. In yet another embodiment, each $R_5$ and $R_6$ is independently an optionally substituted C1-C9 alkyl. In yet another embodiment, each $R_5$ and $R_6$ is independently an optionally substituted C1-C8 alkyl. In yet another embodiment, each $R_5$ and $R_6$ is independently an optionally substituted C1-C5 alkyl. In yet other embodiments, each $R_5$ and $R_6$ is independently an unsubstituted C1-C5 alkyl. In yet other embodiments, each $R_5$ and $R_6$ is independently methyl, ethyl, propyl, isopropyl, butyl, or pentyl. In yet other embodiments, each $R_5$ and $R_6$ is independently methyl, propyl, isopropyl, or pentyl. In some embodiments, $R_5$ and $R_6$ may be the same or different.

In some embodiments that may be combined with any of the preceding embodiments of method C, the providing of the fermentation product mixture includes: providing a saccharide; contacting the saccharide with a fermentation host to produce the fermentation product mixture. In some embodiments, the saccharide may include C5 saccharides, C6 saccharides, or a mixture thereof. In certain embodiments, the saccharide may include glucose, sucrose, cellobiose and xylose, or a combination thereof. In certain embodiments, the saccharides may be derived from biomass, which may include cellulose, hemicellulose, and/or lignin. In certain embodiments, the providing of the fermentation product mixture further includes contacting the saccharide and the fermentation host with an extractant. In some embodiments, the extractant has one or more of the following properties: i) is non-toxic to fermentation host (e.g., *Clostridium*); ii) has partition coefficients for acetone and butanol equal to or greater than 1; and iii) has a partition coefficient for ethanol of less than 0.5. In other embodiments, the extractant is selected from glyceryl tributyrate, glyceryl tripropionate, oleyl alcohol, and polypropylene glycol, or a combination thereof. In yet other embodiments, the fermentation product mixture has less than about 5 wt %, about 4 wt %, about 3 wt %, about 2 wt %, or about 1 wt % water.

In some embodiments of method C, each of the one or more optionally substituted alcohols is independently a primary alcohol or a secondary alcohol. In yet another embodiment, each of the one or more optionally substituted alcohols is independently a C1-C20 primary alcohol or a C1-C20 secondary alcohol. In yet another embodiment, each of the one or more optionally substituted alcohols is independently a C1-C15 primary alcohol or a C1-C15 secondary alcohol. In yet another embodiment, each of the one or more optionally substituted alcohols is independently a C1-C8 primary alcohol or a C1-C8 secondary alcohol. In yet another embodiment, each of the one or more optionally substituted alcohols is independently a C1-C5 primary alcohol or a C1-C5 secondary alcohol. In some embodiments, the one or more optionally substituted alcohols are two unsubstituted primary alcohols, two unsubstituted secondary alcohols, one unsubstituted primary alcohol and one unsubstituted secondary alcohol.

In some embodiments that may be combined with any of the preceding embodiments of method C, the fermentation product mixture is made up of acetone and one optionally substituted alcohol. In other embodiments, the fermentation product mixture is made up of acetone and two optionally substituted alcohols. In yet other embodiments, the fermentation product mixture is made up of acetone and two or more optionally substituted alcohols. In certain embodiments, the optionally substituted alcohols are C1-C14 primary alcohols. In other embodiments, the fermentation product mixture is made up of acetone and two or more optionally substituted C1-C8 primary alcohols. In yet other embodiments, the fermentation product mixture is made up of acetone and two or more optionally substituted C1-C4 primary alcohols. In yet other embodiments, the fermentation product mixture is made up of acetone, a first C1-C4 primary alcohol, and a second C1-C4 primary alcohol. In other embodiments, the fermentation product mixture is made up of acetone, butanol, and ethanol.

In certain embodiments that may be combined with any of the preceding embodiments of method C, the acetone, the first C1-C4 primary alcohol, and the second C1-C4 primary alcohol are present in the fermentation product mixture in a weight ratio of about 2-4 acetone to about 5-7 first primary alcohol to about 0.01-2 second primary alcohol. In some embodiments, the acetone, butanol, and ethanol are present in the fermentation product mixture in a weight ratio of about 2-4 acetone to about 5-7 butanol to about 0.01-2 ethanol. In other embodiments, the acetone, butanol, and ethanol are present in the fermentation product mixture in a weight ratio of about 3 to about 6 to about 0.01-1. In yet other embodiments, the acetone, butanol, and ethanol are present in the fermentation product mixture in a weight ratio of about 3 to about 6 to about 1.

In certain embodiments of method C in which the fermentation product mixture is made up of acetone, butanol, and ethanol, the amount of base to butanol and ethanol is between 0.3 to 1.5 mole equivalents. In other embodiments, the amount of base to butanol and ethanol is between 0.32 to 1.3 mole equivalents. In yet other embodiments, the amount of base to butanol and ethanol is between 0.95 to 1.3 mole equivalents.

In some embodiments that may be combined with any of the preceding embodiments of method C, the metal-based catalyst may include nickel, ruthenium, rhodium, palladium, rhenium, iridium, platinum, copper, or combinations of these metals. In certain embodiments, the metal-based catalyst may be [Ir(COD)Cl]$_2$, RuCl$_2$(COD), PtCl$_2$(COD), [Rh(COD)Cl]$_2$, Ni/Si-Alumina, Ru/C, Rh/C, Pt/C, or Pd/C, or a combination of these metal-based catalysts. In yet other embodiments, the metal-based catalyst may include a palladium-based catalyst, such as Pd(OAc)$_2$, Pd$_2$(dba)$_3$, Pd(OH)$_2$/C, Pd/C, Pd/CaCO$_3$, Pd/Alumina, or Pd-polyethylenimines on silica, or a combination of these palladium-based catalysts.

In some embodiments that may be combined with any of the preceding embodiments of method C, the base may be K$_3$PO$_4$, KOH, Ba(OH)$_2$·8H$_2$O, K$_2$CO$_3$, KOAc, KH$_2$PO$_4$, Na$_2$HPO$_4$, pyridine, or Et$_3$N, or a combination of these bases.

In other embodiments that may be combined with any of the preceding embodiments of method C, the method further includes combining the fermentation product mixture in step (c) with a solvent. In some embodiments, the solvent is an organic solvent. In certain embodiments, the solvent may be toluene, ethyl acetate, diethylene glycol dimethyl ether, monoglyme, butanol, diethylene glycol dibutyl ether, oleyl alcohol, or dibutyl phthalate, or a mixture of these solvents. In yet other embodiments, the method is performed neat.

In some embodiments that may be combined with any of the preceding embodiments of method C, the method further includes heating the reaction mixture of step (c) to a temperature sufficient to form the one or more compounds of Formula I. In certain embodiments, the temperature is between 100° C. to 200° C. In other embodiments, the temperature is between 110° C. to 180° C. In yet other embodiments, the temperature is between 110° C. to 145° C. In yet other embodiments, the temperature is between 140° C. to 220° C.

In some embodiments that may be combined with any of the preceding embodiments of method C, the yield of the one or more compounds of Formula I relative to the amount of acetone present in the fermentation product mixture is at least 35%, at least 40%, at least 50%, at least 60%, at least 75%, at least 80%, at least 85%, at least 90%, at least 95%, or at least 99%. In other embodiments, the yield of the one or more compounds of Formula I relative to the amount of acetone present in the fermentation product mixture is between about 35-95%, at least 50-95%, at least 60-90%, or at least 70-85%.

In some embodiments of method C, the method produces two or more compounds of Formula I, in which at least two of the two or more compounds of Formula I are double-alkylated compounds. In some embodiments, the yield of the two or more compounds of Formula I relative to the amount of acetone present in the fermentation mixture is at least 10%, 15%, at least 20%, at least 30%, at least 40%, at least 50%, at least 60%, at least 70%, at least 75%, at least 80%, at least 85%, or at least 90%. In some embodiments, the yield of the double-alkylated compounds of Formula I relative to the amount of acetone present in the fermentation product mixture is at least 10%, at least 15%, at least 20%, at least 30%, at least 40%, at least 50%, at least 60%, at least 70%, at least 75%, at least 80%, at least 85%, or at least 90%. In other embodiments, the yield of the double-alkylated compounds of Formula I relative to the amount of acetone present in the fermentation product mixture is between about 10-90%, between about 10-85%, between about 15-70%, or between about 15-65%.

In some embodiments that may be combined with any of the preceding embodiments of method C, the one or more compounds of Formula I produced in step (c) may include pentanone, heptanone, nonanone, and undecanone. In certain embodiments, the one or more compounds of Formula I may include unbranched or branched pentanone, unbranched or branched heptanone, unbranched or branched nonanone, unbranched or branched undecanone, unbranched or branched tridecanone, and/or unbranched or branched pentadecanone.

In some embodiments, the one or more compounds of Formula I may include 2-pentanone, 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and/or 5-butyl-7-ethylundecan-6-one. In certain embodiments, the one or more compounds of Formula I may include 2-pentanone, 4-heptanone, 2-heptanone, 4-nonanone, 2-methyl-4-nonanone, and 6-undecanone. In yet other embodiments, the one or more compounds of Formula I may include 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and 5-butyl-7-ethylundecan-6-one.

In certain embodiments, the one or more compounds of Formula I is a mixture of compounds selected from 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and/or 5-butyl-7-ethylundecan-6-one.

The one or more compounds of Formula I can then be converted into the one or more compounds of Formula II or III in step (d) of method C. In some embodiments of method C, the method produces one or more compounds of Formula II. In certain embodiments, the one or more compounds of Formula II may include pentanol, heptanol, nonanol, and undecanol. In certain embodiments, the one or more compounds of Formula II may include unbranched or branched pentanol, unbranched or branched heptanol, unbranched or branched nonanol, unbranched or branched undecanol, unbranched or branched tridecanol, and/or unbranched or branched pentadecanol.

In some embodiments, the one or more compounds of Formula II may include 2-pentanol, 4-heptanol, 2-heptanol, 4-nonanol, 2-methyl-4-nonanol, 6-undecanol, 5-ethylundecan-6-ol, 5,7-diethylundecan-6-ol, 5,7-dibutylundecan-6-ol, 9-ethyltridecan-6-ol, 5,11-diethylpentadecan-8-ol, 5-butylundecan-6-ol, and/or 5-butyl-7-ethylundecan-6-ol. In certain embodiments, the one or more compounds of Formula II may include 2-pentanol, 4-heptanol, 2-heptanol, 4-nonanol, 2-methyl-4-nonanol, and 6-undecanol. In yet other embodiments, the one or more compounds of Formula II may include 5-ethylundecan-6-ol, 5,7-diethylundecan-6-ol, 5,7-dibutylundecan-6-ol, 9-ethyltridecan-6-ol, 5,11-diethylpentadecan-8-ol, 5-butylundecan-6-ol, and 5-butyl-7-ethylundecan-6-ol.

In some embodiments of method C, the one or more compounds of Formula II is a mixture of compounds selected from 2-pentanol, 4-heptanol, 2-heptanol, 4-nonanol, 2-methyl-4-nonanol, 6-undecanol, 5-ethylundecan-6-ol, 5,7-diethylundecan-6-ol, 5,7-dibutylundecan-6-ol, 9-ethyltridecan-6-ol, 5,11-diethylpentadecan-8-ol, 5-butylundecan-6-ol, and/or 5-butyl-7-ethylundecan-6-ol.

In some embodiments of method C, the method produces one or more compounds of Formula III. In certain embodiments, the one or more compounds of Formula III pentane, heptane, nonane, and undecane. In certain embodiments, the one or more compounds of Formula III may include unbranched or branched pentane, unbranched or branched heptane, unbranched or branched nonane, unbranched or branched undecane, unbranched or branched tridecane, and/or unbranched or branched pentadecane.

In some embodiments, the one or more compounds of Formula III may include pentane, heptane, nonane, 2-methyl-nonane, undecane, 5-ethylundecane, 5,7-diethylundecane, 5,7-dibutylundecane, 9-ethyltridecane, 5,11-diethylpentadecane, 5-butylundecane, and/or 5-butyl-7-ethylundecane. In certain embodiments, the one or more compounds of Formula III may include pentane, heptane, nonane, 2-methyl-nonane, undecane. In yet other embodiments, the one or more compounds of Formula I may include 5-ethylundecane, 5,7-diethylundecane, 5,7-dibutylundecane, 9-ethyltridecane, 5,11-diethylpentadecane, 5-butylundecane, and/or 5-butyl-7-ethylundecane.

In some embodiments, the one or more compounds of Formula III is a mixture of compounds selected from pentane, heptane, nonane, 2-methyl-nonane, undecane, 5-ethylundecane, 5,7-diethylundecane, 5,7-dibutylundecane, 9-ethyltridecane, 5,11-diethylpentadecane, 5-butylundecane, and/or 5-butyl-7-ethylundecane.

In another embodiment that may be combined with any of the preceding embodiments of method C, steps (a)-(d) are performed as a one-pot, multi-step process. In other embodiments of method C, a second metal-based catalyst is added to step (d) for hydrogenating, deformylating, isomerizing, hydrodeoxygenating, or catalytic reforming of the one or more compounds of Formula. In some embodiments, the second metal-based catalyst includes a metal selected from the group consisting of platinum, nickel, molybdenum, tungsten, cobalt, and combinations of these metals. In certain embodiments, the second metal-based catalyst includes platinum, nickel-molybdenum (Ni—Mo), nickel-tungsten (Ni—W), cobalt-molybdenum (Co—Mo), and combinations of these metals. In specific embodiments, the second metal-based catalyst may be Pd/C, NiO—MoO$_3$/Al$_2$O$_3$, Pt/SiO$_2$—Al$_2$O$_3$, or combinations of these catalysts.

In some embodiments, a fuel or a lubricant is produced by method C.

Another aspect of the present disclosure provides the use of the one or more compounds of Formula II or III produced by method C as a fuel or a lubricant.

Another aspect of the present disclosure provides a method D of producing one or more compounds of Formula I,

(Formula I)

in which each $R_1$ and $R_2$ is independently an optionally substituted alkyl, alkenyl, alkynyl, cycloalkyl, heterocycloalkyl, aryl, heteroaryl, or arylalkyl; and in which the method includes: a) providing a fermentation product mixture that includes a ketone and one or more optionally substituted alcohols; b) combining the fermentation product mixture with a metal-based catalyst in the presence of a base; and c) producing one or more compounds of Formula I.

In some embodiments that may be combined with any of the preceding embodiments of method D, the providing of the fermentation product mixture includes: providing a saccharide; contacting the saccharide with a fermentation host to produce the fermentation product mixture. In some embodiments, the saccharide may include C5 saccharides, C6 saccharides, or a mixture thereof. In certain embodiments, the saccharide may include glucose, sucrose, cellobiose and xylose, or a combination thereof. In certain embodiments, the saccharides may be derived from biomass, which may include cellulose, hemicellulose, and/or lignin. In certain embodiments, the providing of the fermentation product mixture further includes contacting the saccharide and the fermentation host with an extractant. In some embodiments, the extractant has one or more of the following properties: i) is non-toxic to fermentation host (e.g., *Clostridium*); ii) has partition coefficients for acetone and butanol equal to or greater than 1; and iii) has a partition coefficient for ethanol of less than 0.5. In other embodiments, the extractant is selected from glyceryl tributyrate, glyceryl tripropionate, oleyl alcohol, and polypropylene glycol, or a combination thereof. In yet other embodiments, the fermentation product mixture has less than about 5 wt %, about 4 wt %, about 3 wt %, about 2 wt %, or about 1 wt % water.

In some embodiments of method D, at least one of the one or more compounds of Formula I produced is a double-alkylated compound.

In one embodiment of method D, each $R_1$ and $R_2$ may independently be an optionally substituted alkyl, cycloalkyl, heterocycloalkyl, aryl, heteroaryl, or arylalkyl. In another embodiment, each $R_1$ and $R_2$ may independently be an optionally substituted alkyl, alkenyl, or alkynyl. In another embodiment, each $R_1$ and $R_2$ is independently an optionally substituted alkyl. In another embodiment, each $R_1$ and $R_2$ is independently an optionally substituted C1-C30 alkyl. In another embodiment, each $R_1$ and $R_2$ is independently an optionally substituted C1-C20 alkyl. In yet another embodiment, each $R_1$ and $R_2$ is independently an optionally substituted C1-C9 alkyl. In yet another embodiment, each $R_1$ and $R_2$ is independently an optionally substituted C1-C8 alkyl. In yet another embodiment, each $R_1$ and $R_2$ is independently an optionally substituted C1-C5 alkyl. In yet other embodiments, each $R_1$ and $R_2$ is independently an unsubstituted C1-C5 alkyl. In yet other embodiments, each $R_1$ and $R_2$ is independently methyl, ethyl, propyl, isopropyl, butyl, or pentyl. In yet other embodiments, each $R_1$ and $R_2$ is independently methyl, propyl, isopropyl, or pentyl. In some embodiments, $R_1$ and $R_2$ may be the same or different.

In one embodiment of method D, the ketone is $R_3C(=O)R_4$, wherein each $R_3$ and $R_4$ is independently an optionally substituted alkyl, alkenyl, alkynyl, cycloalkyl, heterocycloalkyl, aryl, heteroaryl, or arylalkyl. In another embodiment, each $R_3$ and $R_4$ is independently an optionally substituted C1-C20 alkyl, C1-C20 alkenyl, or C1-C20 alkynyl. In another embodiment, each $R_3$ and $R_4$ is independently an optionally substituted C1-C20 alkyl, or C1-C20 alkenyl. In another embodiment, each $R_3$ and $R_4$ is independently an optionally substituted C1-C20 alkyl. In yet another embodiment, each $R_3$ and $R_4$ is independently an optionally substituted C1-C15 alkyl. In another embodiment, each $R_3$ and $R_4$ is independently an optionally substituted C1-C9 alkyl. In another embodiment, each $R_3$ and $R_4$ is independently an optionally substituted C1-C8 alkyl. In another embodiment, each $R_3$ and $R_4$ is independently an optionally substituted C1-C5 alkyl. In one embodiment, one of $R_3$ and $R_4$ is methyl. In another embodiment, the ketone is acetone. In some embodiments, $R_3$ and $R_4$ may be the same or different.

In some embodiments of method D, each of the one or more optionally substituted alcohols is independently a primary alcohol or a secondary alcohol. In other embodiments, each of the one or more optionally substituted alcohols is independently a C1-C20 primary alcohol or a C1-C20 secondary alcohol. In yet another embodiment, each of the one or more optionally substituted alcohols is independently a C1-C15 primary alcohol or a C1-C15 secondary alcohol. In yet another embodiment, each of the one or more optionally substituted alcohols is independently a C1-C8 primary alcohol or a C1-C8 secondary alcohol. In yet another embodiment, each of the one or more optionally substituted alcohols is independently a C1-C5 primary alcohol or a C1-C5 secondary alcohol. In some embodiments, the one or more optionally substituted alcohols are one or more unsubstituted primary alcohols or unsubstituted secondary alcohols.

In yet other embodiments, the one or more optionally substituted alcohols is one optionally substituted alcohol. In yet other embodiments, the one optionally substituted alcohol is an unsubstituted primary alcohol or unsubstituted secondary alcohol. In yet other embodiments, the one or more optionally substituted alcohols are two optionally substituted alcohols. In certain embodiments, the two optionally substituted alcohols are two unsubstituted primary alcohols. In certain embodiments, the two optionally substituted alcohols are one unsubstituted primary alcohol and one unsubstituted secondary alcohol.

In some embodiments of method D, the fermentation product mixture is made up of a ketone and one or more optionally substituted C1-C14 alcohols. In other embodiments, the fermentation product mixture is made up of a ketone and one or more optionally substituted C1-C8 alcohols. In yet other embodiments, the fermentation product mixture is made up of a ketone and one or more optionally substituted C1-C4 alcohols. In some embodiments, a ketone and one optionally substituted alcohol. In some embodiments, the fermentation product mixture that includes acetone and two optionally substituted alcohols. In yet other embodiments, the fermentation product mixture is made up of a ketone, a first C1-C4 alcohol, and a second C1-C4 alcohol. In other embodiments, the fermentation product mixture is made up of acetone, butanol, and ethanol.

In certain embodiments of method D in which the fermentation product mixture is made up of acetone, butanol, and ethanol, the amount of base to butanol and ethanol is between 0.3 to 1.5 mole equivalents. In other embodiments, the amount of base to butanol and ethanol is between 0.32 to 1.3 mole equivalents. In yet other embodiments, the amount of base to butanol and ethanol is between 0.95 to 1.3 mole equivalents.

In some embodiments that may be combined with any of the preceding embodiments of method D, the metal-based catalyst may include nickel, ruthenium, rhodium, palladium, rhenium, iridium, platinum, copper, or combinations of these metals. In certain embodiments, the metal-based catalyst may be $[Ir(COD)Cl]_2$, $RuCl_2(COD)$, $PtCl_2(COD)$, [Rh (COD)Cl]$_2$, Ni/Si-Alumina, Ru/C, Rh/C, Pt/C, Pd/C, or combinations of these metal-based catalysts. In yet other embodiments, the metal-based catalyst may include a palladium-based catalyst, such as Pd(OAc)$_2$, Pd$_2$(dba)$_3$, Pd(OH)$_2$/C, Pd/C, Pd/CaCO$_3$, Pd/Alumina, Pd-polyethylenimines on silica, or combinations of these palladium-based catalysts.

In some embodiments that may be combined with any of the preceding embodiments of method D, the base may be K$_3$PO$_4$, KOH, Ba(OH)$_2$.8H$_2$O, K$_2$CO$_3$, KOAc, KH$_2$PO$_4$, Na$_2$HPO$_4$, pyridine, Et$_3$N, or combinations of these bases.

In other embodiments that may be combined with any of the preceding embodiments of method D, the method further includes combining the fermentation product mixture in step (b) with a solvent. In some embodiments, the solvent is an organic solvent. In certain embodiments, the solvent may be toluene, ethyl acetate, diethylene glycol dimethyl ether, monoglyme, butanol, diethylene glycol dibutyl ether, oleyl alcohol, dibutyl phthalate, or mixtures of these solvents. In yet other embodiments, the method is performed neat.

In some embodiments that may be combined with any of the preceding embodiments of method D, the method further includes heating the reaction mixture of step (b) to a temperature sufficient to form the one or more compounds of Formula I. In certain embodiments, the temperature is between 100° C. to 200° C. In other embodiments, the temperature is between 110° C. to 180° C. In yet other embodiments, the temperature is between 110° C. to 145° C. In yet other embodiments, the temperature is between 140° C. to 220° C.

In some embodiments that may be combined with any of the preceding embodiments of method D, the one or more compounds of Formula I may include pentanone, heptanone, nonanone, and undecanone. In certain embodiments, the one or more compounds of Formula I may include unbranched or branched pentanone, unbranched or branched heptanone, unbranched or branched nonanone, unbranched or branched undecanone, unbranched or branched tridecanone, and/or unbranched or branched pentadecanone.

In some embodiments, the one or more compounds of Formula I may include 2-pentanone, 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and/or 5-butyl-7-ethylundecan-6-one. In certain embodiments, the one or more compounds of Formula I may include 2-pentanone, 4-heptanone, 2-heptanone, 4-nonanone, 2-methyl-4-nonanone, and 6-undecanone. In yet other embodiments, the one or more compounds of Formula I may include 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and 5-butyl-7-ethylundecan-6-one.

In some embodiments, the one or more compounds of Formula I is a mixture of compounds selected from 2-pentanone, 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and/or 5-butyl-7-ethylundecan-6-one.

In some embodiments that may be combined with any of the preceding embodiments of method D, the yield of the one or more compounds of Formula I relative to the amount of ketone present in the fermentation product mixture is at least 35%, at least 40%, at least 50%, at least 60%, at least 75%, at least 80%, at least 85%, at least 90%, 95%, or at least 99%. In other embodiments, the yield of the one or more compounds of Formula I relative to the amount of ketone present in the fermentation product mixture is between about 35-95%, at least 50-95%, at least 60-90%, or at least 70-85%.

In some embodiments of method D, the method produces two or more compounds of Formula I, in which at least two of the two or more compounds of Formula I are double-alkylated compounds. In some embodiments, the yield of the two or more compounds of Formula I relative to the amount of ketone present in the fermentation mixture is at least 10%, at least 15%, at least 20%, at least 30%, at least 40%, at least 50%, at least 60%, at least 70%, at least 75%, at least 80%, at least 85%, or at least 90%. In some embodiments, the yield of the double-alkylated compounds of Formula I relative to the amount of ketone present in the fermentation product mixture is at least 10%, at least 15%, at least 20%, at least 30%, at least 40%, at least 50%, at least 60%, at least 70%, at least 75%, at least 80%, at least 85%, or at least 90%. In other embodiments, the yield of the double-alkylated compounds of Formula I relative to the amount of ketone present in the fermentation product mixture is between about 10-90%, between about 10-85%, between about 15-70%, or between about 15-65%.

In other embodiments that may be combined with any of the preceding embodiments of method D, the one or more products of Formula I may serve as one or more precursors for fuel additives. In other embodiments that may be combined with any of the preceding embodiments, the one or more products of Formula I may serve as one or more precursors for fuel. In other embodiments that may be combined with any of the preceding embodiments, the one or more products of Formula I may serve as one or more precursors for lubricants.

In yet other embodiments that may be combined with any of the preceding embodiments of method D, the method further includes adding one or more compounds to the fermentation product mixture, in which the one or more compounds may be a ketone or an alcohol. In some embodiments, the method further includes adding acetone to the fermentation product mixture. In certain embodiments, the one or more compounds added to the fermentation product mixture may be $R^aC(=O)R^b$, $(R^c)H_2COH$, $(R^d)_2HCOH$, or $(R^e)_3COH$, in which $R^a$, $R^b$, $R^c$, $R^d$ and $R^e$ may be independently an optionally substituted alkyl, alkenyl, alkynyl, cycloalkyl, heterocycloalkyl, aryl, heteroaryl, or arylalkyl. In some embodiments, $R^a$, $R^b$, $R^c$, $R^d$ and $R^e$ at each occurrence may be independently an optionally substituted C2-C14 alkyl or alkenyl. In other embodiments, $R^a$, $R^b$, $R^c$, $R^d$ and $R^e$ at each occurrence may be independently an optionally substituted C2-C14 alkyl. In one embodiment, at least one of $R^a$, $R^b$, $R^c$, $R^d$ and $R^e$ is methyl. In some embodiments, the one or more compounds added to the fermentation product mixture are obtained from a biological process or a renewable source. In some embodiments, the one or more compounds are added to the fermentation product mixture before combination with the metal-based catalyst and the base.

In another embodiment that may be combined with any of the preceding embodiments of method D, the method further includes hydrogenating, deformylating, isomerizing, hydrodeoxygenating, or catalytic reforming the one or more compounds of Formula I produced by the methods described herein. In one embodiment, the hydrogenating, deformylating, isomerizing, hydrodeoxygenating, or catalytic reforming of the one or more compounds of Formula I involves a one-pot, multi-step process. In other embodiments of method D, the method further includes combining the one or more compounds of Formula I with a second metal-based catalyst. In some embodiments, the second metal-based catalyst includes a metal selected from the group consisting of platinum, nickel, molybdenum, tungsten, cobalt, and combinations of these metals. In certain embodiments, the second metal-based catalyst includes platinum, nickel-molybdenum (Ni—Mo), nickel-tungsten (Ni—W), cobalt-molybdenum (Co—Mo), and combinations of these metals. In specific embodiments, the second metal-based catalyst may be Pd/C, NiO—$MoO_3$/$Al_2O_3$, Pt/$SiO_2$—$Al_2O_3$, or combinations of these catalysts. In other embodiments, the combining of the one or more compounds of Formula I with the second metal-based catalyst converts the one or more compounds of Formula I into one or more alcohols. In yet other embodiments, the combining of the one or more compounds of Formula I with the second metal-based catalyst converts the one or more compounds of Formula I into one or more alkanes.

In some embodiments of method D, a fuel or a lubricant is produced following the hydrogenating, deformylating, isomerizing, hydrodeoxygenating, or catalytic reforming steps.

Another aspect of the present disclosure provides the use of the one or more compounds of Formula I produced by method D for the manufacture of a fuel or a lubricant.

Another aspect of the present disclosure provides a composition B that includes:
 a fermentation product mixture that includes a ketone and one or more optionally substituted alcohols;
 a metal-based catalyst; and
 a base.

In some embodiments of composition B, the fermentation product mixture is produced by contacting the saccharide with a fermentation host to produce the fermentation product mixture. In some embodiments, the saccharide may include C5 saccharides, C6 saccharides, or a mixture thereof. In certain embodiments, the saccharide may include glucose, sucrose, cellobiose and xylose, or a combination thereof. In certain embodiments, the saccharides may be derived from biomass, which may include cellulose, hemicellulose, and/or lignin. In certain embodiments, the providing of the fermentation product mixture further includes contacting the saccharide and the fermentation host with an extractant. In some embodiments, the extractant has one or more of the following properties: i) is non-toxic to fermentation host (e.g., *Clostridium*); ii) has partition coefficients for acetone and butanol equal to or greater than 1; and iii) has a partition coefficient for ethanol of less than 0.5. In other embodiments, the extractant is selected from glyceryl tributyrate, glyceryl tripropionate, oleyl alcohol, and polypropylene glycol, or a combination thereof. In yet other embodiments, the fermentation product mixture has less than about 5 wt %, about 4 wt %, about 3 wt %, about 2 wt %, or about 1 wt % water.

In some embodiments of composition B, the ketone is $R_3C(=O)R_4$, wherein each $R_3$ and $R_4$ is independently an optionally substituted alkyl, alkenyl, alkynyl, cycloalkyl, heterocycloalkyl, aryl, heteroaryl, or arylalkyl. In another embodiment, each $R_3$ and $R_4$ is independently an optionally substituted C1-C20 alkyl, C1-C20 alkenyl, or C1-C20 alkynyl. In another embodiment, each $R_3$ and $R_4$ is independently an optionally substituted C1-C20 alkyl. In yet another embodiment, each $R_3$ and $R_4$ is independently an optionally substituted C1-C15 alkyl. In another embodiment, each $R_3$ and $R_4$ is independently an optionally substituted C1-C9 alkyl. In another embodiment, each $R_3$ and $R_4$ is independently an optionally substituted C1-C8 alkyl. In another embodiment, each $R_3$ and $R_4$ is independently an optionally substituted C1-C5 alkyl. In one embodiment, one of $R_3$ and $R_4$ is methyl. In another embodiment, the ketone is acetone. In some embodiments, $R_3$ and $R_4$ may be the same or different.

In another embodiment of composition B, each of the one or more optionally substituted alcohols is independently a primary alcohol or a secondary alcohol. In yet another embodiment, each of the one or more optionally substituted alcohols is independently a C1-C20 primary alcohol. In yet another embodiment, each of the one or more optionally substituted alcohols is independently a C1-C15 primary alcohol. In yet another embodiment, each of the one or more optionally substituted alcohols is independently a C1-C8 primary alcohol. In yet another embodiment, each of the one or more optionally substituted alcohols is independently a C1-C5 primary alcohol.

In other embodiments of composition B, the fermentation product mixture is made up of a ketone and one or more optionally substituted C1-C14 alcohols. In other embodiments, the fermentation product mixture is made up of a ketone and one or more optionally substituted C1-C8 alcohols. In yet other embodiments, the fermentation product mixture is made up of a ketone and one or more optionally substituted C1-C4 alcohols. In some embodiments, the fermentation product mixture is made up of a ketone and one optionally substituted alcohol.

In yet other embodiments of composition B, the fermentation product mixture is made up of a ketone and two optionally substituted alcohols. In certain embodiments, the fermentation product mixture is made up of a ketone, a first C1-C4 alcohol, and a second C1-C4 alcohol. In some embodiments, the fermentation product mixture is made up a ketone, a first optionally substituted alcohol, and a second optionally substituted alcohol. In some embodiments, the fermentation product mixture is made up a ketone, a first optionally substituted C1-C4 alcohol, and a second optionally substituted C1-C4 alcohol. In other embodiments, the fermentation product mixture is made up of acetone, butanol, and ethanol.

In certain embodiments that may be combined with any of the preceding embodiments, the ketone, the first optionally substituted alcohol, and the second optionally substituted alcohol are present in the fermentation product mixture in a weight ratio of about 2-4 acetone to about 5-7 first optionally substituted alcohol to about 0.01-2 second optionally substituted alcohol.

In some embodiments that may be combined with any of the preceding embodiments, the metal-based catalyst may include nickel, ruthenium, rhodium, palladium, rhenium, iridium, platinum, copper, or combinations of these metals. In certain embodiments, the metal-based catalyst may be $[Ir(COD)Cl]_2$, $RuCl_2(COD)$, $PtCl_2(COD)$, $[Rh(COD)Cl]_2$, Ru/C, Rh/C, Pt/C, Pd/C, or combinations of these metal-based catalysts. In yet other embodiments, the metal-based catalyst may include a palladium-based catalyst, such as $Pd(OAc)_2$, $Pd_2(dba)_3$, $Pd(OH)_2$/C, Pd/C, Pd/$CaCO_3$, Pd/Alumina, Pd-polyethylenimines on silica, or combinations of these palladium-based catalysts.

In some embodiments that may be combined with any of the preceding embodiments, the base may be $K_3PO_4$, KOH, $Ba(OH)_2 \cdot 8H_2O$, $K_2CO_3$, KOAc, $KH_2PO_4$, $Na_2HPO_4$, pyridine, $Et_3N$, or combinations of these bases.

In other embodiments that may be combined with any of the preceding embodiments, the composition further includes a solvent. In some embodiments, the solvent is an organic solvent. In certain embodiments, the solvent may be toluene, ethyl acetate, diethylene glycol dimethyl ether, monoglyme, butanol, diethylene glycol dibutyl ether, oleyl alcohol, dibutyl phthalate, or mixtures of these solvents.

In yet other embodiments that may be combined with any of the preceding embodiments, the composition further includes one or more compounds that may be a ketone, a secondary alcohol, or a tertiary alcohol. In certain embodiments, the one or more compounds may be $R^aC(=O)R^b$, $(R^c)H_2COH$, $(R^d)_2HCOH$, or $(R^e)_3COH$, in which $R^a$, $R^b$, $R^c$, $R^d$ and $R^e$ may be independently an optionally substituted alkyl, alkenyl, alkynyl, cycloalkyl, heterocycloalkyl, aryl, heteroaryl, or arylalkyl. In some embodiments, $R^a$, $R^b$, $R^c$, $R^d$ and $R^e$ at each occurrence may be independently an optionally substituted C2-C14 alkyl. In one embodiment, at least one of $R^a$, $R^b$, $R^c$, $R^d$ and $R^e$ is methyl. In some embodiments, the one or more compounds are obtained from a biological process or a renewable source. In some embodiments, the one or more compounds are added to the fermentation product mixture before combination with the metal-based catalyst and the base.

Another aspect of the present disclosure provides a method E of producing one or more compounds of Formula II or III,

(Formula II)

(Formula III)

in which the method includes: a) providing a fermentation product mixture that includes a ketone and one or more optionally substituted alcohols; b) combining the fermentation product mixture with a metal-based catalyst in the presence of a base; c) producing one or more compounds of Formula I,

(Formula I)

and
d) converting the one or more compounds of Formula I into one or more compounds of Formula II or III, in which each $R_1$, $R_2$, $R_5$ and $R_6$ is independently an optionally substituted alkyl, alkenyl, alkynyl, cycloalkyl, heterocycloalkyl, aryl, heteroaryl, or arylalkyl. In some embodiments of method E, the converting in step (d) employs hydrogenating, deformylating, isomerizing, hydrodeoxygenating, or catalytic reforming the one or more compounds of Formula I to produce one or more compounds of Formula II or III.

In some embodiments that may be combined with any of the preceding embodiments of method E, each $R_1$ and $R_2$ is independently an optionally substituted alkyl, alkenyl, or alkynyl. In one embodiment, each $R_1$ and $R_2$ is independently an optionally substituted alkyl. In another embodiment, each $R_1$ and $R_2$ is independently an optionally substituted C1-C30 alkyl. In another embodiment, each $R_1$ and $R_2$ is independently an optionally substituted C1-C20 alkyl. In yet another embodiment, each $R_1$ and $R_2$ is independently an optionally substituted C1-C9 alkyl. In yet another embodiment, each $R_1$ and $R_2$ is independently an optionally substituted C1-C8 alkyl. In yet another embodiment, each $R_1$ and $R_2$ is independently an optionally substituted C1-C5 alkyl. In yet other embodiments, each $R_1$ and $R_2$ is independently an unsubstituted C1-C5 alkyl. In yet other embodiments, each $R_1$ and $R_2$ is independently methyl, ethyl, propyl, isopropyl, butyl, or pentyl. In yet other embodiments, each $R_1$ and $R_2$ is independently methyl, propyl, isopropyl, or pentyl. In some embodiments, $R_1$ and $R_2$ may be the same or different.

In one embodiment that may be combined with any of the preceding embodiments of method E, each $R_5$ and $R_6$ is independently an optionally substituted alkyl, cycloalkyl, heterocycloalkyl, aryl, heteroaryl, or arylalkyl. In one embodiment, each $R_5$ and $R_6$ is independently an optionally substituted alkyl. In another embodiment, each $R_5$ and $R_6$ is independently an optionally substituted C1-C20 alkyl. In yet another embodiment, each $R_5$ and $R_6$ is independently an optionally substituted C1-C9 alkyl. In yet another embodiment, each $R_5$ and $R_6$ is independently an optionally substituted C1-C8 alkyl. In yet another embodiment, each $R_5$ and $R_6$ is independently an optionally substituted C1-C5 alkyl. In yet other embodiments, each $R_5$ and $R_6$ is independently an unsubstituted C1-C5 alkyl. In yet other embodiments, each $R_5$ and $R_6$ is independently methyl, ethyl, propyl, isopropyl, butyl, or pentyl. In yet other embodiments, each $R_5$ and $R_6$ is independently methyl, propyl, isopropyl, or pentyl. In some embodiments, $R_5$ and $R_6$ may be the same or different.

In some embodiments that may be combined with any of the preceding embodiments of method E, the providing of the fermentation product mixture includes: providing a saccharide; contacting the saccharide with a fermentation host to produce the fermentation product mixture. In some embodiments, the saccharide may include C5 saccharides, C6 saccharides, or a mixture thereof. In certain embodiments, the saccharide may include glucose, sucrose, cellobiose and xylose, or a combination thereof. In certain embodiments, the saccharides may be derived from biomass, which may include cellulose, hemicellulose, and/or lignin. In certain embodiments, the providing of the fermentation product mixture further includes contacting the saccharide and the fermentation host with an extractant. In some embodiments, the extractant has one or more of the following properties: i) is non-toxic to fermentation host (e.g., *Clostridium*); ii) has partition coefficients for acetone and butanol equal to or greater than 1; and iii) has a partition coefficient for ethanol of less than 0.5. In other embodiments, the extractant is selected from glyceryl tributyrate, glyceryl tripropionate, oleyl alcohol, and polypropylene glycol, or a combination thereof. In yet other embodiments, the fermentation product mixture has less than about 5 wt %, about 4 wt %, about 3 wt %, about 2 wt %, or about 1 wt % water.

In some embodiments of method E, the fermentation product mixture is made up of a ketone and one or more optionally substituted C1-C14 alcohols. In other embodiments, the fermentation product mixture is made up of a ketone and one or more optionally substituted C1-C8 alcohols. In yet other embodiments, the fermentation product mixture is made up of a ketone and one or more optionally substituted C1-C4 alcohols. In some embodiments, the fermentation product mixture is made up of a ketone and one optionally substituted alcohol.

In other embodiments, the fermentation product mixture is made up of a ketone and one optionally substituted alcohol. In yet other embodiments, the fermentation product mixture is made up of a ketone, a first C1-C4 alcohol, and a second C1-C4 alcohol. In other embodiments, the fermentation product mixture is made up of acetone, butanol, and ethanol.

In some embodiments that may be combined with any of the preceding embodiments of method E, the metal-based catalyst may include nickel, ruthenium, rhodium, palladium, rhenium, iridium, platinum, copper, or combinations of these metals. In certain embodiments, the metal-based catalyst may be [Ir(COD)Cl]$_2$, RuCl$_2$(COD), PtCl$_2$(COD), [Rh(COD)Cl]$_2$, Ni/Si-Alumina, Ru/C, Rh/C, Pt/C, Pd/C, or combinations of these metal-based catalysts. In yet other embodiments, the metal-based catalyst may include a palladium-based catalyst, such as Pd(OAc)$_2$, Pd$_2$(dba)$_3$, Pd(OH)$_2$/C, Pd/C, Pd/CaCO$_3$, Pd/Alumina, Pd-polyethylenimines on silica, or combinations of these palladium-based catalysts.

In some embodiments that may be combined with any of the preceding embodiments of method E, the base may be K$_3$PO$_4$, KOH, Ba(OH)$_2$.8H$_2$O, K$_2$CO$_3$, KOAc, KH$_2$PO$_4$, Na$_2$HPO$_4$, pyridine, Et$_3$N, or combinations of these bases.

In other embodiments that may be combined with any of the preceding embodiments of method E, the method further includes combining the fermentation product mixture in step (c) with a solvent. In some embodiments, the solvent is an organic solvent. In certain embodiments, the solvent may be toluene, ethyl acetate, diethylene glycol dimethyl ether, monoglyme, butanol, diethylene glycol dibutyl ether, oleyl alcohol, dibutyl phthalate, or mixtures of these solvents. In yet other embodiments, the method is performed neat.

In some embodiments that may be combined with any of the preceding embodiments of method E, the method further includes heating the reaction mixture of step (c) to a temperature sufficient to form the one or more compounds of Formula I. In certain embodiments, the temperature is between 100° C. to 200° C. In other embodiments, the temperature is between 110° C. to 180° C. In yet other embodiments, the temperature is between 110° C. to 145° C. In yet other embodiments, the temperature is between 140° C. to 220° C.

In some embodiments that may be combined with any of the preceding embodiments of method E, the yield of the one or more compounds of Formula I relative to the amount of ketone present in the fermentation product mixture is at least 35%, at least 40%, at least 50%, at least 60%, at least 75%, at least 80%, at least 85%, at least 90%, 95%, or at least 99%. In other embodiments, the yield of the one or more compounds of Formula I relative to the amount of ketone present in the fermentation product mixture is between about 35-95%, 50-95%, 60-90%, 70-85%.

In some embodiments of method E, the method produces two or more compounds of Formula I, in which at least two of the two or more compounds of Formula I are double-alkylated compounds. In some embodiments, the yield of the double-alkylated compounds of Formula I relative to the amount of ketone present in the fermentation product mixture is at least 10%, at least 15%, at least 20%, at least 30%, at least 40%, at least 50%, at least 60%, at least 70%, at least 75%, at least 80%, at least 85%, or at least 90%. In other embodiments, the yield of the double-alkylated compounds of Formula I relative to the amount of ketone present in the fermentation product mixture is between 10-90%, 10-85%, 15-70%, or 15-65%.

In some embodiments that may be combined with any of the preceding embodiments of method E, the one or more compounds of Formula I produced in step (c) may include pentanone, heptanone, nonanone, and undecanone. In certain embodiments, the one or more compounds of Formula I may include unbranched or branched pentanone, unbranched or branched heptanone, unbranched or branched nonanone, unbranched or branched undecanone, unbranched or branched tridecanone, and/or unbranched or branched pentadecanone.

In some embodiments, the one or more compounds of Formula I may include 2-pentanone, 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and/or 5-butyl-7-ethylundecan-6-one. In certain embodiments, the one or more compounds of Formula I may include 2-pentanone, 4-heptanone, 2-heptanone, 4-nonanone, 2-methyl-4-nonanone, and 6-undecanone. In yet other embodiments, the one or more compounds of Formula I may include 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and 5-butyl-7-ethylundecan-6-one.

In some embodiments, the one or more compounds of Formula I is a mixture of compounds selected from 2-pentanone, 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and/or 5-butyl-7-ethylundecan-6-one.

The one or more compounds of Formula I can then be converted into the one or more compounds of Formula II or III in step (d) of method E. In some embodiments of method E, the method produces one or more compounds of Formula II. In certain embodiments, the one or more compounds of Formula II may include pentanol, heptanol, nonanol, and undecanol. In certain embodiments, the one or more compounds of Formula II may include unbranched or branched pentanol, unbranched or branched heptanol, unbranched or branched nonanol, unbranched or branched undecanol, unbranched or branched tridecanol, and/or unbranched or branched pentadecanol.

In some embodiments, the one or more compounds of Formula II may include 2-pentanol, 4-heptanol, 2-heptanol, 4-nonanol, 2-methyl-4-nonanol, 6-undecanol, 5-ethylundecan-6-ol, 5,7-diethylundecan-6-ol, 5,7-dibutylundecan-6-ol, 9-ethyltridecan-6-ol, 5,11-diethylpentadecan-8-ol, 5-butylundecan-6-ol, and/or 5-butyl-7-ethylundecan-6-ol. In certain embodiments, the one or more compounds of Formula II may include 2-pentanol, 4-heptanol, 2-heptanol, 4-nonanol, 2-methyl-4-nonanol, and 6-undecanol. In yet other embodiments, the one or more compounds of Formula II may include 5-ethylundecan-6-ol, 5,7-diethylundecan-6-ol, 5,7-dibutylundecan-6-ol, 9-ethyltridecan-6-ol, 5,11-diethylpentadecan-8-ol, 5-butylundecan-6-ol, and 5-butyl-7-ethylundecan-6-ol.

In some embodiments, the one or more compounds of Formula II is a mixture of compounds selected from 2-pentanol, 4-heptanol, 2-heptanol, 4-nonanol, 2-methyl-4-nonanol, 6-undecanol, 5-ethylundecan-6-ol, 5,7-diethylundecan-6-ol, 5,7-dibutylundecan-6-ol, 9-ethyltridecan-6-ol, 5,11-diethylpentadecan-8-ol, 5-butylundecan-6-ol, and/or 5-butyl-7-ethylundecan-6-ol In some embodiments of method E, the method produces one or more compounds of Formula III. In certain embodiments, the one or more compounds of Formula III pentane, heptane, nonane, and undecane. In certain embodiments, the one or more compounds of Formula III may include unbranched or branched pentane, unbranched or branched heptane, unbranched or branched nonane, unbranched or branched undecane, unbranched or branched tridecane, and/or unbranched or branched pentadecane.

In some embodiments, the one or more compounds of Formula III may include pentane, heptane, nonane, 2-methyl-nonane, undecane, 5-ethylundecane, 5,7-diethyl-undecane, 5,7-dibutylundecane, 9-ethyltridecane, 5,11-diethylpentadecane, 5-butylundecane, and/or 5-butyl-7-ethyl-undecane. In certain embodiments, the one or more compounds of Formula III may include pentane, heptane, nonane, 2-methyl-nonane, undecane. In yet other embodiments, the one or more compounds of Formula I may include 5-ethylundecane, 5,7-diethylundecane, 5,7-dibutylundecane, 9-ethyltridecane, 5,11-diethylpentadecane, 5-butylundecane, and/or 5-butyl-7-ethylundecane.

In some embodiments, the one or more compounds of Formula III is a mixture of compounds selected from pentane, heptane, nonane, 2-methyl-nonane, undecane, 5-ethylundecane, 5,7-diethylundecane, 5,7-dibutylundecane, 9-ethyltridecane, 5,11-diethylpentadecane, 5-butylundecane, and/or 5-butyl-7-ethylundecane.

In another embodiment that may be combined with any of the preceding embodiments of method E, steps (a)-(d) are performed as a one-pot, multi-step process. In other embodiments of method E, a second metal-based catalyst is added to step (d) for hydrogenating, deformylating, isomerizing, hydrodeoxygenating, or catalytic reforming of the one or more compounds of Formula. In some embodiments, the second metal-based catalyst includes a metal selected from the group consisting of platinum, nickel, molybdenum, tungsten, cobalt, and combinations of these metals. In certain embodiments, the second metal-based catalyst includes platinum, nickel-molybdenum (Ni—Mo), nickel-tungsten (Ni—W), cobalt-molybdenum (Co—Mo), and combinations of these metals. In specific embodiments, the second metal-based catalyst may be Pd/C, NiO—$MoO_3$/$Al_2O_3$, Pt/$SiO_2$—$Al_2O_3$, or combinations of these catalysts.

In some embodiments, a fuel or a lubricant is produced by method E.

In some of the foregoing embodiments, the disclosed methods are performed as a "one-pot" reaction. In one embodiment, for instance, the one or more compounds of Formula I formed in the synthesis are not isolated from the reaction mixture or purified. Instead, the entire reaction mixture is used in the next step of the process, in which the one or more compounds of Formula I are converted into the corresponding alcohols or alkanes. The one-pot reaction eliminates the effort and expense of isolating the one or more compounds of Formula I. It should be understood, however, that the one or more compounds of Formula I may be isolated from the reaction mixture before continuing with the next reaction step to produce the corresponding alcohols or alkanes. In some of the foregoing embodiments, the methods are carried out in a single reaction vessel. In some of the foregoing embodiments, the one or more compounds of Formula I are used in the next step of the process without isolation or purification. In some of the foregoing embodiments, the reaction steps herein are carried out in one reaction vessel.

Another aspect of the present disclosure provides a method F of producing a mixture of alkanones, by: a) providing a fermentation product mixture that includes acetone and one or more optionally substituted alcohols; b) combining the fermentation product mixture with a metal-based catalyst in the presence of a base; and c) producing a mixture of alkanones, in which at least a portion of the alkanones in the mixture are double-alkylated. In some embodiments of method F, at least 20%, 25%, 30%, 40%, 50%, 60%, 70%, 75%, 80%, 90% or 95% of the alkanones in the mixture are double alkylated.

In certain embodiments, the method further includes separating each of the alkanones in the mixture. Each of the separated alkanones may be further converted into alcohols by hydrogenating, deformylating, isomerizing, hydrodeoxygenating, or catalytic reforming the alkanone. Each of the separated alkanones may be further converted into alkanes by hydrogenating, deformylating, isomerizing, hydrodeoxygenating, or catalytic reforming the alkanone.

In other embodiments of method F, the mixture of alkanones is a mixture of C5-C20 alkanones. In certain embodiments, at least 20%, 30%, 40%, 50%, 60%, 70%, 80%, or 90% of the mixture is C7-C20 alkanones. In certain embodiments, at least 10%, 20%, 30%, 40%, 50%, 60%, 70%, 80% or 90% of the mixture is C11-C20 alkanones.

In some embodiments that may be combined with any of the preceding embodiments of method F, the providing of the fermentation product mixture includes: providing a saccharide; contacting the saccharide with a fermentation host to produce the fermentation product mixture. In some embodiments, the saccharide may include C5 saccharides, C6 saccharides, or a mixture thereof. In certain embodiments, the saccharide may include glucose, sucrose, cellobiose and xylose, or a combination thereof. In certain embodiments, the saccharides may be derived from biomass, which may include cellulose, hemicellulose, and/or lignin. In certain embodiments, the providing of the fermentation product mixture further includes contacting the saccharide and the fermentation host with an extractant. In some embodiments, the extractant has one or more of the following properties: i) is non-toxic to fermentation host (e.g., *Clostridium*); ii) has partition coefficients for acetone and butanol equal to or greater than 1; and iii) has a partition coefficient for ethanol of less than 0.5. In other embodiments, the extractant is selected from glyceryl tributyrate, glyceryl tripropionate, oleyl alcohol, and polypropylene glycol, or a combination thereof. In yet other embodiments, the fermentation product mixture has less than about 5 wt %, about 4 wt %, about 3 wt %, about 2 wt %, or about 1 wt % water.

In some embodiments of method F, the one or more optionally substituted alcohols is one unsubstituted alcohol that may be branched or unbranched. In other embodiments, the one or more optionally substituted alcohols of the fermentation product mixture is one optionally substituted alcohol. In yet other embodiments, the one or more optionally substituted alcohols of the fermentation product mixture are two optionally substituted alcohols. In yet other embodiments, the one or more optionally substituted alcohols of the fermentation product mixture are two or more optionally substituted alcohols. In certain embodiments, the optionally substituted alcohols are C1-C14 alcohols. In other embodiments, the fermentation product mixture is made up of acetone and two or more optionally substituted C1-C8 alcohols. In yet other embodiments, the fermentation product mixture is made up of acetone and two or more optionally substituted C1-C4 alcohols. In yet other embodiments, the one or more optionally substituted alcohols of the fermentation product mixture are two optionally substituted alcohols. In yet other embodiments, the fermentation product mixture is made up of acetone, a first C1-C4 alcohol, and a second C1-C4 alcohol. In other embodiments, the fermentation product mixture is made up of acetone, butanol, and ethanol.

In certain embodiments, the acetone, butanol, and ethanol are present in the fermentation product mixture in a weight ratio of about 2-4 acetone to about 5-7 butanol to about 0.01-2 ethanol. In other embodiments, the acetone, butanol, and ethanol are present in the fermentation product mixture in a weight ratio of about 3 to about 6 to about 0.01-1. In yet other embodiments, the acetone, butanol, and ethanol are present in the fermentation product mixture in a weight ratio of about 3 to about 6 to about 1.

In some embodiments that may be combined with any of the preceding embodiments of method F, the metal-based catalyst may include nickel, ruthenium, rhodium, palladium, rhenium, iridium, platinum, copper, or combinations of these metals. In certain embodiments, the metal-based catalyst may be [Ir(COD)Cl]$_2$, RuCl$_2$(COD), PtCl$_2$(COD), [Rh(COD)Cl]$_2$, Ni/Si-Alumina, Ru/C, Rh/C, Pt/C, or Pd/C, or a combination of these metal-based catalysts. In yet other embodiments, the metal-based catalyst may include a palladium-based catalyst, such as Pd(OAc)$_2$, Pd$_2$(dba)$_3$, Pd(OH)$_2$/C, Pd/C, Pd/CaCO$_3$, Pd/Alumina, or Pd-polyethylenimines on silica, or a combination of these palladium-based catalysts.

In some embodiments that may be combined with any of the preceding embodiments of method F, the base may be K$_3$PO$_4$, KOH, Ba(OH)$_2$.8H$_2$O, K$_2$CO$_3$, KOAc, KH$_2$PO$_4$, Na$_2$HPO$_4$, pyridine, or Et$_3$N, or a combination of these bases.

In other embodiments that may be combined with any of the preceding embodiments of method F, the method further includes combining the fermentation product mixture in step (c) with a solvent. In some embodiments, the solvent is an organic solvent. In certain embodiments, the solvent may be toluene, ethyl acetate, diethylene glycol dimethyl ether, monoglyme, butanol, diethylene glycol dibutyl ether, oleyl alcohol, dibutyl phthalate, or mixtures of these solvents. In yet other embodiments, the method is performed neat.

In some embodiments that may be combined with any of the preceding embodiments of method F, the method further includes heating the reaction mixture of step (c) to a temperature sufficient to form the one or more compounds of Formula I. In certain embodiments, the temperature is between 100° C. to 200° C. In other embodiments, the temperature is between 110° C. to 180° C. In yet other embodiments, the temperature is between 110° C. to 145° C. In yet other embodiments, the temperature is between 140° C. to 220° C.

In some embodiments that may be combined with any of the preceding embodiments of method F, the alkanones of the mixture are unbranched, branched, or a mixture thereof. In some embodiments, the alkanones of the mixture are selected from unbranched or branched pentanone, unbranched or branched heptanone, unbranched or branched nonanone, unbranched or branched undecanone, unbranched or branched tridecanone, and/or unbranched or branched pentadecanone. In other embodiments, the alkanones of the mixture are selected from unbranched or branched pentanone, unbranched or branched heptanone, unbranched or branched nonanone, and unbranched or branched undecanone, or a combination thereof. In yet other embodiments, the alkanones of the mixture are selected from unbranched or branched undecanone, unbranched or branched tridecanone, and/or unbranched or branched pentadecanone. In certain embodiments, the alkanones of the mixture are selected from 2-pentanone, 4-heptanone, 2-heptanone, 4-nonanone, 2-methyl-4-nonanone, 6-undecanone, 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and 5-butyl-7-ethylundecan-6-one. In other embodiments, the alkanones of the mixture are selected from 2-pentanone, 4-heptanone, 2-heptanone, 4-nonanone, 2-methyl-4-nonanone, and 6-undecanone. In yet other embodiments, the alkanones of the mixture are selected from 5-ethylundecan-6-one, 5,7-diethylundecan-6-one, 5,7-dibutylundecan-6-one, 9-ethyltridecan-6-one, 5,11-diethylpentadecan-8-one, 5-butylundecan-6-one, and 5-butyl-7-ethylundecan-6-one.

In other embodiments that may be combined with any of the preceding embodiments of method F, one or more alkanones of the mixture may serve as one or more precursors for fuel additives.

In another embodiment that may be combined with any of the preceding embodiments of method F, steps (a)-(c) are performed as a one-pot, multi-step process. In other embodiments of method F, a second metal-based catalyst is added to the mixture of alkanones step (c) for hydrogenating, deformylating, isomerizing, hydrodeoxygenating, or catalytic reforming of one of more alkanoates of the mixture. In some embodiments, the second metal-based catalyst includes a metal selected from the group consisting of platinum, nickel, molybdenum, tungsten, cobalt, and combinations of these metals. In certain embodiments, the second metal-based catalyst includes platinum, nickel-molybdenum (Ni—Mo), nickel-tungsten (Ni—W), cobalt-molybdenum (Co—Mo), and combinations of these metals. In specific embodiments, the second metal-based catalyst may be Pd/C, NiO—MoO$_3$/Al$_2$O$_3$, or Pt/SiO$_2$—Al$_2$O$_3$, or a combination of these catalysts.

In some embodiments, a fuel or a lubricant is produced by method F.

In another aspect, provided is a method of producing a mixture of alcohols suitable for use as a fuel or a lubricant, by: a) preparing the mixture of alkanones according to the method F; and b) converting the mixture of alkanones into a mixture of alcohols by hydrogenating, deformylating, isomerizing, hydrodeoxygenating, or catalytic reforming the mixture of alkanones.

In certain embodiments, the mixture of alcohols is selected from pentanol, heptanol, nonanol, and undecanol. In certain embodiments, the mixture of alcohols is selected from unbranched or branched pentanol, unbranched or branched heptanol, unbranched or branched nonanol, unbranched or branched undecanol, unbranched or branched tridecanol, and/or unbranched or branched pentadecanol. In some embodiments, the mixture of alcohols is selected from 2-pentanol, 4-heptanol, 2-heptanol, 4-nonanol, 2-methyl-4-nonanol, 6-undecanol, 5-ethylundecan-6-ol, 5,7-diethylundecan-6-ol, 5,7-dibutylundecan-6-ol, 9-ethyltridecan-6-ol, 5,11-diethylpentadecan-8-ol, 5-butylundecan-6-ol, and/or 5-butyl-7-ethylundecan-6-ol. In other embodiments, the mixture of alcohols is selected from 2-pentanol, 4-heptanol, 2-heptanol, 4-nonanol, 2-methyl-4-nonanol, and 6-undecanol. In yet other embodiments, the mixture of alcohols is selected from 5-ethylundecan-6-ol, 5,7-diethylundecan-6-ol, 5,7-dibutylundecan-6-ol, 9-ethyltridecan-6-ol, 5,11-diethylpentadecan-8-ol, 5-butylundecan-6-ol, and 5-butyl-7-ethylundecan-6-ol.

In yet another aspect, provided is a method of producing a mixture of alkanes suitable for use as a fuel or a lubricant, by: a) preparing the mixture of alkanones according to the method F; and b) converting the mixture of alkanones into a mixture of alkanes by hydrogenating, deformylating, isomerizing, hydrodeoxygenating, or catalytic reforming the mixture of alkanones.

In certain embodiments, the mixture of alkanes is selected from pentane, heptane, nonane, and undecane. In certain embodiments, the mixture of alkanes is selected from unbranched or branched pentane, unbranched or branched heptane, unbranched or branched nonane, unbranched or branched undecane, unbranched or branched tridecane, and/or unbranched or branched pentadecane. In some embodiments, the mixture of alkanes is selected from pentane, heptane, nonane, 2-methyl-nonane, undecane, 5-ethylundecane, 5,7-diethylundecane, 5,7-dibutylundecane, 9-ethyltridecane, 5,11-diethylpentadecane, 5-butylundecane, and/or 5-butyl-7-ethylundecane. In yet other embodiments, the mixture of alkanes is selected from pentane, heptane, nonane, 2-methyl-nonane, undecane. In yet other embodiments, the mixture of alkanes is selected from 5-ethylundecane, 5,7-diethylundecane, 5,7-dibutylundecane, 9-ethyltridecane, 5,11-diethylpentadecane, 5-butylundecane, and/or 5-butyl-7-ethylundecane.

DESCRIPTION OF THE FIGURES

The present application can be understood by reference to the following description taken in conjunction with the accompanying drawing figures, in which like parts may be referred to by like numerals.

DETAILED DESCRIPTION

Figure 1:
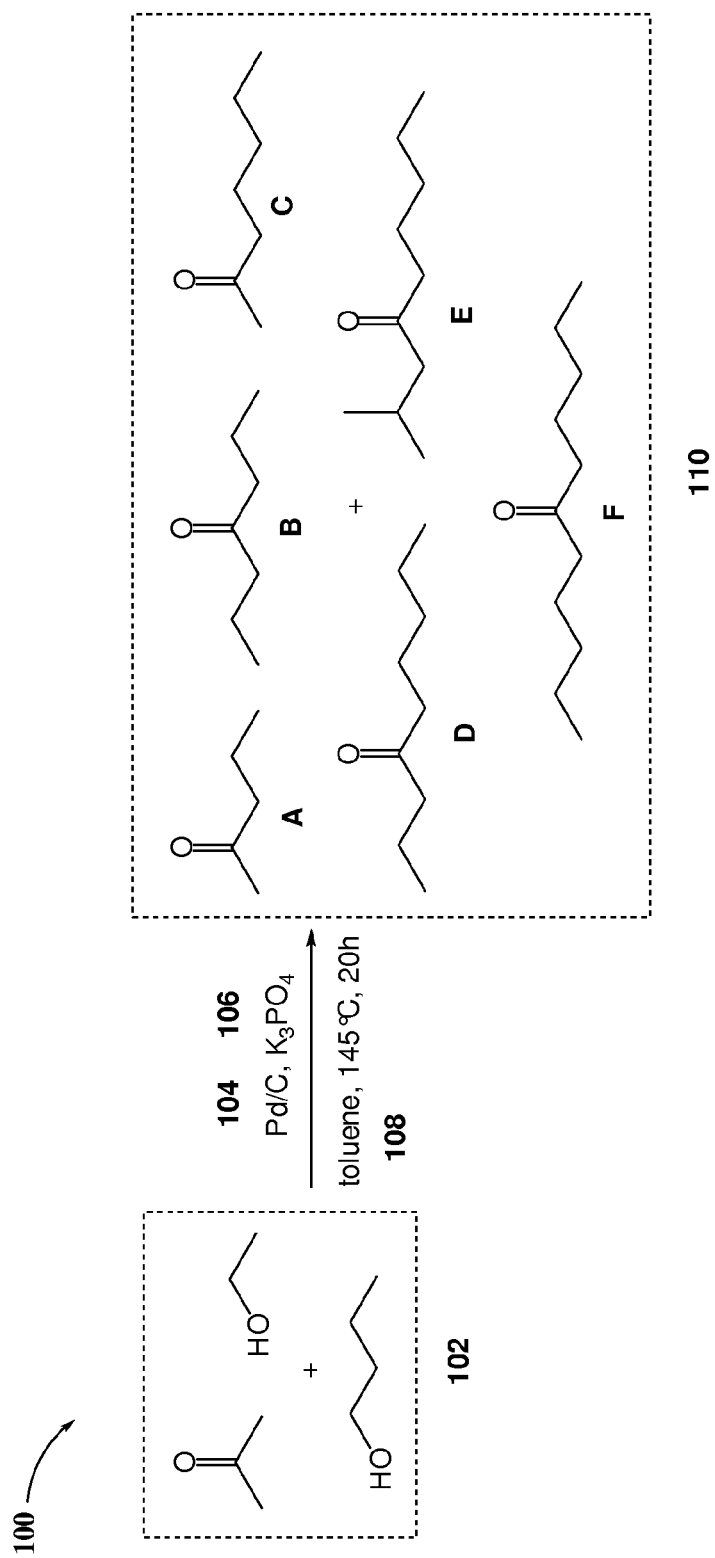
FIG. 1 depicts one exemplary reaction for producing C5-C11 ketones from an ABE-mixture using a palladium-on-carbon (Pd/C) catalyst.

The following description sets forth numerous exemplary configurations, processes, parameters, and the like. It should be recognized, however, that such description is not intended as a limitation on the scope of the present disclosure, but is instead provided as a description of exemplary embodiments.

As used herein, "fuel" refers to a composition made up of a compound containing at least one carbon-hydrogen bond, which produces heat and power when burned. Fuel may be produced using plant-derived biomass as a feedstock, for example from the lignin biopolymer of lignocellulose. Fuel may also contain more than one type of compound, and includes mixtures of compounds. As used herein, the term "transportation fuel" refers to a fuel that is suitable for use as a power source for transportation vehicles.

As used herein, the terms "alkyl," "alkenyl" and "alkynyl" include straight-chain and branched-chain monovalent hydrocarbyl radicals, and combinations of these, which contain only C and H when they are unsubstituted. Examples include methyl, ethyl, propyl, isopropyl, butyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as for example C1-C6, represent the sum of the number of carbon atoms in the group plus the number of such heteroatoms that are included as replacements for carbon atoms in the ring or chain being described.

Alkyl, alkenyl and alkynyl groups are often substituted to the extent that such substitution makes sense chemically. Typical substituents may include, for example, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C3-C8 heterocyclyl, C4-C10 heterocyclylalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', NR'$_2$, SR', $SO_2R'$, $SO_2NR'_2$, NR'$SO_2R'$, NR'CONR'$_2$, NR'COOR', NR'COR', CN, COOR', CONR'$_2$, OOCR', COR', and $NO_2$, wherein each R' is independently H, C1-C8 alkyl, C2-C8 heteroalkyl, C3-C8 heterocyclyl, C4-C10 heterocyclylalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two R or R' groups on the same or adjacent atoms (e.g., —NR$_2$, or —NR—C(O)R), the two R or R' groups can optionally be taken together with the atoms in the substituent group to which the are attached to form a ring having 5-8 ring members, which can be substituted as allowed for the R or R' itself, and can contain an additional heteroatom (N, O or S) as a ring member.

"Alkanone" refers to a ketone compound in a linear or branched arrangement. Examples of alkanones include pentanone, heptanone, heptanone, nonanone, and undecanone. In certain embodiments, the alkanones have a linear arrangement, such as 2-pentanone, 4-heptanone, 2-heptanone, 4-nonanone, and 6-undecanone. In other embodiments, the alkanones have a branched arrangement, such as 2-methyl-4-nonanone. Preferred alkanones include those with at least five carbons (C5+ alkanones), at least seven carbons (C7+ alkanones), at least nine carbons (C9+ alkanones), or at least (C11+ alkanones), or between five and twenty carbons (C5-C20 alkanones), between seven and twenty carbons (C7-C20 alkanones), or between eleven and twenty carbons (C11-C20 alkanones). In other embodiments, the alkanone may be substituted with substitutents that are suitable for the alkyl group as described above.

"Heteroalkyl," "heteroalkenyl," and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

"Cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Examples of cycloalkyl substitutents may include cyclopropyl, cyclobutyl, cyclopentyl, cyclohexyl, adamantyl, and decahydronaphthalenyl. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

"Arylalkyl" groups as used herein are hydrocarbyl groups, and may be described by the total number of carbon atoms in the ring and alkylene or similar linker. Thus, a benzyl group is a C7-arylalkyl group, and phenylethyl is a C8-arylalkyl.

"Heteroarylalkyl" as described above refers to a moiety that includes an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

In general, any alkyl, cycloalkyl, alkenyl, alkynyl, aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Halo," as used herein includes fluoro, chloro, bromo, and iodo.

"Amino" as used herein refers to $NH_2$, but where an amino is described as "substituted" or "optionally substituted," the term includes NR'R" wherein each R' and R" may independently be H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, "primary alcohol" refers to an alcohol where the carbon carrying the —OH group is only attached to one alkyl group. Examples of primary alcohols may include methanol, ethanol, 1-propanol, 2-methyl-1-propanol, butanol, and pentanol. As used herein, "secondary alcohol" refers to an alcohol where the carbon carrying the —OH group is attached to two alkyl groups. Examples of secondary alcohols may include 2-propanol, and cyclohexanol. As used herein, "tertiary alcohol" refers to an alcohol where the carbon carrying the —OH group is attached to three alkyl groups. Examples of tertiary alcohols may include 2-methyl-2-butanol.

As used herein, the term "yield" refers to the total amount of product relative to the amount of ketone present in the fermentation product mixture. For example, with reference to FIG. 1, the overall reaction yield refers to the combined molar yields of products A-F, calculated with respect to the molar amount of acetone present as a starting material in the fermentation product mixture.

As used herein, the term "about" refers to an approximation of a stated value within an acceptable range. Preferably, the range is +/−10% of the stated value.

The following description relates to a process for converting a fermentation product mixture produced from biomass-derived sugars (e.g., glucose, sucrose, cellobiose, xylose) into fuels employing metal-catalyzed alkylation. With reference to FIG. 1, reaction 100 is an exemplary embodiment for producing C5-C11 ketones suitable for use in fuels. Starting materials 102 is an acetone-butanol-ethanol (ABE) mixture, produced by fermentation of biomass-derived sugars using Clostridia bacteria. This fermentation process produces an ABE mixture in a mass ratio of 3:6:1, respectively (or a molar ratio of 2.3:3.7:1). The acetone in the ABE mixture undergoes mono- and double-alkylation in the presence of metal-based catalyst 104 (i.e., Pd/C) and base 106 (i.e., $K_3PO_4$) in solvent 108 (i.e., toluene), at a reaction temperature of 145° C. over 20 hours. These reaction conditions yield products 110, which includes 2-pentanone (A), 4-heptanone (B), 2-heptanone (C), 4-nonanone (D), 2-methyl-4-nonanone (E), and 6-undecanone (F). Among these products, B, D and F are produced by double-alkylation of acetone.

Under the reactions conditions described herein, in some preferred embodiments, the formation of one or more Guerbet products (e.g., aldehydes) in the product mixture is minimized. In certain preferred embodiments, ketone alkyation predominates, which yields a higher proportion of double-alkylated compounds in the product mixture. The reaction conditions described herein allow for greater kinetic control of the alkylation reaction to produce higher molecular weight ketones that are suitable for jet and diesel fuel compounds (e.g., C5-C20 alkanones).

The process described herein employs various components, including a fermentation product mixture obtained from a fermentation process, a metal-based catalyst, a base, and solvent, to carry out the alkylation of a ketone, such as acetone, in the presence of two or more alcohols to produce one or more products suitable for use as fuels and other chemicals.

The Fermentation Product Mixture

The fermentation product mixture described herein may be derived from renewable sources, such as biomass. In some embodiments, the biomass is first converted into sugars, which is then used as the feedstock to produce the fermentation product mixture. Sugars suitable for use as feedstock to produce the fermentation product mixture may include, for example, monosaccharides, disaccharides, or oligosaccharides. In certain embodiments, the sugars may include any C5 saccharides or C6 saccharides, or a combination of C5 and C6 saccharides. In other embodiments, the sugars may include arabinose, lyxose, ribose, xylose, ribulose, xylulose, allose, altrose, glucose, sucrose, cellobiose, mannose, gulose, idose, galactose, talose, psicose, fructose, sorbose, or tagatose, or a mixture thereof. In one embodiment, the sugars may include glucose, sucrose or xylose, or a mixture thereof. In another embodiment, the sugars may include glucose or sucrose, or a mixture thereof. Any methods known in the art may be employed to produce sugars from the biomass. For example, the biomass may undergo pretreatment processes known in the art to more effectively liberate sugars from the biomass. The biomass is typically made up of organic compounds that are relatively high in oxygen, such as carbohydrates, and may also contain a wide variety of other organic compounds. In some embodiments, the biomass is made up of cellulose, hemicellulose, and/or lignin.

It should be understood, however, that in other embodiments, the sugars used as feedstock in the fermentation process may be derived from non-renewable sources, or from both renewable and non-renewable sources.

The fermentation product mixture may include a ketone and one or more alcohols. In certain embodiments, the fermentation product mixture may include a ketone and one alcohol, or a ketone and two alcohols. In certain embodiments, the ketone is acetone. The fermentation product mixture may be an ABE mixture produced by fermenting sugars using any host capable of producing hydrocarbons (e.g., ethanol and heavier hydrocarbons). For example in some embodiments, the fermentation host is bacteria from the Clostridia family (e.g., *Clostridium acetobutylicum*, *Clostridium beijerinckii*). Clostridia bacteria have the ability to convert biomass-derived carbohydrates into an ABE mixture from both hexoses and pentoses. It should be understood, however, that any fermentation host capable of converting sugars into a mixture of a ketone and one or more alcohols may be employed to provide the starting materials for the process described herein.

In some embodiments, the fermentation product mixture may be used without further purification or isolation steps after the fermentation process. In other embodiments, the fermentation product mixture is isolated after the fermentation process. Any techniques known in the art may be used to isolate the fermentation product mixture (e.g., ABE mixture) after the fermentation process.

While an ABE mixture is used as the starting materials in reaction 100, the starting materials used in the process described herein are not limited to butanol and ethanol as the alcohols. The alcohols may be any length. In some embodiments, the fermentation product mixture may include primary alcohols including, for example, methanol, ethanol, propanol, 2-methylpropan-1-ol, butanol, pentanol, and 2-ethyl-1-hexanol.

While the ABE mixture in reaction 100 has a mass ratio of 3:6:1, the ratio of acetone to the two or more primary alcohols may vary. For example, the fermentation process may be optimized to reduce the amount of ethanol produced, so as to maximize butanol yields.

Additional ketones and alcohols may be added to the fermentation product mixture to vary the range of molecular weights and structures obtained from the process described herein. In some embodiments, these additional ketones and alcohols may be added to the fermentation product mixture before use in the reaction with the catalyst and base. In other embodiments, these additional ketones and alcohols may be added during the reaction. These additions to the fermentation product mixture may be useful for improving the product properties for specific applications, such as biodiesel or lubricants. The alcohols and ketones added to the fermentation product mixture may be saturated or unsaturated. For example, oleyl alcohol may be added to the fermentation product mixture to adjust the molecular weight of the products produced by the methods described herein for use as lubricants.

The fermentation product mixture may also include bio-derived ketones through ketonization of volatile fatty acids. For example, acetic acid may be ketonized via fermentation to form acetone, which can be converted into a mix of higher ketones using the methods described herein to produce gasoline and gasoline precursors. Propionic acid may also be ketonized via fermentation to form 3-pentanone, which can be converted into a mix of higher ketones using the methods described herein to produce gasoline and gasoline precursors.

Further, in some embodiments, an extractant may also be used to selectively extract the fermentation product mixture from the aqueous phase into an organic (water immiscible) phase. In some embodiments, an extractant is a chemical used to recover certain products from the fermentation broth. For example, in one embodiment, an extractant is a chemical used to recover acetone and butanol from the fermentation broth. Suitable extractants may include tributyrin (also known as glyceryl tributyrate), oleyl alcohol, polypropylene glycol (of varying molecular weights), or mixtures of these extractants. In some embodiments, the extractant does not inhibit the growth of the microorganism producing the fermentation product mixture, or decrease the rate of formation of the fermentation products. In certain embodiments, the extractant can be chosen from a class of materials that are (a) not inhibitory to microorganisms (b) have very low solubility in water, and (c) have very low water solubility, referring to the amount of water that can be dissolved in the extractant.

In certain embodiments, in situ extraction may be conducted during the fermentation, and can reduce the inhibitory effect of some of products generated from the fermentation process. For example, the fermentation process described above may yield metabolites, which have inherent toxicity that may affect the catalysis of the alkylation reaction under aqueous conditions. The use of a selective, non-toxic, water-immiscible extractant can remove in situ inhibitory metabolites produced during fermentation. Removal of such inhibitory products can increase solvent titers and yields, lower distillation costs, and reduce water usage and reactor sizes. When used during fermentation, the extractant employed should be non-inhibitory.

In other embodiments, an extractant may be used on the fermentation product mixture after fermentation has taken place to selectively extract certain components of the fermentation product mixture from the aqueous phase into the organic phase. For example, in one embodiment, an extractant such as tributyrin may be used on the fermentation product mixture to relative amounts of acetone and butanol in the fermentation product mixture used in the alkylation reactions described herein. Such fermentation products can be recovered from the extractant by distillation. When the boiling points of the extractants employed are much higher than those of the fermentation products, the energy requirements for distillation can be reduced. Since the extractants have very little solubility for water, almost no water is present in the extractant, leaving primarily the fermentation products.

Thus, in some embodiments, an extractant can selectively separate acetone and butanol from an ABE mixture in ratios suitable for subsequent alkylation reactions to yield fuel products, and minimize the amount of ethanol extracted. Minimizing the amount of ethanol in the ABE mixture undergoing alkyation may, in some instances, be desirable for controlling the molecular weight of the products, such as for producing longer chained products. The addition of an extractant to the fermentation culture may, in certain embodiments, reduce the formation the Guerbet product. In certain embodiments, the addition of an extractant to the fermentation culture produces at least 40%, 50%, 60%, 70%, 80% or 90% double-alkylated products.

The use of an extractant, in certain embodiments, affords simultaneous removal of residual inhibitors and the desired product during biofuel fermentation, a key advantage over existing recovery technologies.

Other techniques known in the art may be used to selectively separate ketones and alcohols from a fermentation mixture (e.g., acetone and butanol from an ABE mixture) for subsequent alkylation reactions to yield fuel products. For example, pervaporation is a membrane separation technique that can be utilized to separate liquid mixtures through a membrane via a solution-diffusion mechanism. First, permeation through the membrane takes place, and then the permeate is collected as a vapor on the other side of the membrane. The evaporation of the permeate on the permeate side of the membrane creates the driving force for the transfer of the permeate. The pervaporation membrane behaves as a selective barrier between the feed and the permeate; therefore, the selection of the pervaporation membrane is crucial to achieve high selectivity and fluxes. The permeability of the components through the membrane is the multiplication of their diffusion and solubility in the membrane material. For instance, for pervaporation of alcohol-water mixtures, the diffusivity of water is greater than the diffusivity of the alcohol due to the smaller dimension of the water molecule. Therefore, a membrane material with higher alcohol solubility should be selected to obtain high alcohol permselectivity. Polydimethylsiloxane (PDMS) is well known as a membrane material for ethanol separation from dilute aqueous ethanol mixture due to its hydrophobic nature and high free volume which allows excellent selectivity and high fluxes.

Thus, in some embodiments, the methods described herein further include providing a pervaporation membrane, and contacting the fermentation product mixture with the pervaporation membrane to selectively separate the ketone and certain alcohols. In one embodiment, the pervaporation membrane is PDMS. In another embodiment, the pervaporation membrane is a poly(styrene-b-dialkylsiloxane-b-styrene) triblock copolymer that has a polydialkylsiloxane block and polystyrene end blocks. In certain embodiments, the triblock copolymer has a molecular weight in the range of about 110 kg/mol to about 1000 kg/mol. In other embodiments, the triblock copolymer has a molecular weight in the range of about 110 kg/mol to about 500 kg/mol. In some embodiments, the triblock copolymer has a molecular weight in the range of about 120 kg/mol to about 300 kg/mol. In some embodiments, the triblock copolymer has a molecular weight in the range of about 130 kg/mol to about 300 kg/mol. In some embodiments, the triblock copolymer has a morphology, and wherein the morphology is a cylindrical, lamellar, double diamond, or gyroid morphology. In some embodiments, the triblock copolymer has a morphology, and wherein the morphology is a cylindrical or lamellar morphology. In some embodiments, the triblock copolymer has a morphology, and wherein the morphology is a cylindrical morphology. In some embodiments, the triblock copolymer has a domain spacing (d), and wherein the domain spacing is in the range of about 20 to about 90 nanometers.

In some embodiments, the triblock copolymer loses about 5% of weight at a temperature in the range of about 290° C. to about 350° C. In some embodiments, the polydialkylsiloxane is polydimethylsiloxane. In some embodiments, the polydialkylsiloxane block has a volume fraction of about 0.6 to about 0.95 relative to the polystyrene end blocks.

The Metal-Based Catalyst

While Pd/C is employed as metal-based catalyst 104 in reaction 100, any metal-based catalyst that can catalyze the alkylation of a ketone, while reducing the oligomerization of the ketone and formation the Guerbet product, may be employed in the process described herein. In other embodiments, any metal-based catalyst that can catalyze the double alkylation of acetone, while reducing the oligomerization of acetone and formation the Guerbet product, may be employed in the process described herein. For example, the metal-based catalyst may include transition metals such as nickel, ruthenium, rhodium, palladium, rhenium, iridium, or platinum. In other embodiments, the metal-based catalyst includes palladium or platinum. In certain embodiments, the metal-based catalyst is [Ir(COD)Cl]$_2$, RuCl$_2$(COD), PtCl$_2$(COD), [Rh(COD)Cl]$_2$, Ni/Si-Alumina, Ru/C, Rh/C, Pt/C, or Pd/C.

In yet other embodiments, the metal-based catalyst is a palladium-based catalyst. Palladium-based catalysts may include palladium metal, and complexes of suitable ligands including those containing P and/or N atoms for coordinating to the palladium atoms, and other simple palladium salts either in the presence or absence of ligands. Palladium-based catalysts may also include palladium and palladium complexes supported or tethered on solid supports, such as palladium on carbon (Pd/C), as well as palladium black, palladium clusters, or palladium clusters containing other metals. Suitable examples of palladium-based catalysts may include Pd(OAc)$_2$, Pd$_2$(dba)$_3$, Pd(OH)$_2$/C, Pd/C, Pd/CaCO$_3$, Pd/Alumina, and Pd-polyethylenimines on silica.

The metal-based catalyst may be recycled in the methods described herein. For example, additional fermentation product mixture (e.g., ABE mix) may be added to the reaction vessel to further increase the overall product yield.

The Base

While K$_3$PO$_4$ is employed as base 106 in reaction 100, any base that promotes alkylation of the ketone may be used. In certain embodiments, any base that promotes double alkylation of acetone. In other embodiments, the base may also promote the reduction of the oligomerization of the ketone and formation the Guerbet product.

Suitable bases may include inorganic bases (e.g., hydroxides of alkali metals and alkaline earth metals), and organic bases. Examples of inorganic bases may include potassium hydroxide, barium hydroxide, cesium hydroxide, sodium hydroxide, strontium hydroxide, calcium hydroxide, lithium hydroxide, rubidium hydroxide, magnesium hydroxide. Examples of organic bases may include triethylamine, trimethylamine, pyridine, and methyl amine. In some embodiments, the base is KOH, Ba(OH)$_2$·8H$_2$O, K$_2$CO$_3$, KOAc, KH$_2$PO$_4$, Na$_2$HPO$_4$, pyridine, or Et$_3$N.

The type of base used may be determined by the desired strength of the base and its ability to promote alkylation of a ketone, without producing undesirable side reactions or side products. The amount of base selected may affect the overall reaction yield, and the proportion of alkylated products. In certain embodiments, the type of base used may be determined by the desired strength of the base and its ability to promote double alkylation of acetone, without producing undesirable side reactions or side products. The amount of base selected may affect the overall reaction yield, and the proportion of double-alkylated products. For example, increasing the amount of base increases the overall reaction yield, as well as the selectivity for double-alkylation. In some embodiments, at least 0.3 mole equivalents of base are used. In other embodiments, between 0.32 to 1.3 mole equivalents of base are used. In yet other embodiments, between 0.9 to 1.5 mole equivalents of base are used. In yet other embodiments, between 0.95 to 1.3 mole equivalents of base are used. In certain embodiments, 0.95 mole equivalents of base are used.

In yet other embodiments, the base used may be calcined. In such embodiments, the base can be pretreated at a high temperature to obtain a more active material. For example, in one embodiment where K$_3$PO$_4$ is the base used, the K$_3$PO$_4$ may be heated at about 600° C. to obtain a material that is more active in promoting the alkylation reaction described herein.

The Solvent

While toluene is employed as solvent 108 in reaction 100, it should be recognized that in some embodiments, the reaction may be performed neat, i.e., without addition of a solvent. In other embodiments, the reaction may be performed with a solvent. Any solvent that promotes alkylation of the ketone may be employed in the process described herein. In certain embodiments, any solvent that promotes double alkylation of acetone may be employed in the process described herein. For example, the solvent may be an organic solvent. Organic solvents may include hydrocarbons (e.g., toluene, benzene), ketones (e.g., acetone or methyl ethyl ketone), acetates (e.g., ethyl acetate or isopropylacetate), nitriles (e.g., acetonitrile), alcohols (e.g., butanol, ethanol, isopropanol), or ethers (e.g., diglyme, monoglyme, diglybu, THF). As used herein, "diglyme" refers to diethylene glycol dimethyl ether. As used herein, "diglybu" refers to diethylene glycol dibutyl ether.

A suitable solvent employed in the process described herein is one that may be used in the fermentation process, may be used in the extraction of the fermentation product mixture from the fermentation process, or may be blended directly with the products from the fermentation process. Other considerations include the promotion of the reaction rate, the formation of the reaction products, and the reduction of the Guerbet product and oligomerization of the ketone (e.g., acetone). In some embodiments, the solvent may include toluene, ethyl acetate, diglyme, monoglyme, butanol, diglybu, oleyl alcohol, dibutyl phthalate, or mixtures of these solvents.

The Reaction Conditions a) Reaction temperature

While the mixture in reaction 100 was heated to 145° C., the temperature to which the reaction mixture is heated may vary. In some embodiments, the reaction mixture is heated to reflux. In other embodiments, the reaction mixture is heated to a temperature suitable to increase selectivity for double-alkylated products.

The preferred temperature range may vary depending on the solvent, base, and catalyst used. For example, in a reaction mixture with toluene as the solvent, the preferred reaction temperature range is between about 110° C. to 145° C. In other embodiments, the reaction temperature range may increased to between, for example, 140° C. and 180° C. to increase selectivity for double-alkylated products.

b) Reaction Time

While the mixture in reaction 100 was reacted for 20 hours, the time of the reaction will also vary with the reaction conditions and desired yield. In some embodiments, the reaction time is determined by the rate of conversion of the starting material. In other embodiments, the reaction time is determined by the rate of double-alkylation of the starting material. In other embodiments, the reaction mixture is heated for 10 to 30 hours. In other embodiments, the reaction mixture is heated for 10 to 20 hours. In yet other embodiments, the reaction mixture is heated for 1 to 10 hours. In yet other embodiments, the reaction mixture is heated for 5 to 10 hours.

Further, it should be understood that the reaction can be tuned to produce gasoline versus jet/diesel products. In some embodiments, gasoline products may include the shorter-chained products, such as 2-pentanone, 4-heptanone, and 2-heptanone. In other embodiments, jet/diesel products may include the heavier-chained products, such as 4-nonanone, 2-methyl-4-nonanone, and 6-undecanone.

Figure 6A:
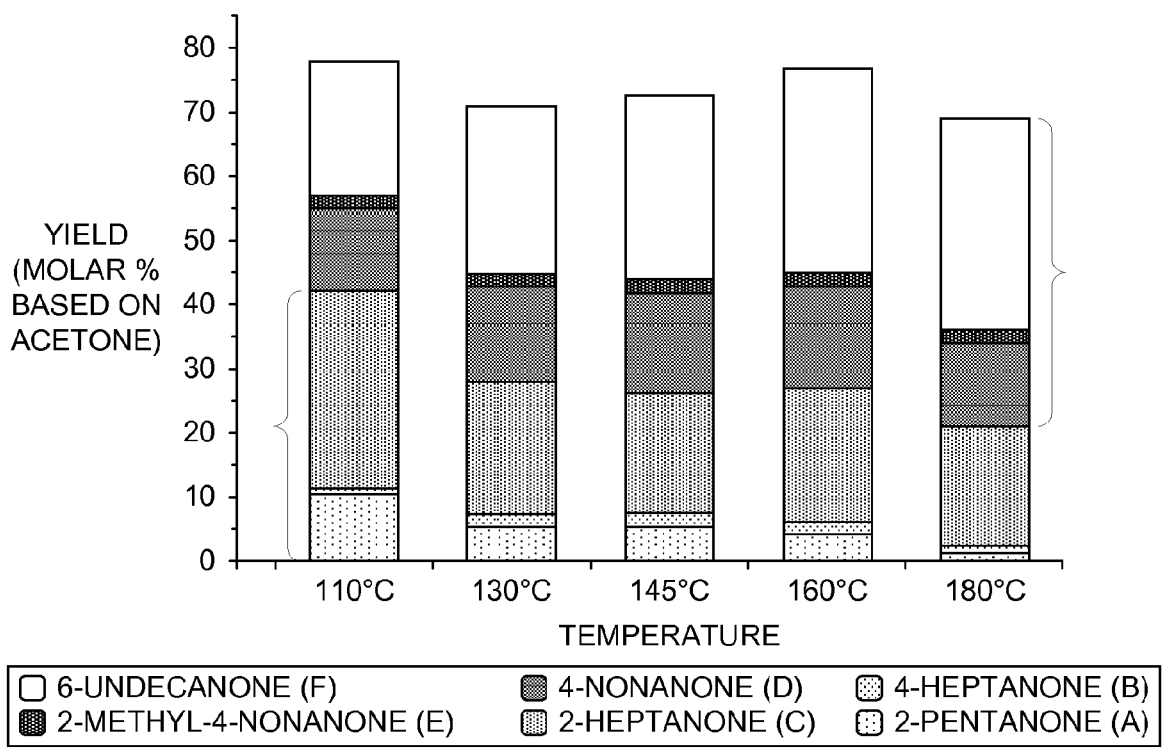
FIGS. 6A and 6B are graphs depicting the yield of A-F products from varying the temperature and the amount of base, respectively, in the alkylation of acetone in ABE mix.
Figure 6B:
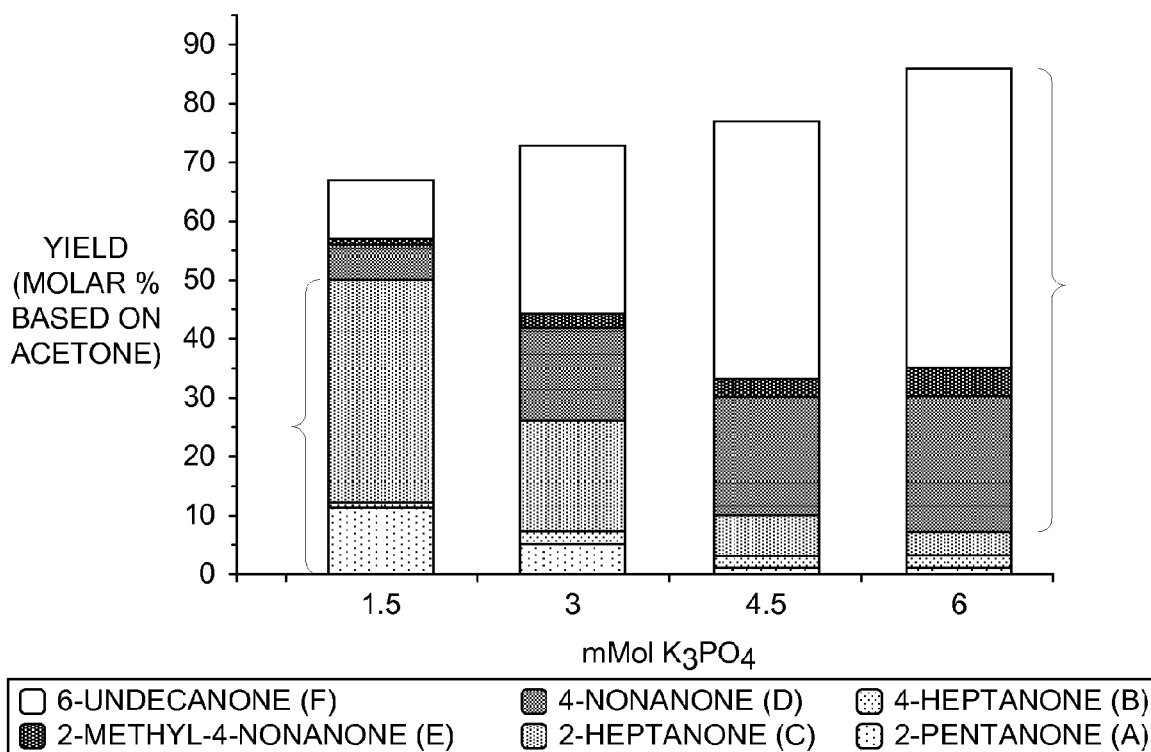
Figure 7:
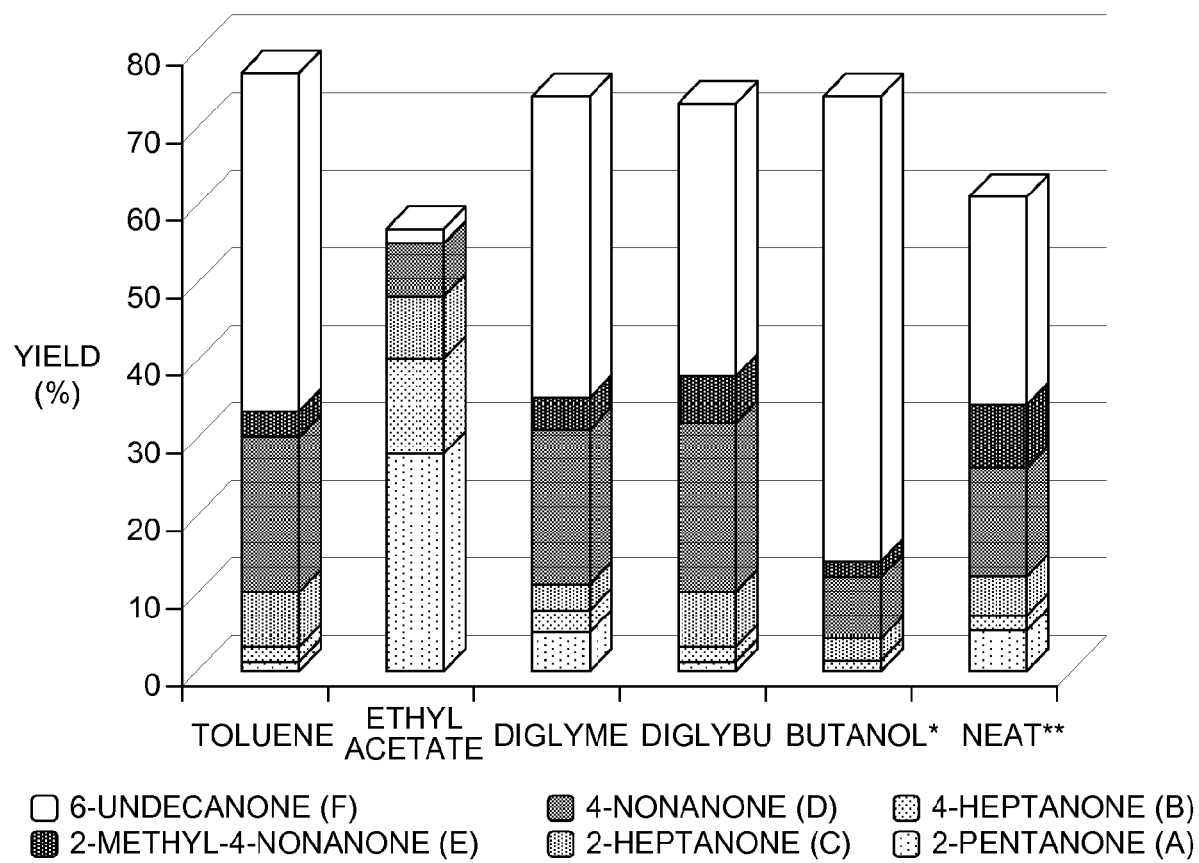
FIG. 7 is a graph depicting the yield of A-F products from varying the solvent in the alkylation of acetone in ABE mix.
Figure 17:
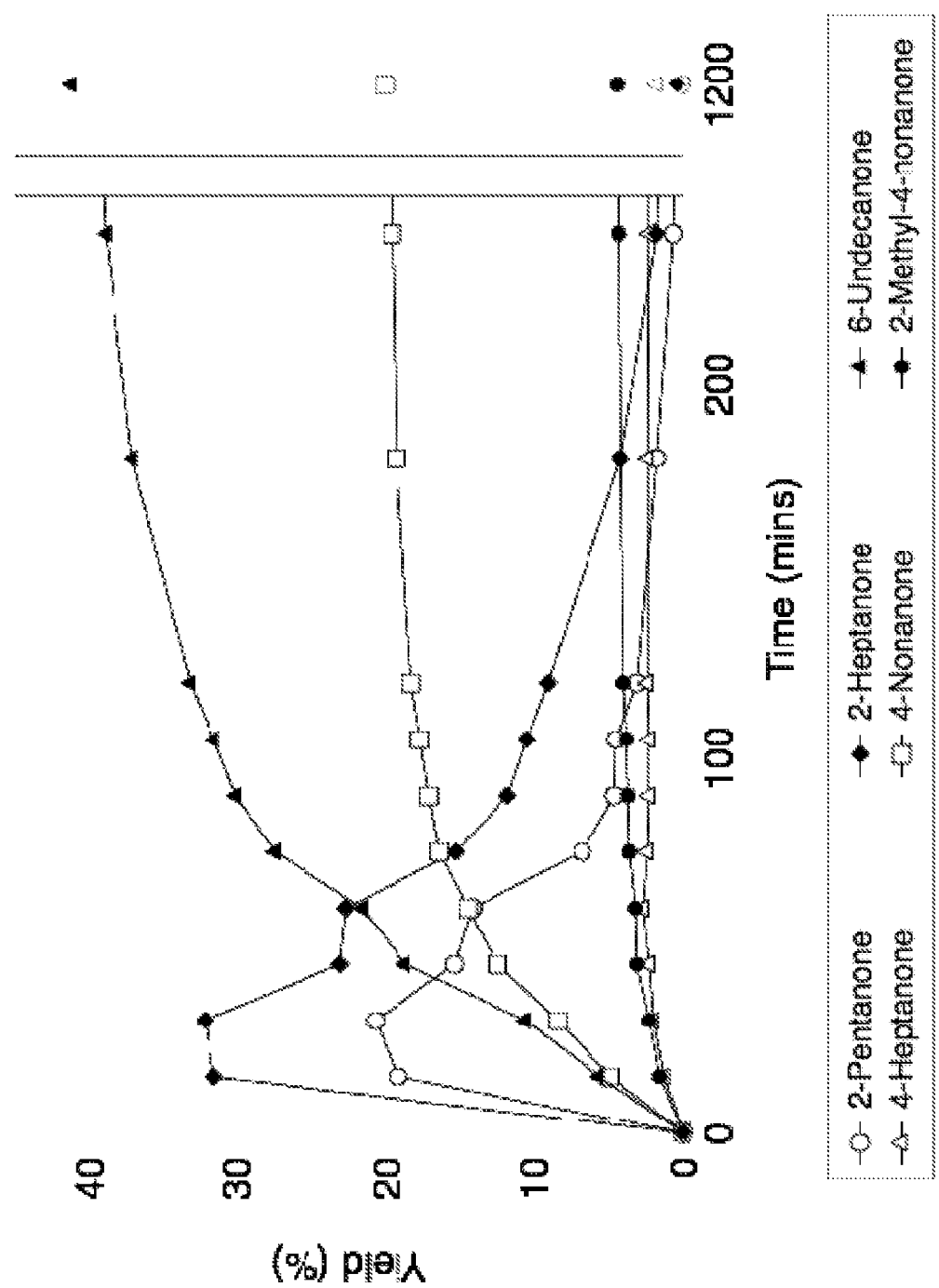
FIG. 17 is a graph that shows the product distribution over time during an exemplary palladium-catalyzed alkylation reaction of an ABE mixture, where "o" 2-pentanone, "Δ" 4-heptanone, "+" 2-heptanone, "□" 4-nonanone, "•" 2-methyl-4-nonanone, "▮" 6-undecanone.

With reference to FIGS. 6A, 6B and 17, in some embodiments, gasoline products may be produced at lower temperatures, lower base loadings and shorter reaction times. In some embodiments, gasoline products may be produced at higher yields relative to jet/diesel products when one or more of the following conditions occur: (a) temperature is between 90° C. and 170° C.; (b) between 1 and 3 mole equivalents of base are used; and (c) the reaction mixture is heated for less than about 90 minutes. In other embodiments, gasoline products may be produced at higher yields relative to jet/diesel products when one or more of the following conditions occur: (a) temperature is between 100° C. and 120° C.; (b) between 1.2 and 1.7 mole equivalents of base are used; and (c) the reaction mixture is heated for less than about 60 minutes. In yet other embodiments, gasoline products may be produced at higher yields relative to jet/diesel products when one or more of the following conditions occur: (a) temperature is about 110° C.; (b) about 1.5 mole equivalents of base are used; and (c) the reaction mixture is heated for between 10 to 60 minutes. In some embodiments, two or more of the conditions may occur to produce gasoline products at higher yields relative to jet/diesel fuel products. In other embodiments, all three conditions may occur to produce gasoline products at higher yields relative to jet/diesel products.

Further, it should be understood that, in other embodiments, jet/fuel products may be produced at higher temperatures, higher base loadings and longer reaction times. In some embodiments, jet/diesel products may be produced at higher yields relative to gasoline products when one or more of the following conditions occur: (a) temperature is above 170° C.; (b) between 3 and 9 mole equivalents of base are used; and (c) the reaction mixture is heated for greater than about 90 minutes. In other embodiments, jet/diesel products may be produced at higher yields relative to gasoline products when one or more of the following conditions occur: (a) temperature is between 180° C. and 240° C.; (b) between 4.5 and 6 mole equivalents of base are used; and (c) the reaction mixture is heated for between 2 and 25 hours. In yet other embodiments, jet/diesel products may be produced at higher yields relative to gasoline products when one or more of the following conditions occur: (a) temperature is about 180° C.; (b) about 6 mole equivalents of base are used; and (c) the reaction mixture is heated for between 90 to 200 minutes. In some embodiments, two or more of the conditions may occur to produce jet/diesel products at higher yields relative to gasoline products. In other embodiments, all three conditions may occur to produce jet/diesel products at higher yields relative to gasoline products.

The Ketones and their Uses

The reaction conditions described herein allows for greater control of the molecular weight of the ketones (e.g., alkanones) produced. In certain embodiments, the reaction conditions yields alkanones with molecular weights suitable for use as fuels Alkanones suitable for use as fuels may include those with at least 5 carbons, at least 7 carbons, or at least 11 carbons. In certain embodiments, the alkanones produced using the methods described herein are unbranched. In other embodiments, the alkanones produced are branched.

While reaction 100 produces products 110 that is made up of products A-F, including double-alkylated products such as 4-heptanone (B), 4-nonanone (D), and 6-undecanone (F), it should be understood that the product mixture may vary depending on the composition of the fermentation product mixture used and reaction conditions employed in the process described herein.

In certain embodiments, $R_1$ and $R_2$ may be independently substituted or unsubstituted alkyls. The alkyls may be any length. In some embodiments, each $R_1$ and $R_2$ is independently methyl, ethyl, propyl, isopropyl, butyl, pentyl, hexyl, or heptyl.

In other embodiments, the one or more compounds of Formula I are C5-C19 ketones. In other embodiments, the one or more compounds of Formula I are C5-C11 ketones. In yet other embodiments, the one or more compounds of Formula I are C11-C19 ketones.

In certain embodiments, the one or more compounds of Formula I may include

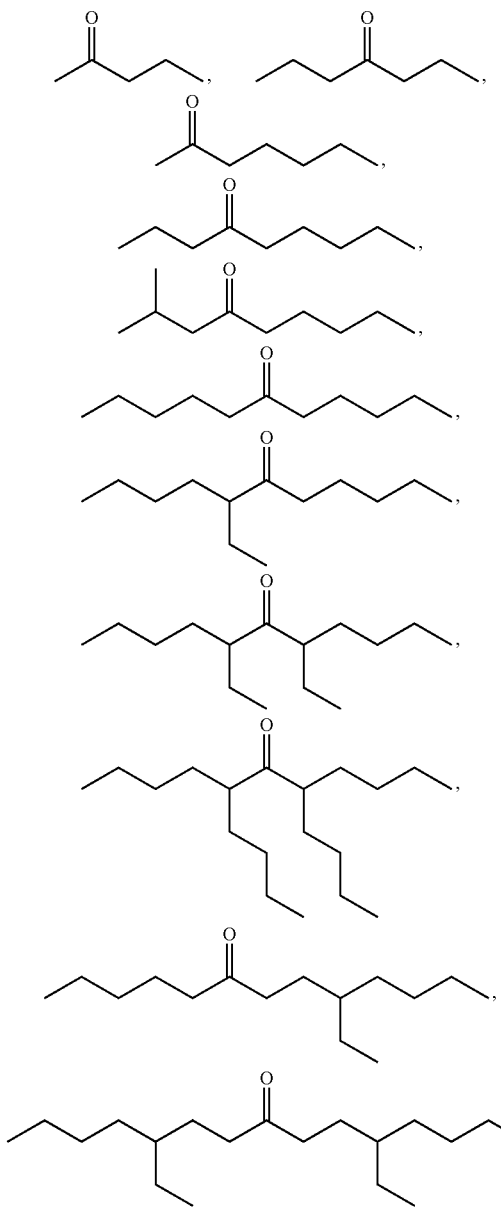

-continued

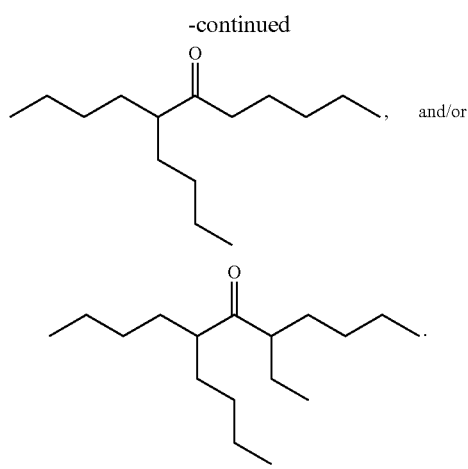

and/or

While mono-alkylated products may be produced according to the process described herein, in certain embodiments, at least one of one or more compounds of Formula I is a double-alkylated product. In some embodiments, at least 50% of the product mixture is made up of one or more double-alkylated products. In other embodiments, less than 20% of the product mixture is made up of one or more mono-alkylated products.

Following the production of one or more compounds of Formula I, these one or more compounds may be further hydrogenated, deformylated, isomerized, hydrodeoxygenated, or catalytically reformed. The double-alkylated products may be subsequently converted to either corresponding alcohols or alkanes, suitable for the manufacture of a fuel or lubricant.

Examples of alcohols produced from the methods described herein include:

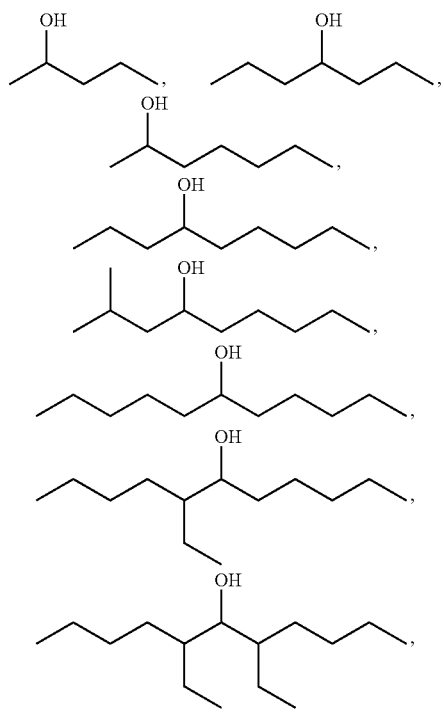

-continued

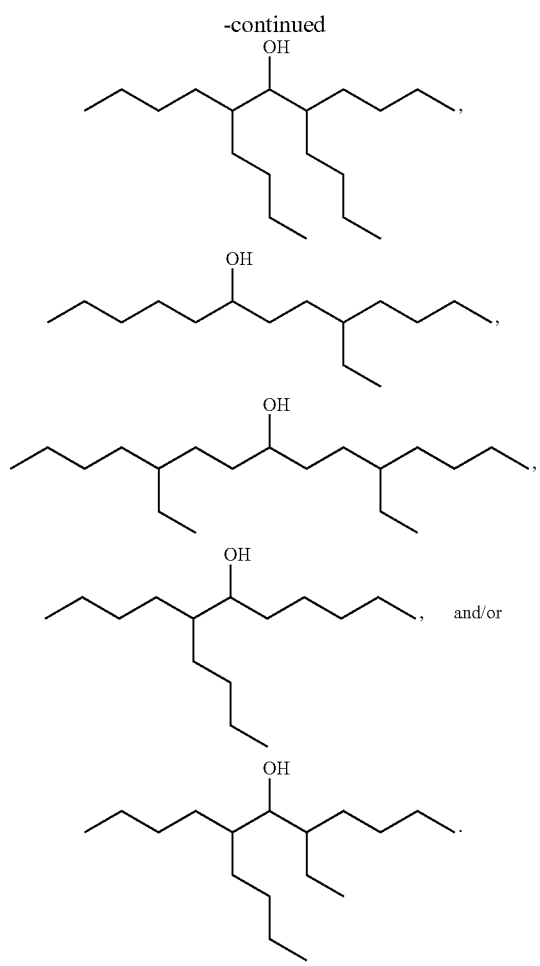

Examples of alcohols produced from the methods described herein include:

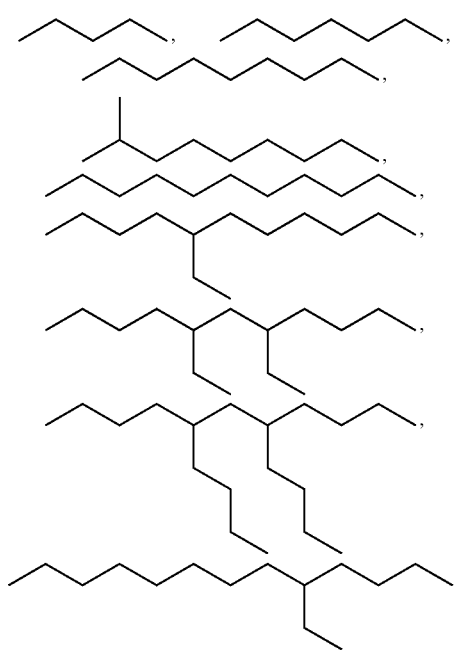

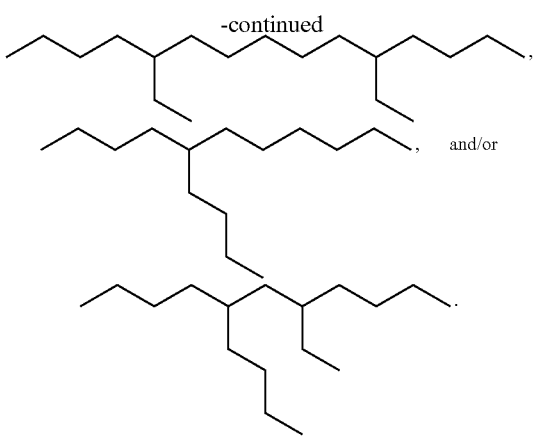

In some embodiments, the one or more compounds of Formula I may be converted into their corresponding alcohols in the presence of a metal-based catalyst. In certain embodiments, the metal-based catalyst includes platinum. In a specific embodiment, the second metal-based catalyst is palladium on carbon (Pd/C).

In other embodiments, the one or more compounds of Formula I may be converted into their corresponding alkanes in the presence of a metal-based catalyst. In certain embodiments, the metal-based catalyst includes platinum, nickel-molybdenum (Ni—Mo), nickel-tungsten (Ni—W), cobalt-molybdenum (Co—Mo), or combinations of these metals. In specific embodiments, the second metal-based catalyst is NiO—MoO$_3$/Al$_2$O$_3$, Pt/SiO$_2$—Al$_2$O$_3$, or combinations of these catalysts.

Figure 2:
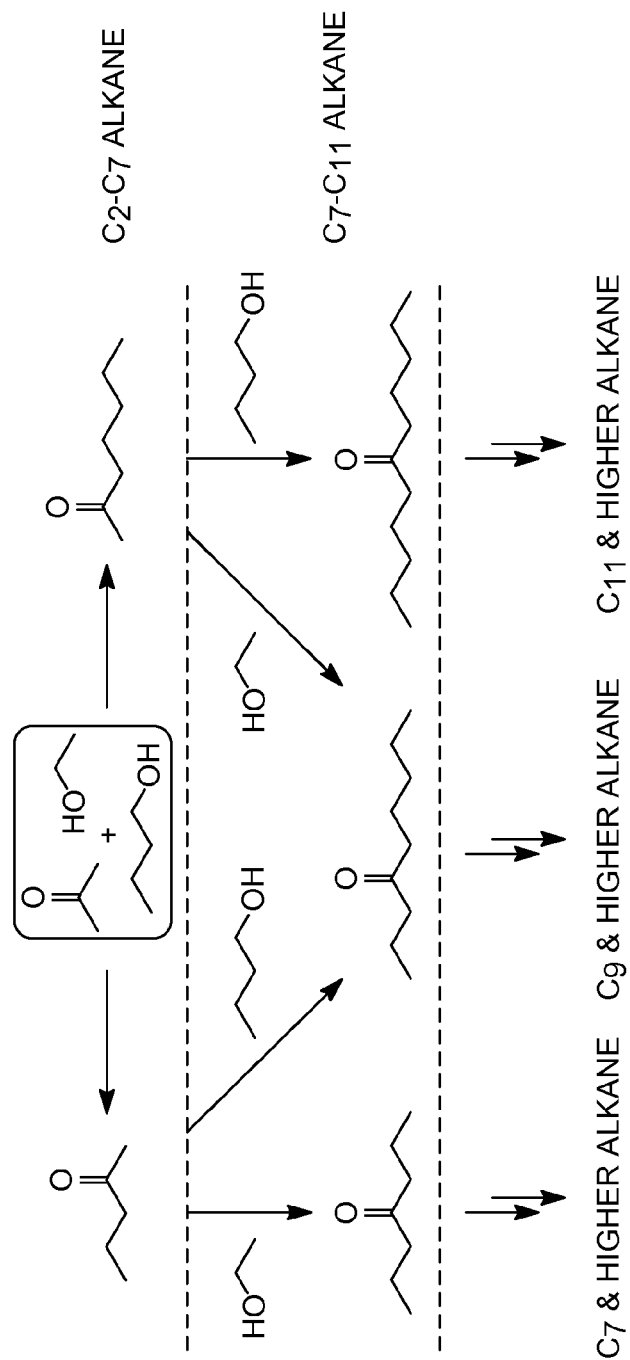
FIG. 2 depicts various exemplary products that may be derived from converting an ABE mixture into double-alkylated ketones.

FIG. 2 depicts an exemplary embodiment of C7-C11 alkanes produced by double-alkylation of the ABE mixture using the process described herein that may be converted into a fuel or lubricant. For example, 4-heptanone, 4-nonanone, and 6-undecanone, may be further deoxygenated to produce heptane, nonane, and undecane, respectively. These alkanes may be blended into diesel and jet fuel, or may be used independently as fuels following minor refinery upgrading. In some embodiments, the double-alkylated products obtained from the process described herein may be suitable for use as fuels that can power transportation vehicles (e.g., jets, diesel vehicles) and other combustion turbine applications.

It should be understood that the methods described herein may produce a mixture of compounds of Formula I or a mixture of alkanones. In certain embodiments, each of the compounds of Formula I, or each of the alkanones, in the product mixture can be separated before use in producing the corresponding alcohol or alkane.

Other Reactions to Produce Biodiesel

Figure 11:
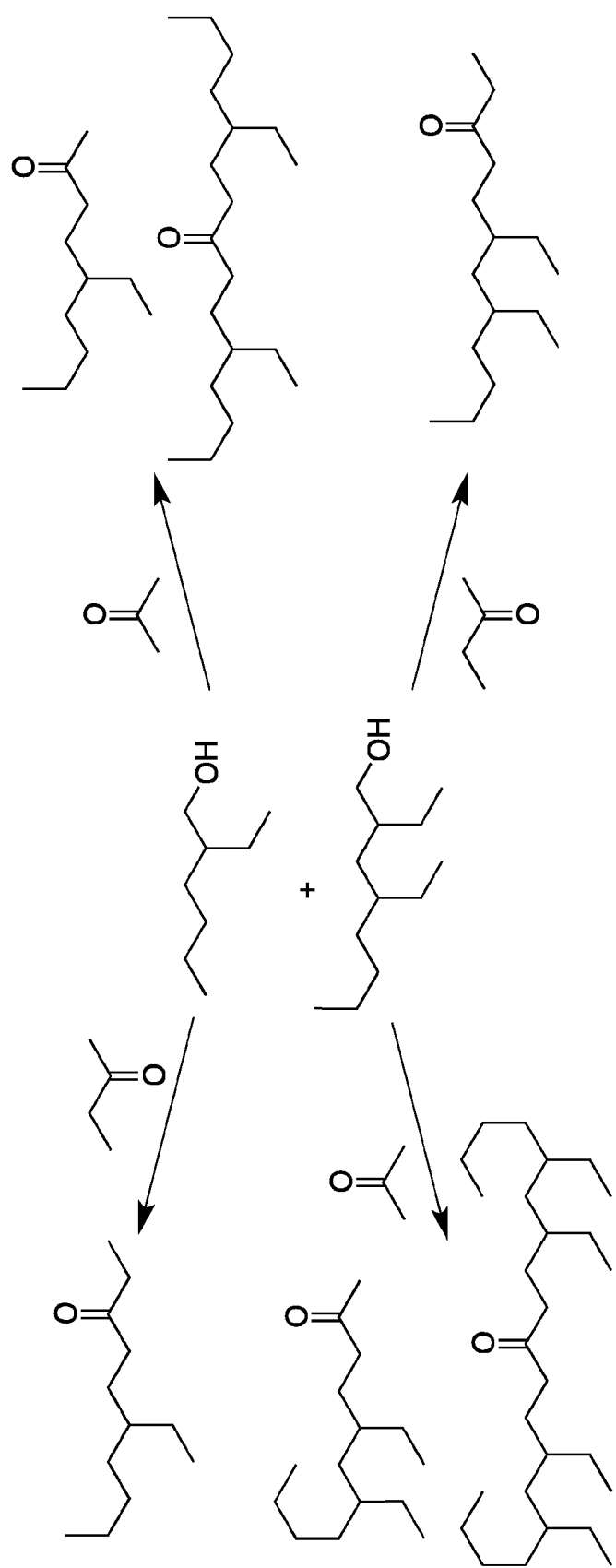
FIG. 11 is an exemplary reaction scheme for producing C11-C27 ketones from an ABE-mixture.

The alkylation of the fermentation product mixture using the methods described herein may produce an amount of Guerbet product. As depicted in FIG. 11, an exemplary reaction scheme, the dimerization of butanol via Guerbet reaction may be followed by alkylation with acetone or 2-butanone in a one-pot two-step process to yield one or more ketones ranging from C11-C27.

Figure 12:
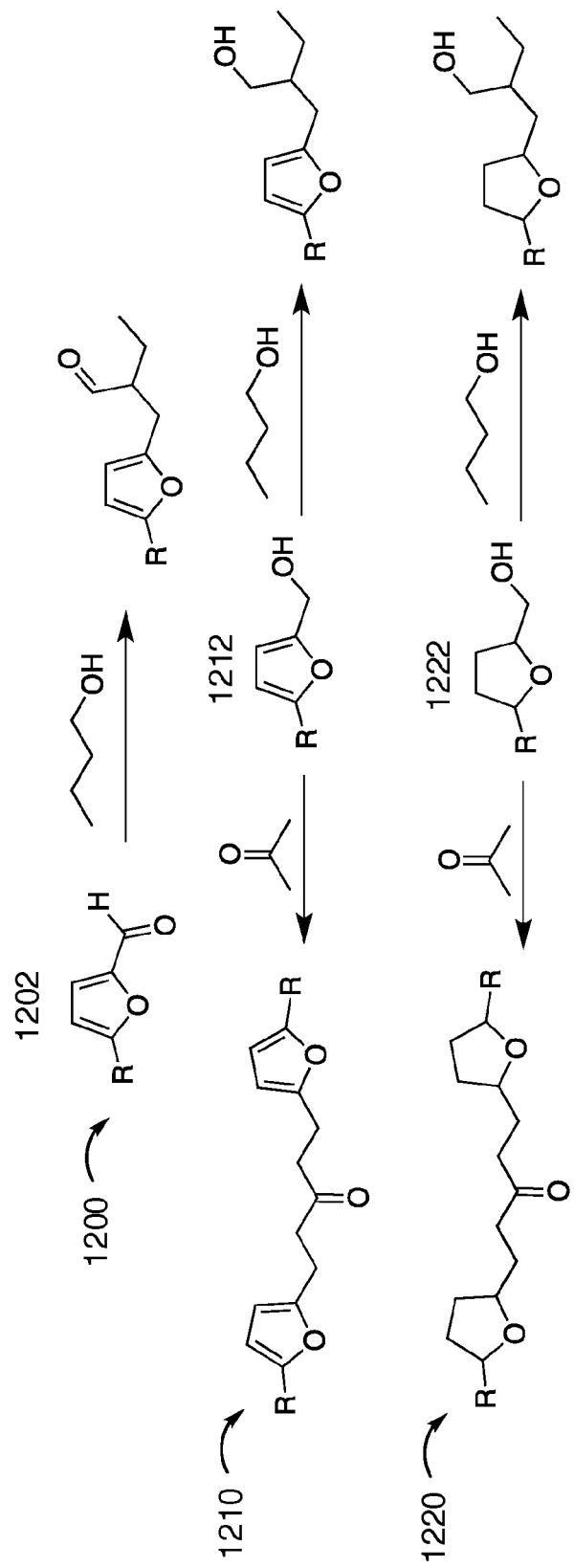
FIG. 12 is a scheme depicting three exemplary reactions for producing biodiesel from an ABE-mixture.

With reference to FIG. 12, exemplary reactions 1200, 1210, and 1220 are depicted. In reaction 1200, starting material 1202 may be reacted with butanol to yield biodiesel and various biofuel-related precursors or products. In reaction 1210, starting material 1212 may be reacted with acetone and/or butanol to yield biodiesel and various biofuel-related precursors or products. In reaction 1220, starting material 1222 may be reacted with acetone and/or butanol to yield biodiesel and various biofuel-related precursors or products.

EXAMPLES

The following Examples are merely illustrative and are not meant to limit any aspects of the present disclosure in any way.

All reactions were carried out in closed system using 12 mL Q-Tube (pressure tube) in a parallel optimizer. All the metal sources were purchased from either Aldrich or Strem Chemicals and used as received. Acetone, ethanol and butanol, as well as other chemicals, were obtained from Aldrich and used without further purification. All the reactions were analyzed by gas chromatography using dodecane as internal standard. Gas chromatography (GC) analysis was performed on a Varian CP-3800 instrument with a FID detector and VF5 ms column (5% phenyl and 95% methyl-polysiloxane) using helium as carrier gas.

Example 1

Metal-Catalyzed Alkylation of Acetone Using ABE-Mix

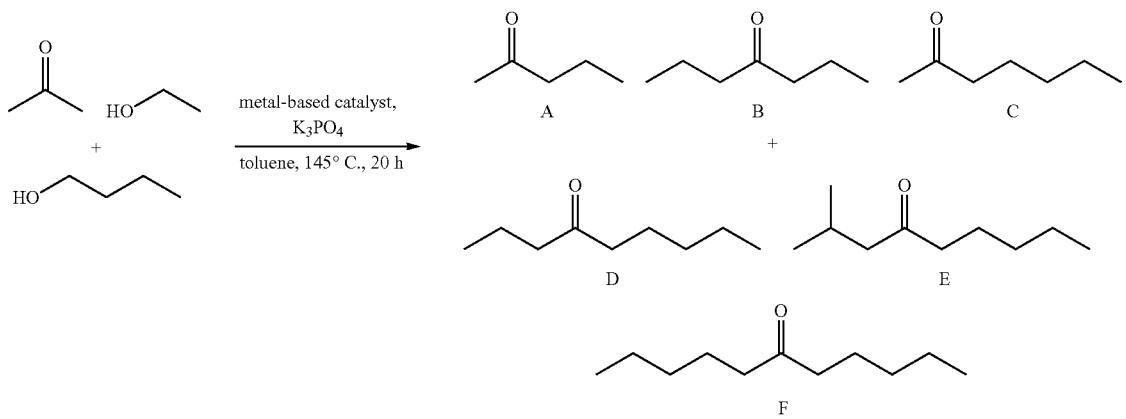

Figure 3:
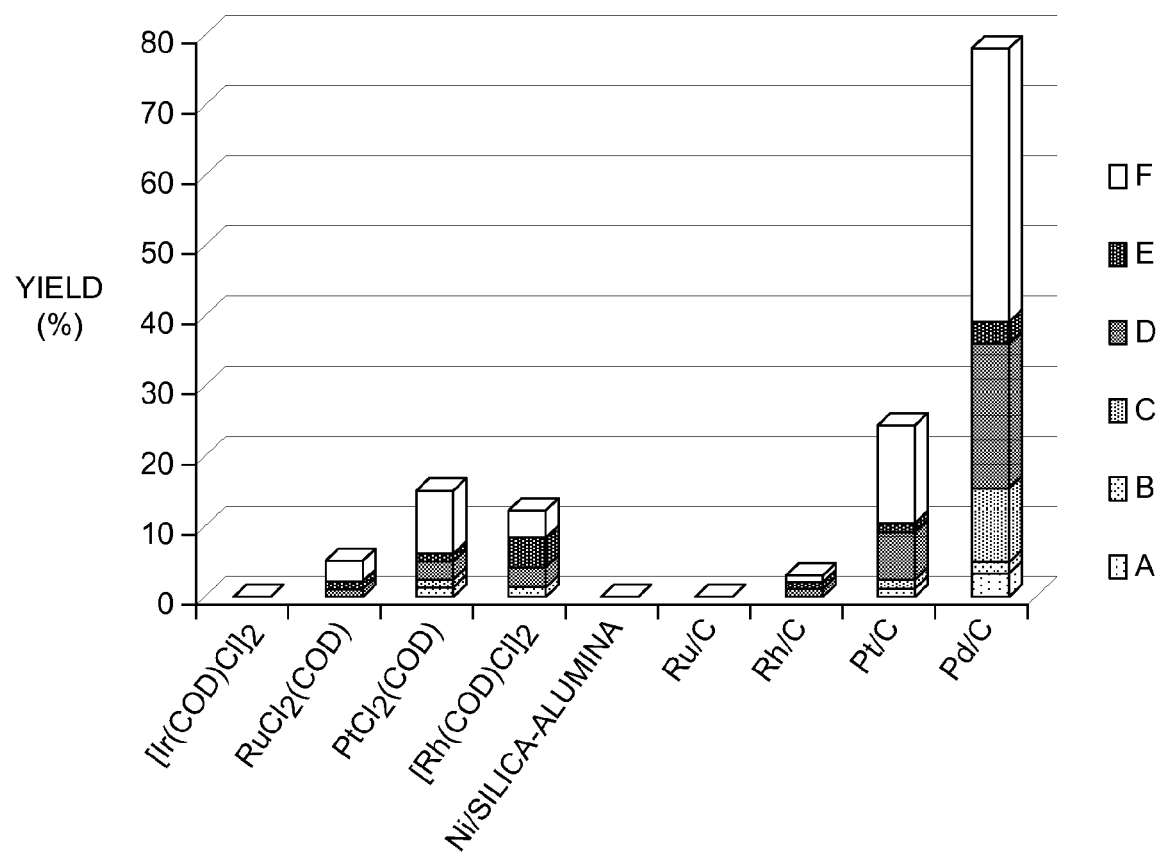
FIG. 3 is a graph depicting the yield of A-F products from varying the metal-based catalysts in the alkylation of acetone in ABE mix.

A metal-based catalyst (0.01 mmol) selected from the list in Table 1 below, K₃PO₄ (954 mg, 4.5 mmol), and a magnetic stir bar were added to a 12-mL Q-Tube (pressure tube). To each tube, 1.5 mL of toluene was added. Then, acetone (0.17 mL, 2.3 mmol), ethanol (60 µL, 1 mmol), and butanol (0.34 mL, 3.7 mmol) were also added to each tube. Each tube was sealed, and kept at 145° C. in a pre-heated metal block. Each reaction mixture was stirred for 20 hours at 145° C., and then cooled to room temperature. Subsequently, dodecane (internal standard) was added and diluted with ethyl acetate. GC analysis of each reaction mixture yielded the ratio of A-F products in Table 1 below and as depicted in FIG. 3. Yields were determined based on acetone.

Figure 4:
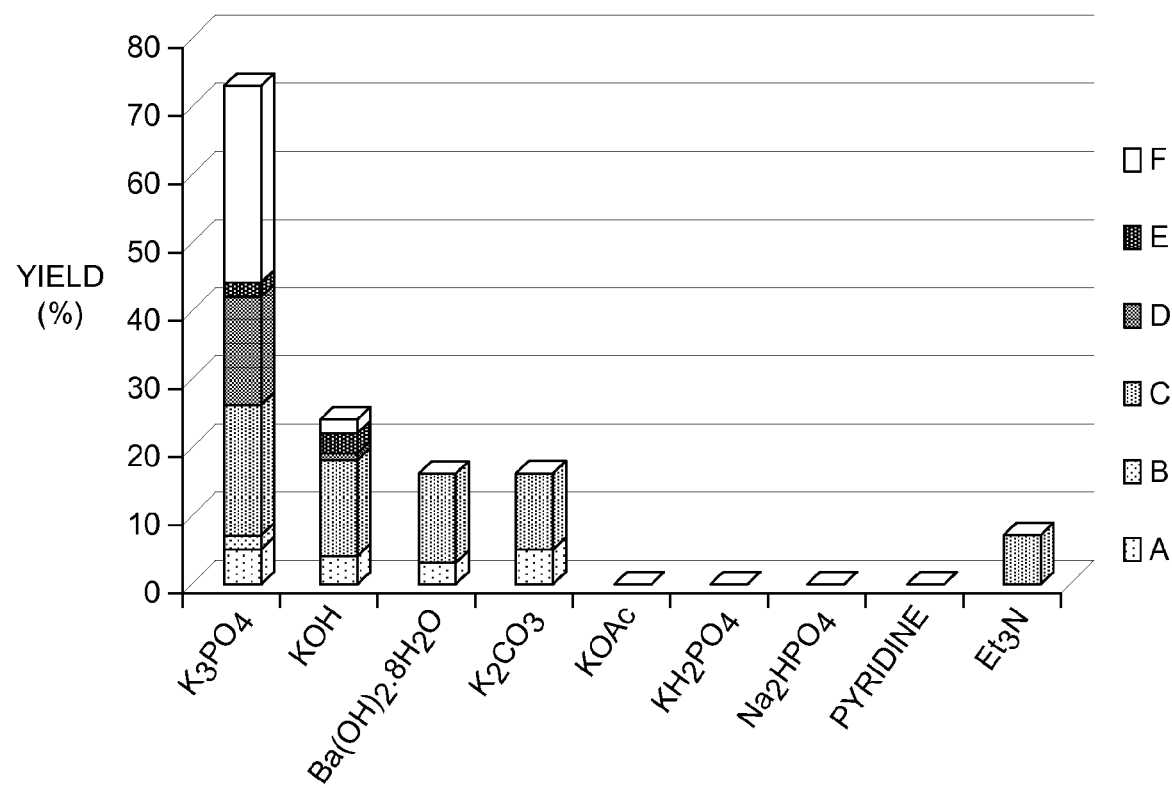
FIG. 4 is a graph depicting the yield of A-F products from varying the base in the alkylation of acetone in ABE mix.

5% palladium on carbon (containing 50% of water, 42 mg, 0.01 mmol), a base (4.5 mmol) selected from the list in Table 2 below, and a magnetic stir bar were added to a 12-mL Q-Tube (pressure tube). To each tube, 1.5 mL of toluene was added. Then, acetone (0.17 mL, 2.3 mmol), ethanol (60 µL, 1 mmol), and butanol (0.34 mL, 3.7 mmol) were also added to each tube. Each tube was sealed, and kept at 145° C. in a pre-heated metal block. The reaction mixture was stirred for 20 hours at 145° C., and then cooled to room temperature. Subsequently, dodecane (internal standard) was added and diluted with ethyl acetate. GC analysis of each reaction mixture yielded the ratio of A-F products in Table 2 below and as depicted in FIG. 4. Yields were determined based on acetone.

TABLE 1

Variation of metal-based catalysts in alkylation of acetone in ABE mix

| Metal-based catalyst | Yield (%) | | | | | | |
|---|---|---|---|---|---|---|---|
| | A | B | C | D | E | F | Total |
| [Ir(COD)Cl]₂ | 0 | 0 | 0 | 0 | 0 | 0 | 0 |
| RuCl₂(COD) | 0 | 0.2 | 0.1 | 1.1 | 0.4 | 2.4 | 4.2 |
| PtCl₂(COD) | 0.1 | 0.4 | 0.6 | 2.8 | 0.5 | 8.8 | 13.2 |
| [Rh(COD)Cl]₂ | 0 | 0.6 | 0.1 | 2.7 | 3.6 | 4.1 | 11.1 |
| Ni/Silica-Alumina | 0 | 0 | 0 | 0 | 0 | 0 | 0 |
| Ru/C | 0 | 0 | 0 | 0 | 0 | 0 | 0 |
| Rh/C | 0.1 | 0.3 | 0.2 | 1 | 0.8 | 1.2 | 3.6 |
| Pt/C | 0 | 0.6 | 0.5 | 6.5 | 1.1 | 13.9 | 22.6 |
| Pd/C | 2.7 | 2.4 | 9.6 | 21.5 | 2.9 | 39.1 | 78.2 |

Example 2

Alkylation of Acetone Using ABE-Mix with Various Bases

TABLE 2

Variation of base in alkylation of acetone in ABE mix

| Base | Yield (%) | | | | | | |
|---|---|---|---|---|---|---|---|
| | A | B | C | D | E | F | Total |
| K₃PO₄ | 4.4 | 2.1 | 18.4 | 15.9 | 2 | 29.3 | 72.1 |
| KOH | 3.5 | 0 | 13.9 | 1 | 3.1 | 2.1 | 23.6 |
| Ba(OH)₂·8H₂O | 2.5 | 0 | 12.6 | 0 | 0 | 0 | 15.1 |
| K₂CO₃ | 4.8 | 0 | 10.5 | 0 | 0 | 0 | 15.3 |
| KOAc | 0 | 0 | 0 | 0 | 0 | 0 | 0 |
| KH₂PO₄ | 0 | 0 | 0 | 0 | 0 | 0 | 0 |
| Na₂HPO₄ | 0 | 0 | 0 | 0 | 0 | 0 | 0 |
| Pyridine | 0 | 0 | 0 | 0 | 0 | 0 | 0 |
| Et₃N | 0 | 0 | 7.1 | 0 | 0 | 0 | 7.1 |

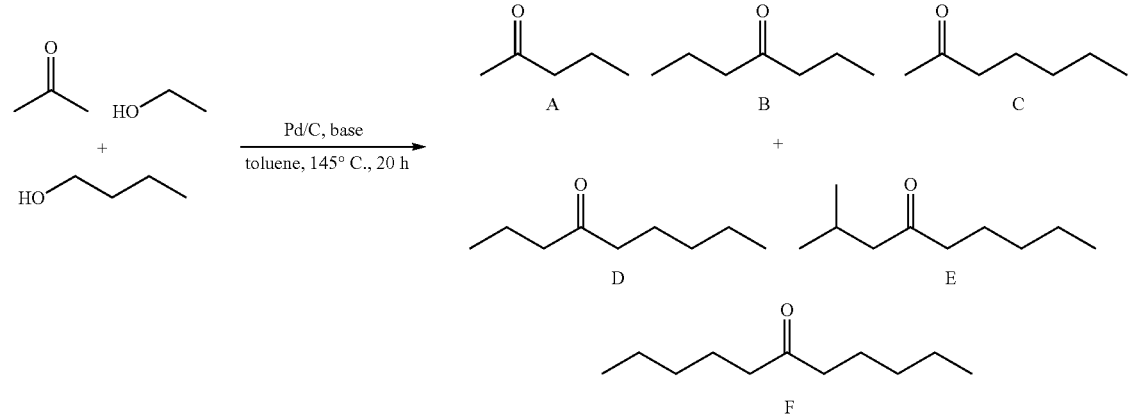

Example 3

Alkylation of Acetone Using ABE-Mix with Various Palladium-Based Catalysts

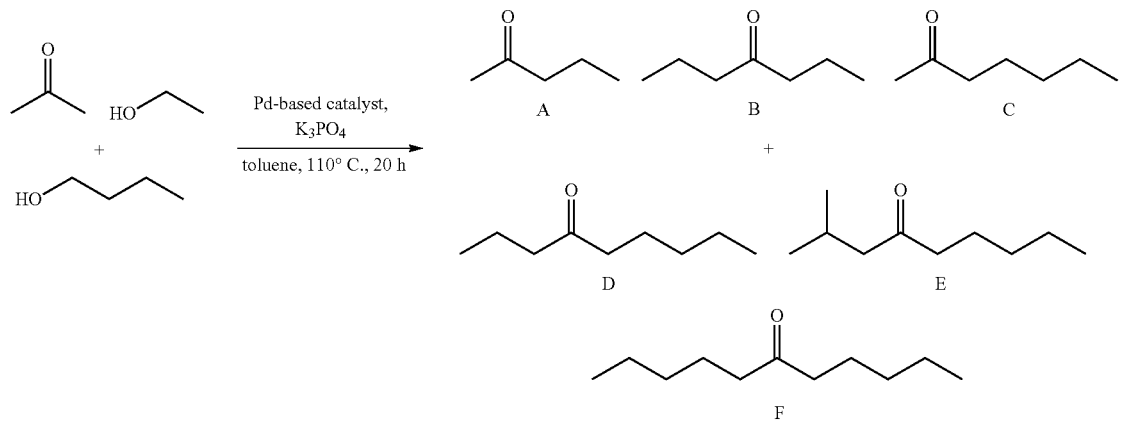

Figure 5:
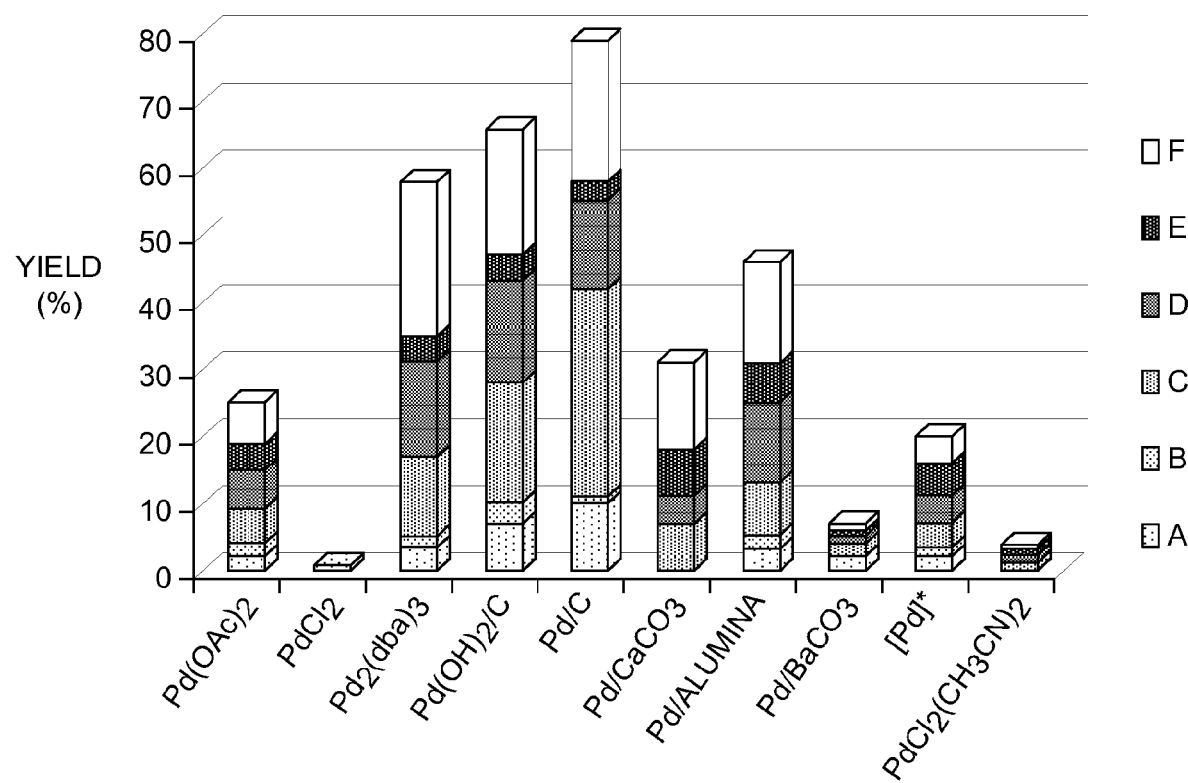
FIG. 5 is a graph depicting the yield of A-F products from varying the palladium-based catalyst in the alkylation of acetone in ABE mix.

A palladium-based catalyst (0.01 mmol) selected from the list in Table 3 below, $K_3PO_4$ (3 mmol), and a magnetic stir bar were added to a 12-mL Q-Tube (pressure tube). To each tube, 1.5 mL of toluene was added. Then, acetone (0.17 mL, 2.3 mmol), ethanol (60 μL, 1 mmol), and butanol (0.34 mL, 3.7 mmol) were also added to each tube. Each tube was sealed, and kept at 110° C. in a pre-heated metal block. The reaction mixture was stirred for 20 hours at 110° C., and then cooled to room temperature. Subsequently, dodecane (internal standard) was added and diluted with ethyl acetate. GC analysis of each reaction mixture yielded the ratio of A-F products in Table 3 below and as depicted in FIG. 5. Yields were determined based on acetone.

TABLE 3

Variation of palladium-based catalysts in alkylation of acetone in ABE mix

| Pd-Source | Yield (%) | | | | | | |
|---|---|---|---|---|---|---|---|
| | A | B | C | D | E | F | Total |
| $Pd(OAc)_2$ | 2 | 2 | 5 | 6 | 4 | 6 | 25 |
| $PdCl_2$ | 1 | 0 | 0 | 0 | 0 | 0 | 1 |

TABLE 3-continued

Variation of palladium-based catalysts in alkylation of acetone in ABE mix

| Pd-Source | Yield (%) | | | | | | |
|---|---|---|---|---|---|---|---|
| | A | B | C | D | E | F | Total |
| $Pd_2(dba)_3$ | 3 | 2 | 12 | 14 | 4 | 23 | 58 |
| $Pd(OH)_2/C$ | 7 | 3 | 18 | 15 | 4 | 19 | 66 |
| Pd/C | 10 | 1 | 31 | 13 | 3 | 21 | 79 |
| $Pd/CaCO_3$ | 0 | 0 | 7 | 4 | 7 | 13 | 31 |
| Pd/Alumina | 3 | 2 | 8 | 12 | 6 | 15 | 46 |
| $Pd/BaCO_3$ | 2 | 0 | 2 | 1 | 1 | 1 | 7 |
| [Pd]* (i.e.,Pd-Polyethylenimines on Silica) | 2 | 1 | 4 | 4 | 5 | 4 | 20 |
| $PdCl_2(CH_3CN)_2$ | 0 | 0 | 1 | 1 | 1 | 1 | 4 |

Example 4

Alkylation of Acetone Using ABE-Mix at Various Reaction Temperatures

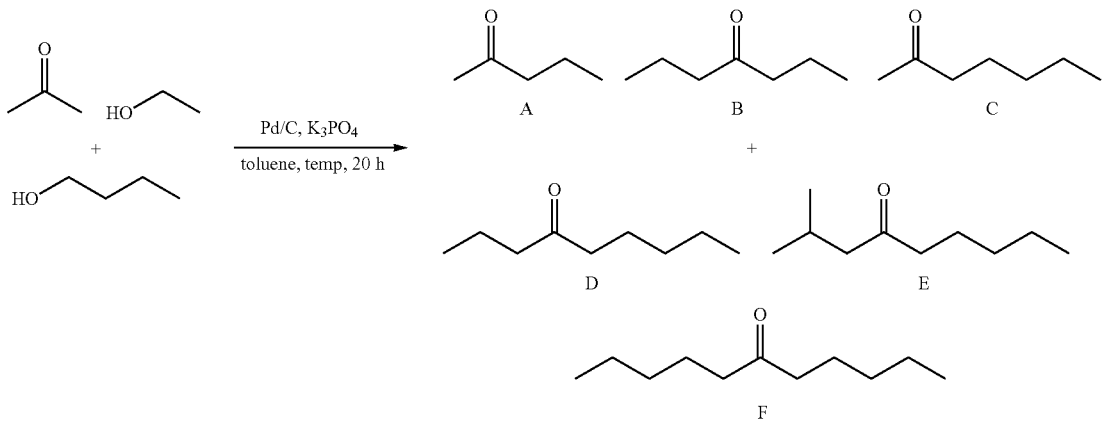

5% palladium on carbon (containing 50% of water, 42 mg, 0.01 mmol), $K_3PO_4$ (3 mmol), and a magnetic stir bar were added to a 12-mL Q-Tube (pressure tube). To each tube, 1.5 mL of toluene was added. Then, acetone (0.17 mL, 2.3 mmol), ethanol (60 μL, 1 mmol), and butanol (0.34 mL, 3.7 mmol) were also added to each tube. Each tube was sealed, and kept in a pre-heated metal block at one of the temperatures listed in Table 4 below. Each reaction mixture was stirred for 20 hours at that temperature, and then cooled to room temperature. Subsequently, dodecane (internal standard) was added and diluted with ethyl acetate. GC analysis of each reaction mixture yielded the ratio of A-F products in Table 4 below and as depicted in FIG. 6A. Yields were determined based on acetone.

TABLE 4

Variation of temperature in alkylation of acetone in ABE mix

| | Yield (%) | | | | | | |
|---|---|---|---|---|---|---|---|
| Temp | A | B | C | D | E | F | Total |
| 110° C. | 10.4 | 1 | 30.7 | 12.9 | 2.4 | 21.1 | 78.5 |
| 130° C. | 5.4 | 2 | 20.4 | 14.7 | 1.7 | 25.6 | 69.8 |
| 145° C. | 4.4 | 2.1 | 18.4 | 15.9 | 2 | 29.3 | 72.1 |
| 160° C. | 4.1 | 1.7 | 20.7 | 15.6 | 1.9 | 31.7 | 75.7 |
| 180° C. | 1.3 | 0.6 | 18.9 | 12.7 | 1.5 | 32.5 | 67.5 |

Example 5

Alkylation of Acetone Using ABE-Mix with Various Amounts of $K_3PO_4$

5% palladium on carbon (containing 50% of water, 42 mg, 0.01 mmol), $K_3PO_4$ (mmol varied according to amounts in Table 5), and a magnetic stir bar were added to a 12-mL Q-Tube (pressure tube). To each tube, 1.5 mL of toluene was added. Then, acetone (0.17 mL, 2.3 mmol), ethanol (60 μL, 1 mmol), and butanol (0.34 mL, 3.7 mmol) were also added to each tube. Each tube was sealed, and kept at 145° C. in a pre-heated metal block. The reaction mixture was stirred for 20 hours at 145° C., and then cooled to room temperature. Subsequently, dodecane (internal standard) was added and diluted with ethyl acetate. GC analysis of the reaction mixture yielded the ratio of A-F products in Table 5 below and as depicted in FIG. 6B. Yields were determined based on acetone.

TABLE 5

Variation of amount of $K_3PO_4$ in alkylation of acetone in ABE mix

| $K_3PO_4$ (mmol) | $K_3PO_4$ (mol %)[a] | Yield (%) | | | | | | |
|---|---|---|---|---|---|---|---|---|
| | | A | B | C | D | E | F | Total |
| 1.5 | 32 | 11 | 1 | 30 | 6 | 1 | 10 | 59 |
| 3.0 | 64 | 5 | 2 | 19 | 16 | 2 | 29 | 73 |
| 4.5 | 96 | 1 | 2 | 7 | 20 | 3 | 44 | 77 |
| 6.0 | 128 | 1 | 2 | 4 | 23 | 5 | 51 | 86 |

[a]calculated based on alcohols

It should be understood that 1.5 to 6 mmol of $K_3PO_4$ was used in this Example, which is 32 to 128 mol %, or 0.32 to 1.3 molar equivalents to the amount of alcohol used in the reaction. For example, 1.5 mmol of $K_3PO_4$ to 4.7 mmol of alcohols equals 0.32 molar equivalents (or 32 mol %) of $K_3PO_4$.

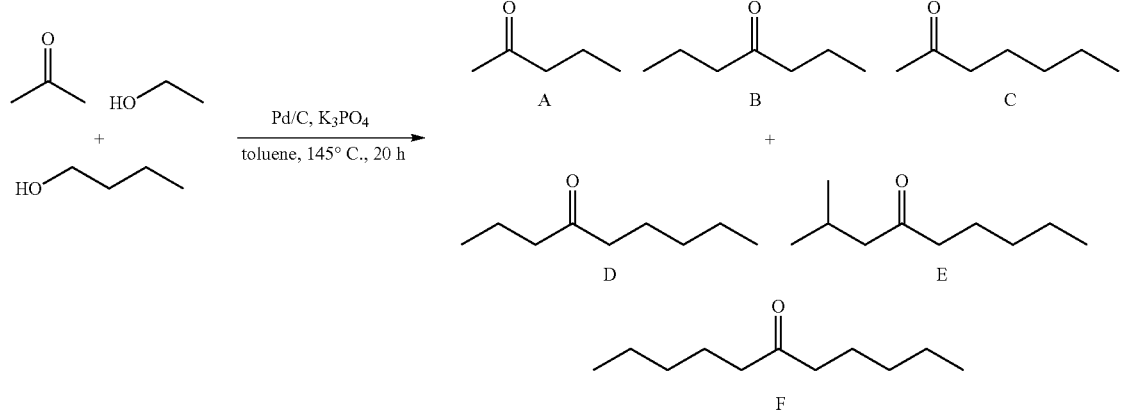

Example 6

Alkylation of Acetone Using ABE-Mix with Various Solvents

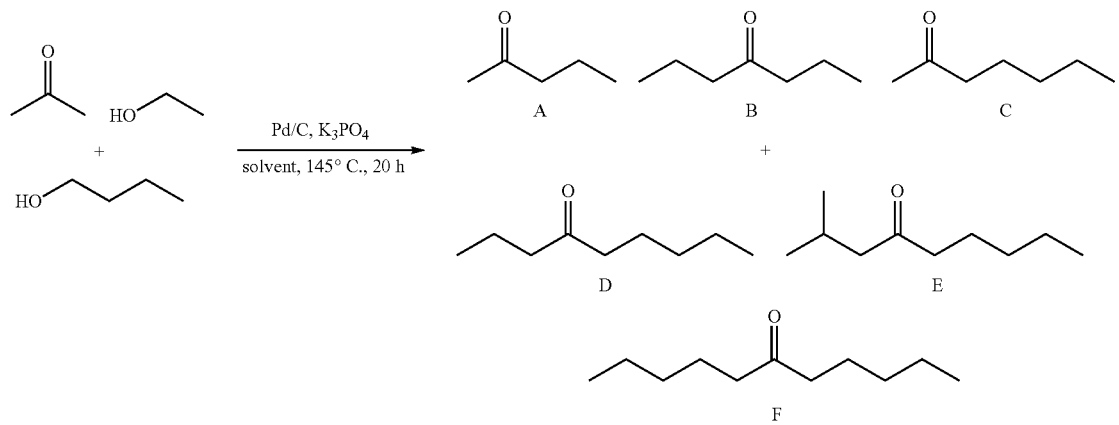

5% palladium on carbon (containing 50% of water, 42 mg, 0.01 mmol), K$_3$PO$_4$ (4.5 mmol), and a magnetic stir bar were added to a 12-mL Q-Tube (pressure tube). To each tube, 1.5 mL of solvent selected from Table 6 below was added. The solvents were selected for use in this Example based on their suitability for the extraction of the starting materials from the fermentation process, or for direct blending with the products from the fermentation process. For example, ethyl acetate can be produced from biomass. Monoglyme and diglyme can be used after fermentation for separation of the ABE mixture from water. Butanol can be blended directly with the bio-butanol produced by fermentation.

Then, acetone (0.17 mL, 2.3 mmol), ethanol (60 µL, 1 mmol), and butanol (0.34 mL, 3.7 mmol) were also added to each tube. Each tube was sealed, and kept at 145° C. in a pre-heated metal block. Each reaction mixture was stirred for 20 hours at 145° C., and then cooled to room temperature. Subsequently, dodecane (internal standard) was added and diluted with ethyl acetate. GC analysis of each reaction mixture yielded the ratio of A-F products in Table 6 below. Yields were determined based on acetone.

TABLE 6

Variation of solvent in alkylation of acetone in ABE mix

| Solvent | Yield (%) | | | | | | |
|---|---|---|---|---|---|---|---|
| | A | B | C | D | E | F | Total |
| Toluene | 1 | 2 | 7 | 20 | 3 | 44 | 77 |
| Ethyl acetate | 28 | 12 | 8 | 7 | 0 | 2 | 57 |
| Diglyme | 5 | 3 | 3 | 20 | 4 | 39 | 74 |
| Diglybu | 1 | 3 | 6 | 22 | 6 | 35 | 73 |
| Butanol[a] | 0 | 1 | 3 | 8 | 2 | 60 | 74 |
| Neat[b] | 5 | 2 | 5 | 14 | 8 | 27 | 61 |
| Oleyl alcohol[a] | 3.2 | 1 | 11.5 | 7.2 | 2 | 12.6 | 37.5 |
| Dibutyl phthalate | 1.2 | 0.2 | 10.3 | 3.1 | 1.7 | 14.2 | 30.7 |

[a]1.5 mmol K$_3$PO$_4$ was used in the reaction
[b]5 µmol Pd/C (with respect to alcohols)

Example 7

Alkylation of Acetone Using ABE-Mix at Various Reaction Temperatures to Form Mono-Alkylated Products

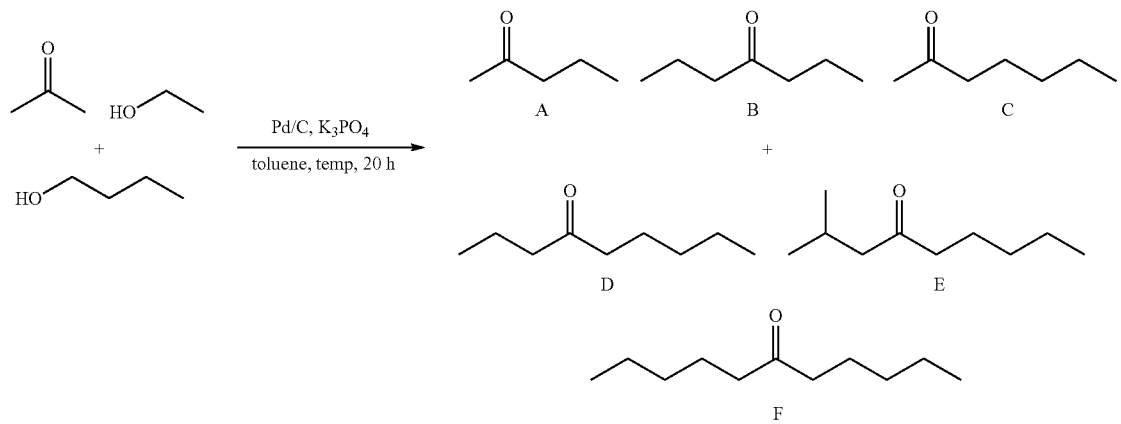

5% palladium on carbon (containing 50% of water, 42 mg, 0.01 mmol), $K_3PO_4$ (1.5 mmol), and a magnetic stir bar were added to a 12-mL Q-Tube (pressure tube). To each tube, 1.5 mL of toluene was added. Then, acetone (0.17 mL, 2.3 mmol), ethanol (60 μL, 1 mmol), and butanol (0.34 mL, 3.7 mmol) were also added to each tube. Each tube was sealed, and kept in a pre-heated metal block at one of the temperatures listed in Table 7 below. Each reaction mixture was stirred for 20 hours at that temperature, and then cooled to room temperature. Subsequently, dodecane (internal standard) was added and diluted with ethyl acetate. GC analysis of each reaction mixture yielded the ratio of A-F products in Table 7 below. Yields were determined based on acetone.

TABLE 7

Variation of temperature in alkylation of acetone in ABE mix to form mono-alkylated products

| Temp | Yield (%) | | | | | | |
|---|---|---|---|---|---|---|---|
| | A | B | C | D | E | F | Total |
| 110° C. | 8.5 | 0.5 | 19.9 | 2.7 | 0 | 3.3 | 34.9 |
| 130° C. | 9.2 | 0.8 | 29.8 | 6.1 | 0.4 | 10.5 | 56.8 |
| 145° C. | 11.4 | 0.8 | 37.9 | 5.9 | 0.4 | 9.9 | 66.3 |
| 160° C. | 8.6 | 0.8 | 36.8 | 6.3 | 0.5 | 12.9 | 65.9 |
| 180° C. | 3.1 | 0.6 | 21.4 | 7.1 | 0.5 | 24.2 | 56.9 |

Example 8

Alkylation of Acetone Using ABE-Mix Over Time

Figure 8:
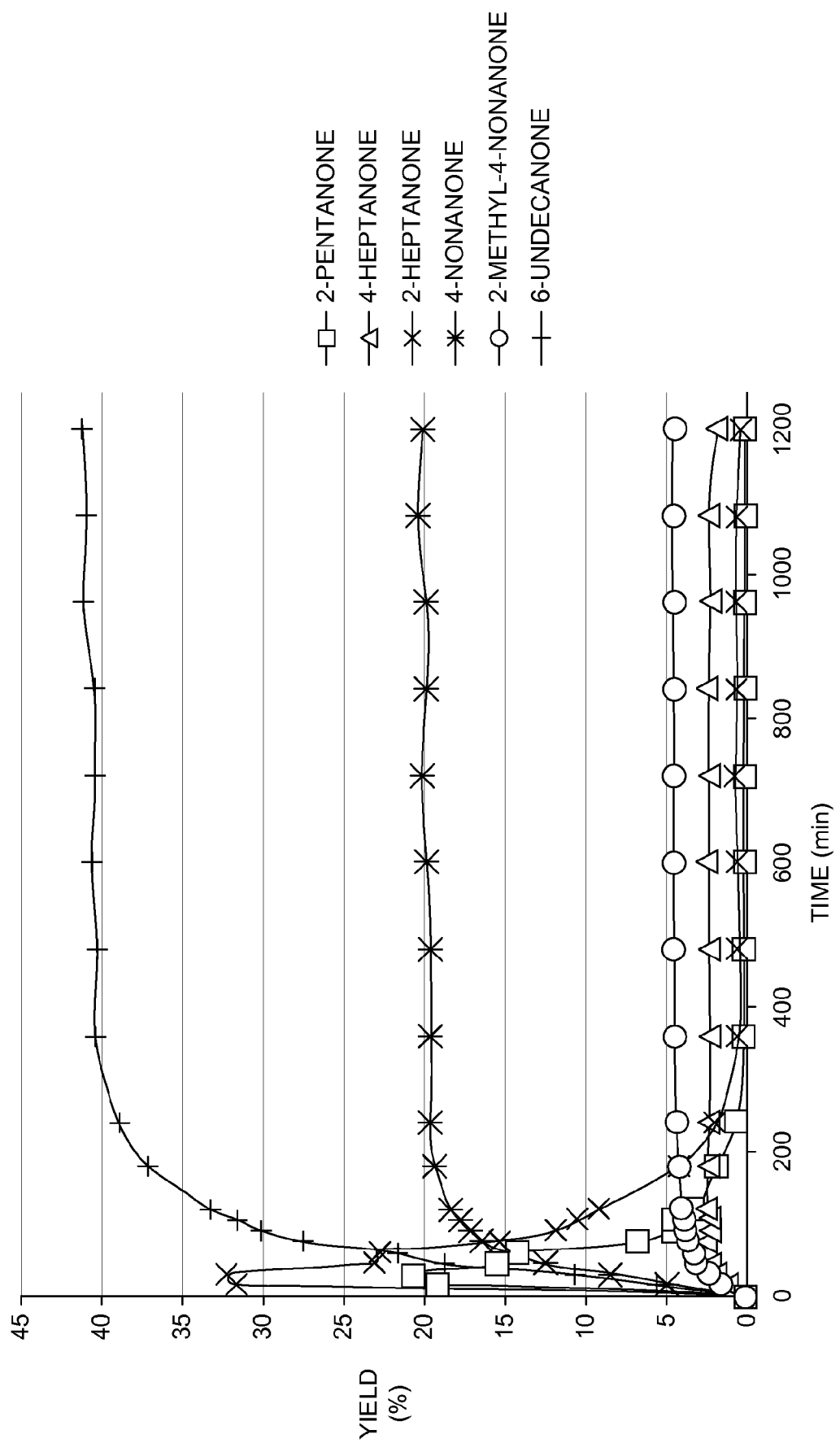
FIG. 8 is a graph depicting the product distribution of A-F products at specific times, from 15-1200 minutes.

5% palladium on carbon (0.02 mmol), $K_3PO_4$ (9 mmol), and a magnetic stir bar were added to a 12-mL Q-Tube (pressure tube). To each tube, 3 mL of toluene was added. Then, acetone (4.6 mmol), ethanol (2 mmol), and butanol (7.4 mmol) were also added to each tube. Each tube was sealed, and kept at 145° C. in a pre-heated metal block. Each reaction mixture was stirred at 145° C. over 20 hours. Samples were taken during the 20 hours according to the times listed in Table 8. Each sample was cooled to room temperature. To each sample, dodecane (internal standard) was added and diluted with ethyl acetate. GC analysis of each reaction sample yielded the ratio of A-F products in Table 8 below and as depicted in FIG. 8. Yields were determined based on acetone.

TABLE 8

Product distribution during reaction at given times

| Time (min) | Yield (%) | | | | | | |
|---|---|---|---|---|---|---|---|
| | A | B | C | D | E | F | Total |
| 15 | 19.2 | 1.3 | 31.6 | 4.9 | 1.6 | 5.6 | 64.2 |
| 30 | 20.7 | 2 | 32.2 | 8.4 | 2.3 | 10.6 | 76.2 |
| 45 | 15.4 | 2.3 | 23.1 | 12.5 | 3.1 | 18.7 | 75.1 |
| 60 | 14.2 | 2.7 | 22.7 | 14.5 | 3.2 | 21.6 | 78.9 |
| 75 | 6.8 | 2.4 | 15.3 | 16.4 | 3.6 | 27.5 | 72 |
| 90 | 4.6 | 2.3 | 11.8 | 17.1 | 3.7 | 30.1 | 69.6 |
| 105 | 4.5 | 2.3 | 10.5 | 17.7 | 3.8 | 31.6 | 70.4 |
| 120 | 3.1 | 2.4 | 9.1 | 18.3 | 4 | 33.2 | 70.1 |
| 180 | 1.8 | 2.4 | 4.2 | 19.3 | 4.2 | 37.1 | 69 |
| 240 | 0.7 | 2.3 | 1.8 | 19.6 | 4.3 | 38.9 | 67.6 |
| 360 | 0.13 | 2.3 | 0.5 | 19.6 | 4.4 | 40.4 | 67.33 |
| 480 | 0.13 | 2.3 | 0.5 | 19.6 | 4.5 | 40.3 | 67.33 |
| 600 | 0.1 | 2.4 | 0.5 | 19.8 | 4.4 | 40.6 | 67.8 |
| 720 | 0.1 | 2.3 | 0.7 | 20.1 | 4.5 | 40.4 | 68.1 |
| 840 | 0.06 | 2.4 | 0.5 | 19.9 | 4.4 | 40.5 | 67.76 |
| 960 | 0.06 | 2.2 | 0.6 | 19.9 | 4.4 | 41.1 | 68.26 |
| 1080 | 0.04 | 2.3 | 0.6 | 20.4 | 4.5 | 40.9 | 68.74 |
| 1200 | 0.02 | 1.8 | 0.4 | 20.1 | 4.4 | 41.2 | 67.92 |

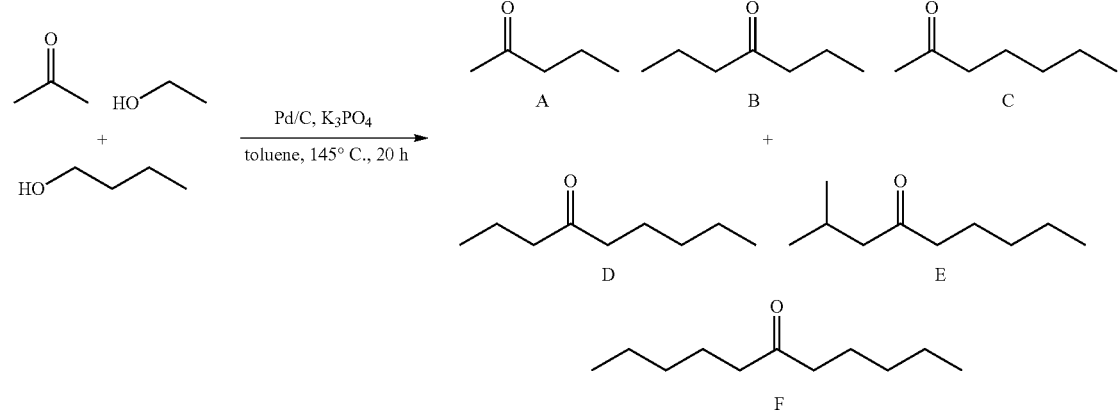

Example 9

One-Pot Alkylation and Hydrogenation Using ABE-Mix

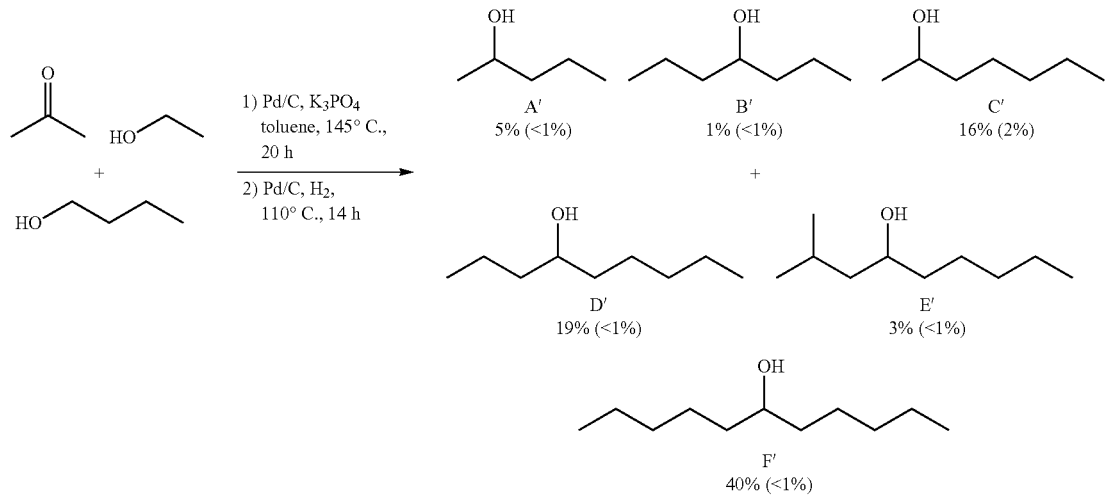

5% palladium on carbon (0.01 mmol), K₃PO₄ (4.5 mmol), and a magnetic stir bar were added to a high-pressure reaction vessel (HEL parallel synthesizer). To the tube, 1.5 mL of toluene was added. Then, acetone (2.3 mmol), ethanol (1 mmol), and butanol (3.7 mmol) were also added to the tube. The tube was sealed, and kept at 145° C. in a pre-heated metal block. The reaction mixture was stirred at 145° C. over 20 hours. A sample of the reaction mixture was taken for GC analysis.

To this reaction mixture, 5% platinum on carbon (0.02 mmol) was added, and the reaction vessel was pressurized with H₂ gas (150 psi). The reaction mixture was stirred at 110° C. for 14 hours, and then cooled to room temperature. GC analysis of the reaction mixture yielded the ratio of A'-F' products as shown in the reaction scheme above. Yields were determined based on acetone. The yields in parentheses denote the corresponding yields of the ketones.

Example 10

One-Pot Alkylation and Hydrogenation Using ABE-Mix with Various Amounts of Base, Temperature, H₂ Gas to Produce Corresponding Alcohols

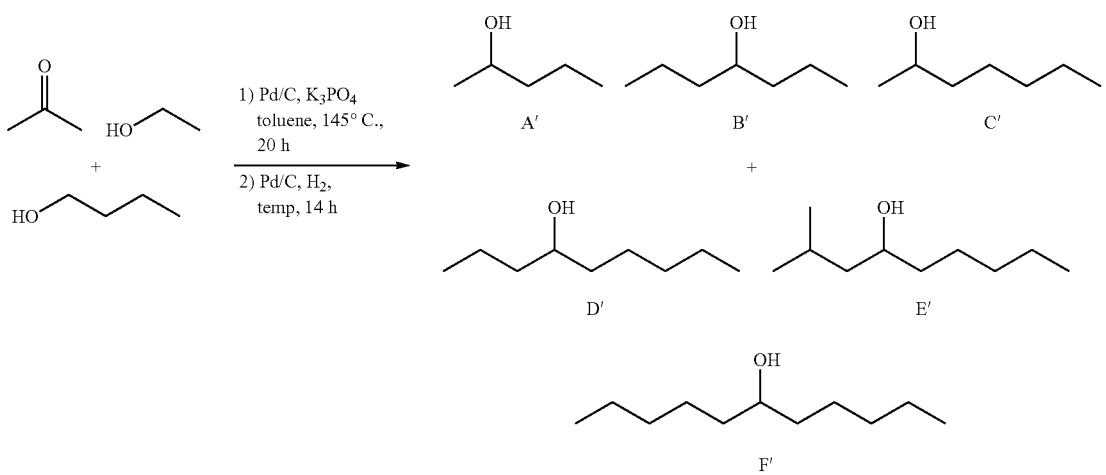

5% palladium on carbon (0.01 mmol), K$_3$PO$_4$ (mol % varied according to the amounts in Table 9), and a magnetic stir bar were added to a high-pressure reaction vessel (HEL parallel synthesizer). To each vessel, 1.5 mL of toluene was added. Then, acetone (2.3 mmol), ethanol (1 mmol), and butanol (3.7 mmol) were also added to each vessel. Each vessel was sealed, and kept at 145° C. in a pre-heated metal block. Each reaction mixture was stirred at 145° C. over 20 hours.

Figure 9:
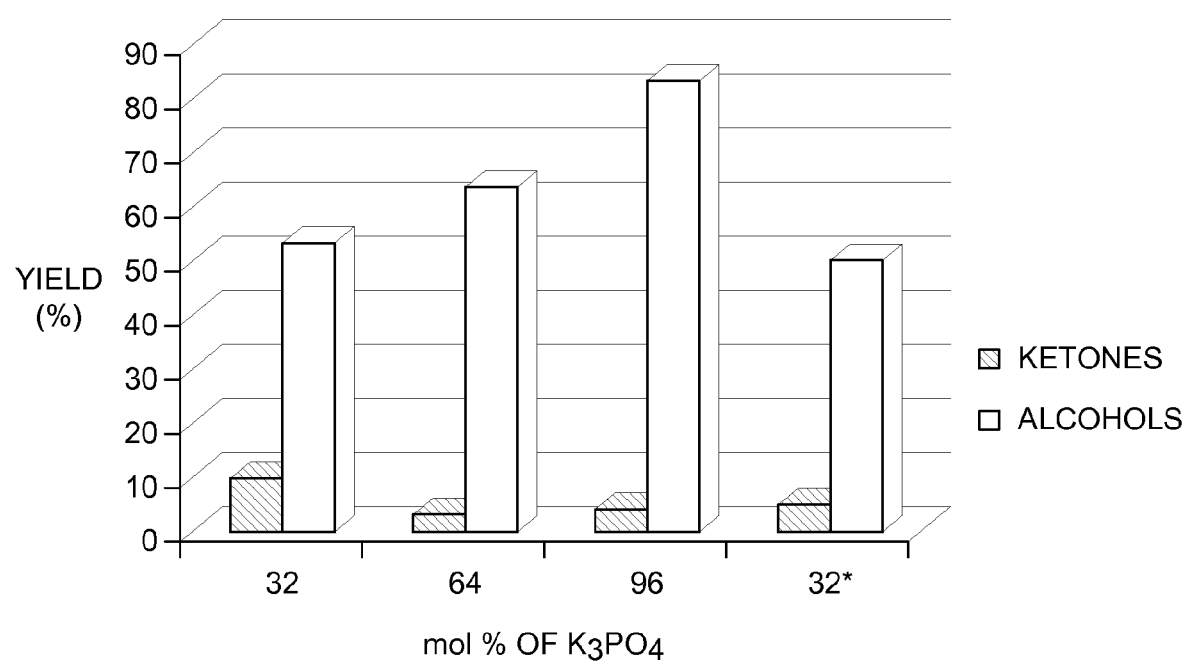
FIG. 9 is a graph depicting the yield of ketones and alcohols from varying the amount of base (mol % of $K_3PO_4$)

To this reaction mixture, 5% platinum on carbon (0.02 mmol) was added, and the reaction vessel was pressurized with H$_2$ gas (pressure as shown in Table 9). Each reaction mixture was stirred at one of the temperatures listed in Table 9 below for 14 hours, and then cooled to room temperature. Note that reactions 4, 8, and 12 were performed neat. GC analysis of each final reaction mixture yielded the ratio of ketones and A'-F' products in Table 9. FIG. 9 also depicts effect of varying the concentration of base used on the yield of ketones and alcohols.

5% palladium on carbon (0.01 mmol), K$_3$PO$_4$ (4.5 mmol), and a magnetic stir bar are added to two 12-mL Q-Tubes (pressure tubes). To both tubes, acetone (2.3 mmol), ethanol (1 mmol), and butanol (3.7 mmol) are added. Each tube is sealed, and kept at 145° C. in a pre-heated metal block. Each reaction mixture is stirred at 145° C. over 20 hours.

Next the reaction mixture from each tube is filtered, and the liquid products collected. The first ketone-containing reaction mixture is added to a reactor containing sulfided NiO—MoO$_3$/Al$_2$O$_3$. The reactor is pressurized to 40 bar with hydrogen gas and heated to 250° C. After 10 hours the reactor is cooled to room temperature and the products analyzed by GC for yields of A"-F" products. The second ketone-containing reaction mixture is passed over Pt/SiO$_2$—Al$_2$O$_3$ in a plug-flow bed reactor at 200° C. with a hydrogen pressure of 30 bar. GC analysis of the reactor effluent reveals the yield of A"-F" products.

TABLE 9

Alcohol product distribution from ketones produced from alkylation of acetone in ABE mix

| Entry | Base (mmol) | Temp (° C.) | H$_2$ (psi) | Total Ketone Yield (%) | Molar Yield of Alcohols (%) | | | | | | |
|---|---|---|---|---|---|---|---|---|---|---|---|
| | | | | | A' | B' | C' | D' | E' | F' | Total |
| 1 | 1.5 | RT | 90 | 20.2 | 6.3 | 0 | 19 | 0.6 | 0.01 | 0.8 | 46.91 |
| 2 | 3.0 | RT | 90 | 25.67 | 6.1 | 0.7 | 20.9 | 4 | 0.05 | 5.8 | 63.22 |
| 3 | 4.5 | RT | 90 | 19.83 | 3.9 | 0 | 12.8 | 10.8 | 0.3 | 17.3 | 64.93 |
| 4[a] | 1.5 | RT | 90 | 61.2 | 4.4 | 0.9 | 13.3 | 5.6 | 0.1 | 8.9 | 94.4 |
| 5 | 1.5 | 110 | 150 | 9.4 | 10.3 | 0.8 | 42.9 | 6.5 | 0.1 | 10.7 | 80.7 |
| 6 | 3.0 | 110 | 150 | 13.5 | 5.6 | 1.1 | 20.1 | 10 | 0.2 | 21.5 | 72 |
| 7 | 4.5 | 110 | 150 | 2.72 | 3.5 | 1.8 | 12.6 | 16.2 | 2.1 | 34.1 | 73.02 |
| 8[a] | 1.5 | 110 | 150 | 4.3 | 3.3 | 1.3 | 9.7 | 10.3 | 3.6 | 20.2 | 52.7 |
| 9 | 1.5 | 110 | 150 | 7.5 | 6.1 | 0.5 | 26.0 | 3.9 | 0.1 | 6.3 | 50.3 |
| 10 | 3.0 | 110 | 150 | 3.2 | 6.7 | 1.1 | 21.9 | 9.8 | 1.0 | 23.3 | 66.9 |
| 11 | 4.5 | 110 | 150 | 4.3 | 5.3 | 0.0 | 15.5 | 18.9 | 3.2 | 40.3 | 87.4 |
| 12[a] | 1.5 | 110 | 150 | 4.9 | 3.8 | 1.2 | 10.8 | 9.9 | 3.9 | 20.6 | 55.0 |

[a]Neat reaction.
RT = room temperature

Example 11

One-Pot Alkylation of ABE-Mix and Reduction of Ketones to Produce Corresponding Alkanes

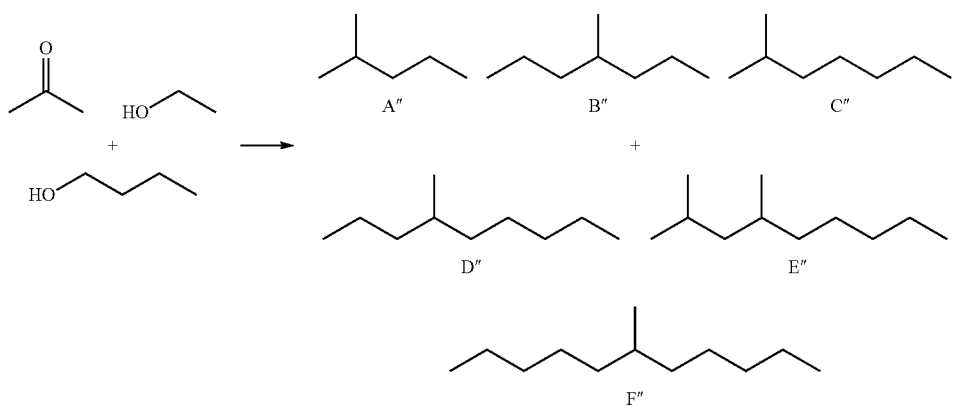

Example 12

Recycling of Catalysts in the Conversion of ABE Mixture into Ketones

5% palladium on carbon, $K_3PO_4$ (96 mol %), and a magnetic stir bar were added to a 12-mL Q-Tube (pressure tube). To the tube, 3 mL of toluene was added. Then, acetone (4.6 mmol), ethanol (2 mmol), and butanol (7.4 mmol) were also added to the tube. The tube was sealed, and kept at 145° C.

At 10, 20, and 30 hours, 100 mol % excess of the ABE mixture was added to the tube. Samples were taken at 10, 20, and 30 hours. Each sample was cooled to room temperature. To each sample, dodecane (internal standard) was added and diluted with ethyl acetate. GC analysis was performed on each reaction sample. Overall yields were determined at 10, 20, and 30 hours. The overall yield based on the total acetone feed for each time point was: 80% at 10 hours, 72% at 20 hours, and 61% at 30 hours. This demonstrated that the metal and base catalysts remained active, and continued to convert each new aliquot of starting material.

Figure 10:
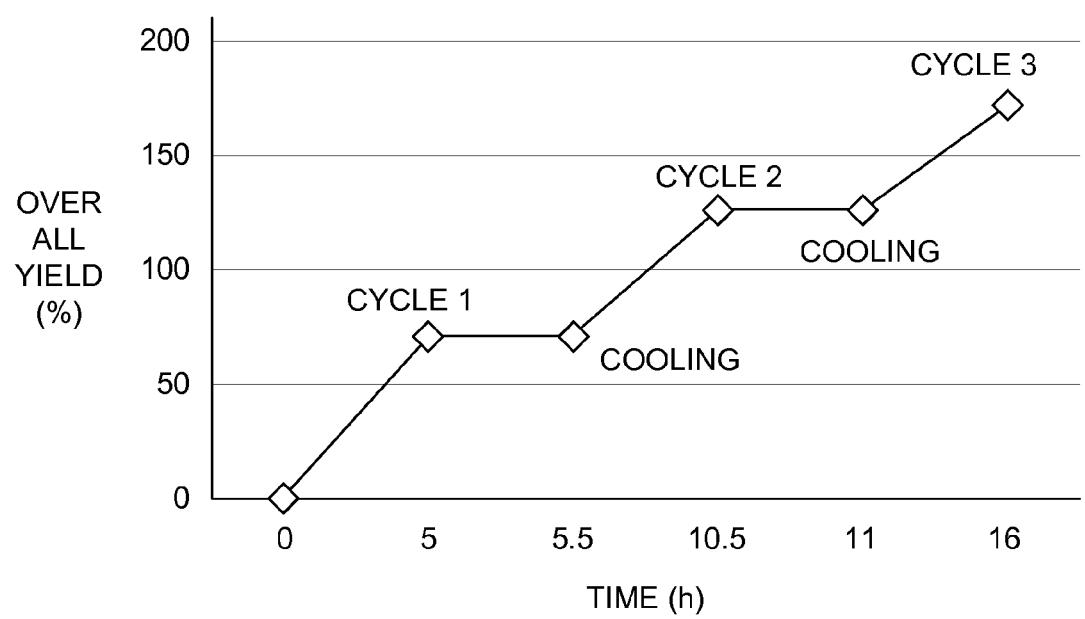
FIG. 10 is a graph depicting the yield of ketones (A-F products) from the recycling of the catalyst (Pd/C) through three cycles.

The procedures described in this Example were repeated by adding excess ABE mixture at 5 and 10.5 hours. Overall yields were determined based on each time point, and the results are depicted in FIG. 10.

Example 13

Palladium-Catalyzed Guerbet Reaction of Butanol

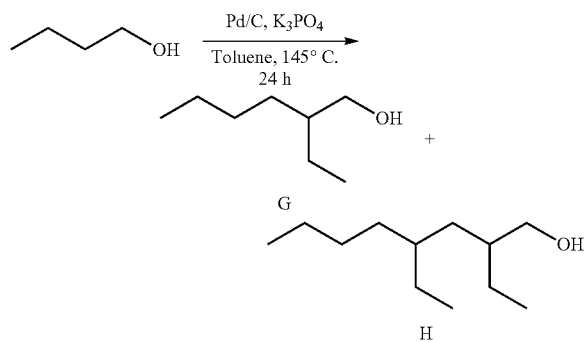

5% palladium on carbon (x mmol), K3PO4 (y mol %) and a magnetic stir bar were added to a 12-mL Q-Tube (pressure tube). To each tube, 1.5 mL of toluene and butanol (5 mmol) was added, and stirred at 145° C. for 24 hours. Each sample was cooled to room temperature. GC analysis was performed with internal standard (dodecane) on each reaction sample to determine product yields. The yields provided in Table 10 below correspond to product G, i.e., the 2-ethyl-1-hexanol.

TABLE 10

Palladium-catalyzed Guerbet reaction of butanol

| Reaction | Pd/C (x mol %) | $K_3PO_4$ (y mol %) | Conversion | Yield |
|---|---|---|---|---|
| 1 | 0.2 | 60 | 71.2 | 53.9 |
| 2 | 0.2 | 90 | 79.5 | 60.6 |
| 3 | 0.2 | 120 | 79.6 | 58.9 |
| 4 | 0.3 | 60 | 50.2 | 34.2 |
| 5 | 0.2 | 60 | 71.2 | 53.9 |

TABLE 10-continued

Palladium-catalyzed Guerbet reaction of butanol

| Reaction | Pd/C (x mol %) | $K_3PO_4$ (y mol %) | Conversion | Yield |
|---|---|---|---|---|
| 6 | 0.1 | 60 | 84.8 | 65.4 |
| 7 | 0.05 | 60 | 92.4 | 64.2 |
| 8 | 0.025 | 60 | 92 | 64.6 |
| 9 | 0.0125 | 60 | 81.2 | 60.7 |

Example 14

Extraction Using Glyceryl Tributyrate

Simulated clostridia fermentation media was prepared with the following components: glucose (20 g/L), yeast extract (5 g/L), ammonium acetate (2 g/L), butyric acid (2 g/L), acetoin (3 g/L), ethanol (20 g/L), acetone (20 g/L), 1-butanol (20 g/L), and lactic acid (10 g/L). 5 mL of simulated fermentation media was combined with 5 mL of glyceryl tributyrate, and mixed for 5 minutes by inversion. The mixtures were then spun down at 5300 rpms for 5 minutes, and the extractant phase removed for GC analysis. Distribution coefficients were calculated based on the following equation:

$$K_{Di} = \frac{\text{Kg of } compound_i \text{ in the extractant phase}}{\text{Kg of } compound_i \text{ in the aqueous phase}}$$

ABE extraction experiments were run in quadruplicate. *Miscanthus giganteus*, obtained from the University of Illinois, Urbana-Champaign, was first ground and placed through a 4 mm size sieve. 5% w/w of *Miscanthus giganteus* was mixed with 1% $H_2SO_4$ in sealed Teflon tubes and reacted under the following conditions: 30 minutes at 30° C., 6 minute ramp to 180° C., 2 minutes at 180° C. The liquid hydrolysate was pH adjusted to 5.0 using concentrated KOH. 3 mL of hydrolysate was combined with 3 mL of glyceryl tributyrate and thoroughly mixed for 5 minutes by inversion. The mixtures were then centrifuged for 5 minutes at 5300 rpms, and the aqueous phase was removed Inhibitors remaining in the aqueous phase were measured by first extracting into ethyl acetate, followed by drying with $Na_2SO_4$. The dried solution was then incubated with bis (trimethylsilyl)trifluoracetamide at 70° C. for 30 minutes. Inhibitor concentrations were analyzed by GC/MS with isopropylphenol as an internal standard.

Glyceryl tributyrate recovered both acetone ($K_D$=1.1) and 1-butanol ($K_D$=2.6) from aqueous solution. Ethanol, however, was observed to remain in the aqueous phase ($K_D$=0.2). Additionally, glyceryl tributyrate removed several of the inhibitors of biofuel fermentation found in acid-pretreated lignocellulosic biomass (as summarized in Table 11 below).

TABLE 11

Extraction of inhibitors generated by acid pretreatment of lignocellulosic biomass

| Compound Name | Initial Conc. (mg/L) | $K_D$ (extractant/water) |
|---|---|---|
| 4-hydroxybenzaldehyde | 15.8 | 4.9 |
| vanillin | 30.8 | 7.6 |

TABLE 11-continued

Extraction of inhibitors generated by acid pretreatment of lignocellulosic biomass

| Compound Name | Initial Conc. (mg/L) | $K_D$ (extractant/water) |
|---|---|---|
| syringaldehyde | 18.9 | 5.3 |
| vanillic acid | 14.5 | 1.3 |
| p-coumaric acid | 35.5 | 3.8 |
| ferulic acid | 41.8 | 4.2 |
| furural | 1926.1 | 6.5 |
| hydroxymethyl furfural | 205.1 | 0.5 |

Thus, use of glyceryl tributyrate allows for simultaneous removal of residual inhibitors and the desired product (e.g., acetone and butanol) during biofuel fermentation, a key advantage over existing recovery technologies.

Example 15

Toxicity Studies on *Clostridium acetobutylicum*

Growth inhibition and cell viability was examined in a study using up to 1:1 volume ratios of extractant to media. This study showed that glyceryl tributyrate was non-toxic to *Clostridium acetobutylicum*.

Example 16

Effect of Glyceryl Tributyrate on Glucose Fermentation

Figure 13:
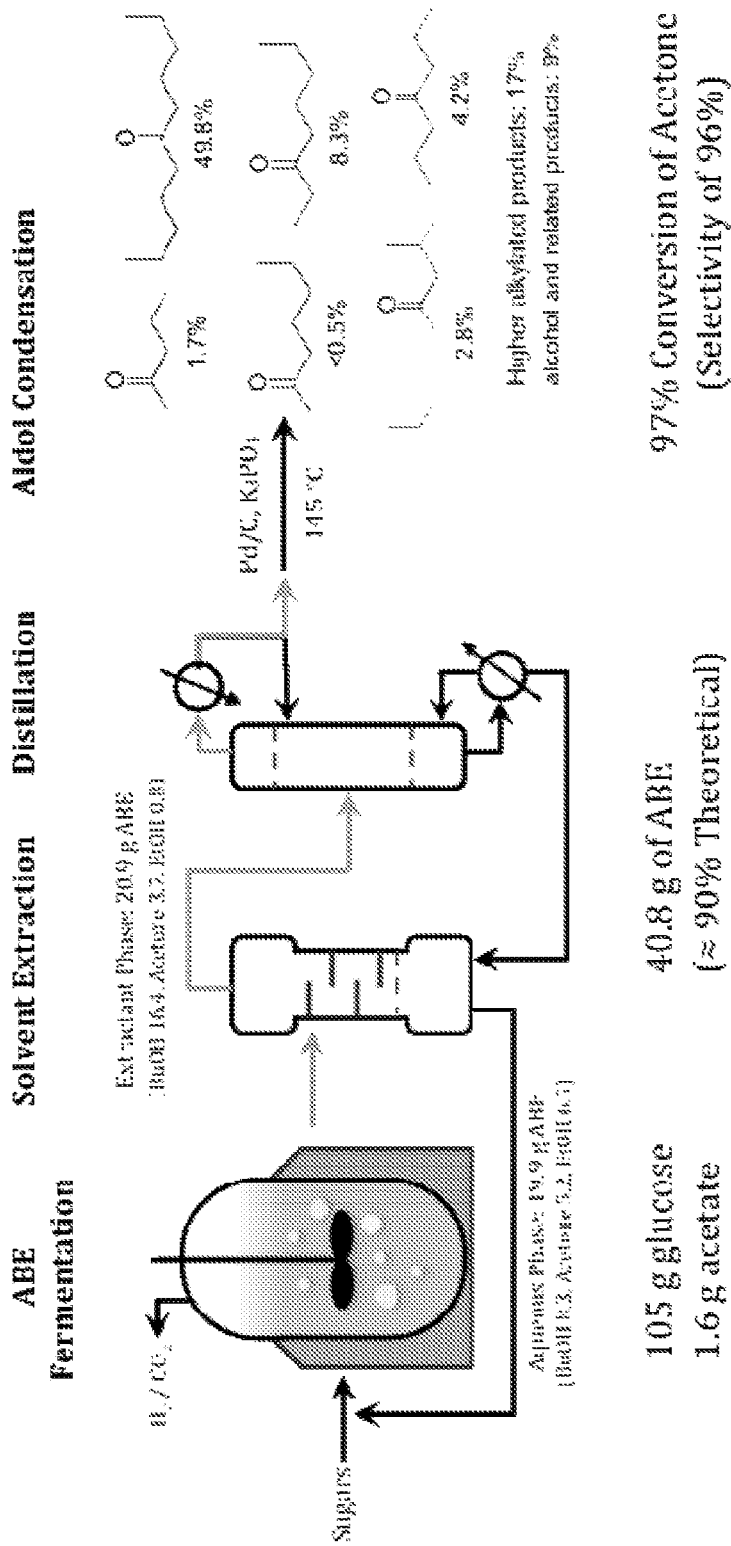
FIG. 13 is a process flow diagram for an exemplary process to convert the product mixture from an ABE fermentation to C5-C11 ketones.

A 60-hour 2 L-fermentation of *Clostridium acetobutylicum* on glucose with a 1:1 volume ratio of medium and glyceryl tributyrate was performed, and observed to produce 40.8 grams of solvents with 16.4 g of 1-butanol, 3.7 g of acetone, and 0.8 g of ethanol, respectively partitioning into the extractant phase. With reference to FIG. 13, these solvents were produced from 105 g of glucose and 1.6 g of acetate, achieving an overall ABE weight yield of 90% the theoretical maximum.

In a separate reactor, 5% palladium on carbon, $K_3PO_4$ (954 mg, 4.5 mmol), and a magnetic stir bar were added to a 12-mL Q-Tube (pressure tube). To the tube, 1.5 mL of toluene was added. Then, the acetone, ethanol and butanol prepared from fermentation described above were also added to the reactor. The reaction mixture was stirred for 20 hours at 145° C., and then cooled to room temperature. The reaction mixture was diluted with tetrahydrofuran and the GC analysis of the reaction mixture was carried out.

FIG. 13 illustrates the yields of the products from the reaction. The overall molar yield based on acetone was 93%, which represented a 97% conversion. In particular, 17% of higher alkylated products were observed, and 0% of alcohol and related products were observed, as determined using FID response factor. The products yields are further summarized in Table 12 below. Total Mass values (g) were based on fermentative production and recovery of 153.5 mmol acetone, 333.8 mmol butanol and 158.7 mmol ethanol. Assuming complete recovery of acetone, butanol and ethanol from both phases, 20 g of C7 and higher products were produced. 15 g of lower molecular weight products were also produced.

TABLE 12

Summary of amount of alkylated products (C7+) produced

| Alkylated Products C7+ | Reaction Mass (mg) | Total Mass (g) |
|---|---|---|
| 4-Heptanone | 2.8 | 0.2 |
| 2-Heptanone | 7.6 | 0.7 |
| 4-Nonanone | 48.5 | 4.2 |
| 2-Methyl-4-nonanone | 0.8 | 0.1 |
| 6-Undecanone | 89.9 | 7.7 |
| Higher MW products | 22.2 | 1.9 |
| Alcohols and other products | 61.7 | 5.3 |
| Overall | 233.5 | 20.0 |

Figure 18:
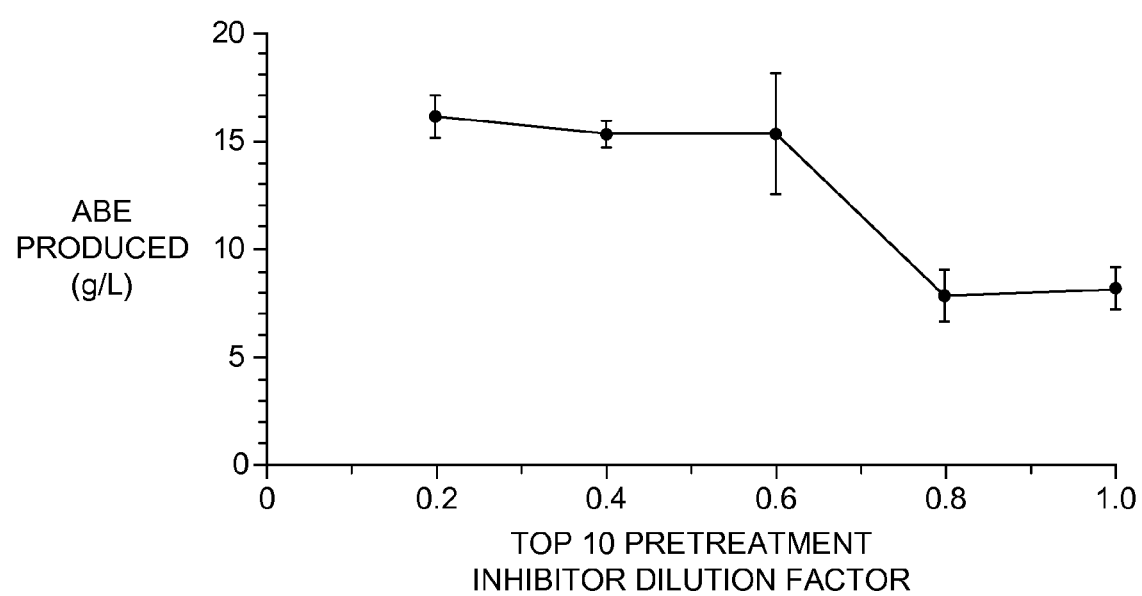
FIG. 18 is a graph showing the effect of inhibitors on ABE fermentation without extractant based on the amount of acetone, butanol and ethanol produced.

In contrast, FIG. 18 illustrates the effect of inhibitors on ABE fermentation without extractant.

Example 17

Fed-Batch Extractive Fermentation of Glucose Using Glyceryl Tributyrate

*Clostridium acetobutylicum* ATCC824 was grown in clostridial growth medium (CGM) as previously described in Example 14 above. Fed-batch fermentations were conducted in 3-L bioreactors (Bioengineering AG, Switzerland) with a 2 L working volume. Additional glucose and yeast extract were added intermittently to the culture using a concentrated solution of 450 g/L and 50 g/L, respectively. Cultures were grown at 37° C. anaerobically by sparging 100 mL/min of $N_2$ gas until solvent production was initiated. The culture pH was adjusted to 5.5 prior to inoculation. After inoculation the bioreactor pH was controlled at pH of at least 4.8.

Sugars and major metabolites (glucose, sucrose, lactate, acetate, butyrate, acetoin, ethanol, acetone, and 1-butanol) were measured in the aqueous phase using an Agilent (Santa Clara, Calif.) HPLC system equipped with refractive index and UV/Vis detectors. A Bio-Rad (Hercules, Calif.) Aminex HPX-87H ion exchange column with a Cation H guard column at 30° C. was used with a mobile phase of 0.05 mM sulfuric acid flowing at 0.7 mL min$^{-1}$. Acetone, 1-butanol and ethanol concentrations in the extractant phase were measured by GC/FID.

Figure 14:
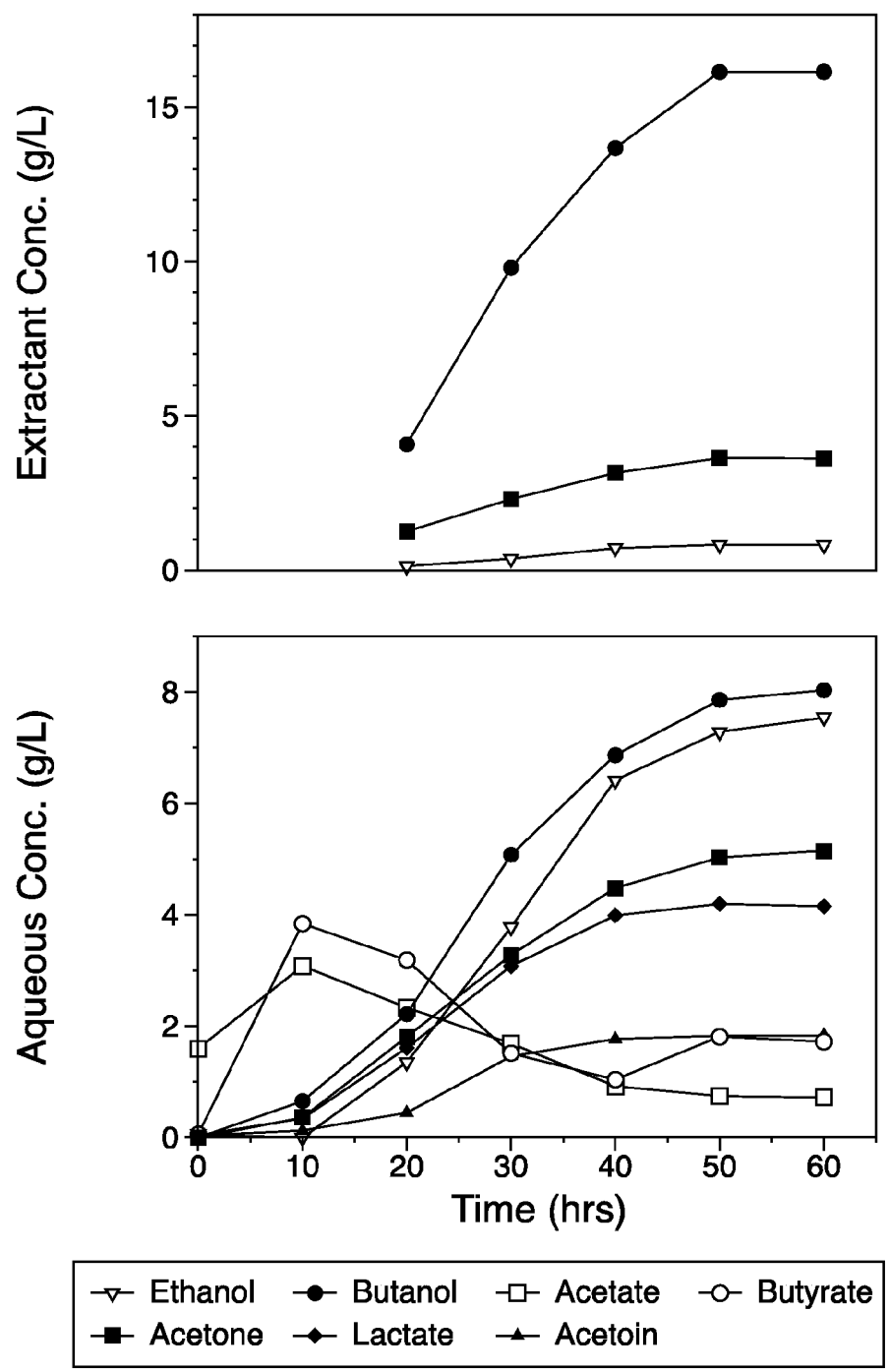
FIG. 14 depicts the time course of product formation in an exemplary fed-batch extraction fermentation of glucose with glyceryl tributyrate, in which the top graph shows the product formation in the extractant phase and the bottom graph shows the production formation in the aqueous phase.

FIG. 14 depicts product formation in fed-batch extractive fermentation of glucose with glyceryl tributyrate over 60 hours. With reference to FIG. 14, glyceryl tributyrate was observed to primarily extract butanol and acetone from the aqueous phase into the extractant phase.

Example 18

Fed-Batch Extractive Fermentation of Sucrose Using Glyceryl Tributyrate

The fed-batch extractive fermentation procedure described in Example 17 above was performed using sucrose instead of glucose as the primary carbon source. The initial sucrose concentration was 60 g/L. Specifically, extractive fermentation with sucrose was carried out in 100-mL shake flasks with 25 mL of clostridia growth media inoculated with 2 mLs of $OD_{600}$ (0.6-1.0) cells. Cultures were grown at 37° C. in an anaerobic chamber and pH adjusted to 4.8 using 1M KOH during the first 12 hours of growth. After 16 hours, 25 mL of glyceryl tributyrate was added to the culture.

Figure 15:
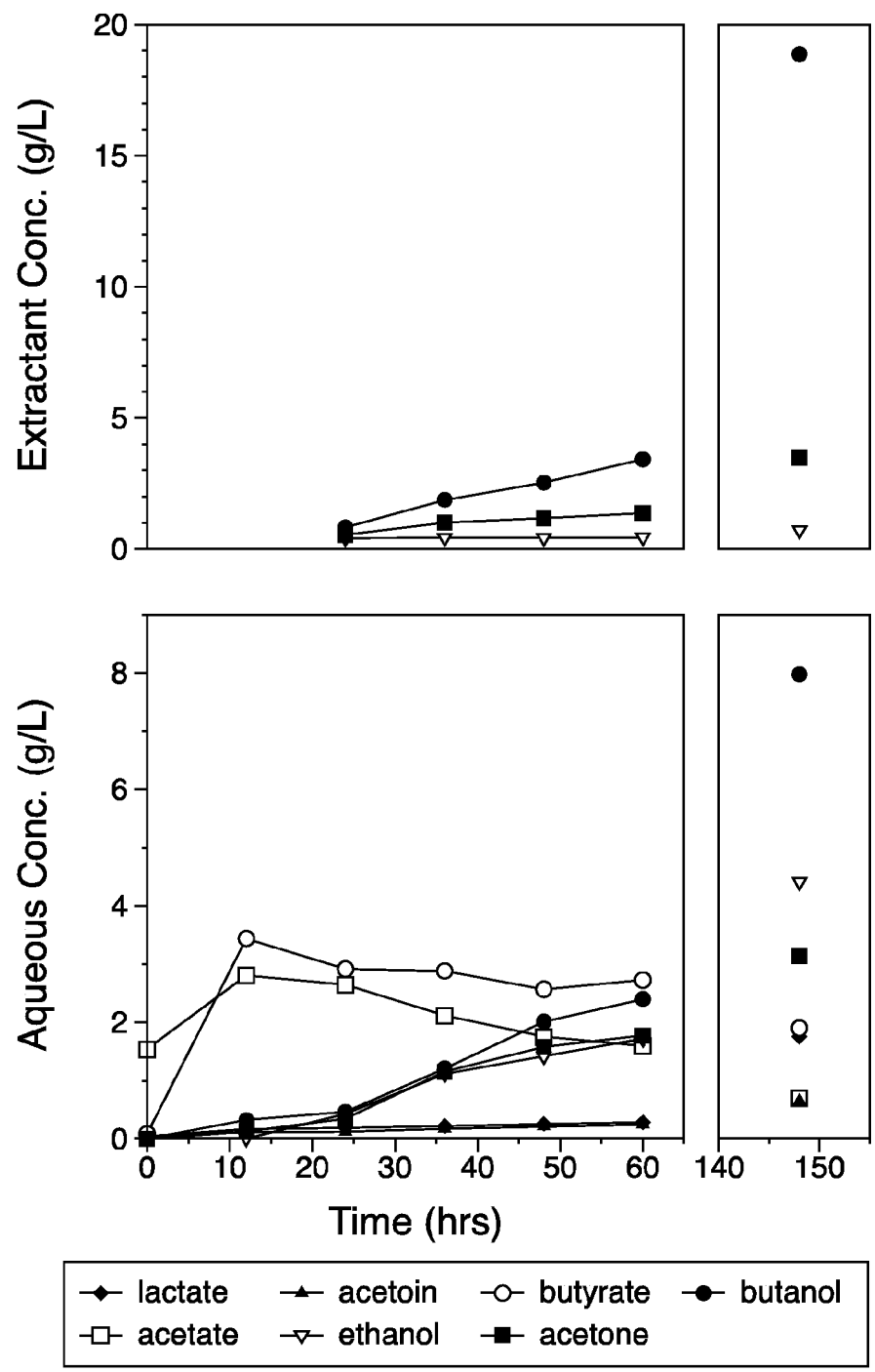
FIG. 15 depicts the time course of product formation in an exemplary fed-batch extraction fermentation of sucrose with glyceryl tributyrate, in which the top graph shows the product formation in the extractant phase and the bottom graph shows the production formation in the aqueous phase.

FIG. 15 depicts product formation in fed-batch extractive fermentation of sucrose with glyceryl tributyrate over 60 hours. With reference to FIG. 15, glyceryl tributyrate was observed to primarily extract butanol and acetone from the aqueous phase into the extractant phase.

Example 19

Effect of Water on Alkylation Reaction of ABE Mixture

Figure 16:
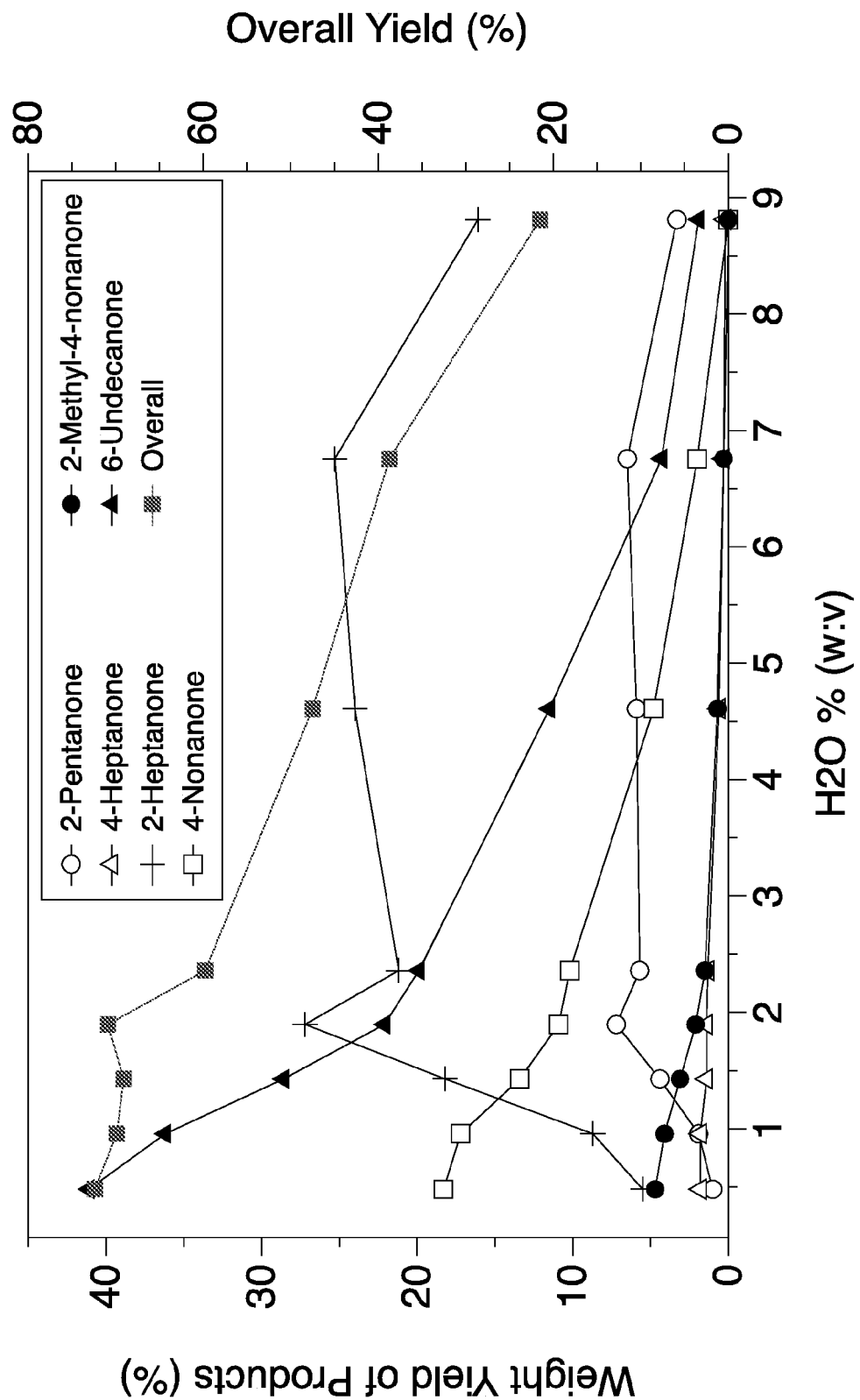
FIG. 16 is a graph depicting the effect of water addition on alkylation reactions of an ABE-mixture.

5% palladium on carbon (containing 50% of water, 42 mg, 0.01 mmol), potassium phosphate tribasic (954 mg, 4.5 mmol), and a magnetic stir bar were added to a 12-mL Q-Tube (pressure tube). To the tube, 1.5 mL of toluene was added. Then, acetone (0.17 mL, 2.3 mmol), ethanol (60 μL, 1 mmol), and butanol (0.34 mL, 3.7 mmol) were also added to the tube. Water was also added to each tube in the amount (w:v %) depicted in FIG. 16. Each tube was sealed, and kept at 145° C. in a pre-heated metal block. The reaction mixture was stirred for 20 hours at 145° C., and then cooled to room temperature. Subsequently, dodecane (internal standard) was added and diluted with ethyl acetate. GC analysis of each reaction mixture yielded the amount of products as depicted in FIG. 16. Yields were determined based on acetone.

As seen in FIG. 16, the presence of water was observed to decrease the overall reaction rate, resulting in less double alkylation and lower overall yields.

Example 20

Alkylation Reaction of ABE Mixture in Neat Conditions

5% palladium on carbon (containing 50% of water, mmol varied according to amounts in Table 13), $K_3PO_4$ (mmol varied according to amounts in Table 13), and a magnetic stir bar were added to a 12-mL Q-Tube (pressure tube). To each tube, acetone (4.6 mmol), ethanol (2 mmol), and butanol (7.4 mmol) were added. Each tube was sealed, and kept in a pre-heated metal block at one of the temperatures listed in Table 13 below. Each reaction mixture was stirred for 20 hours at that temperature, and then cooled to room temperature. Subsequently, dodecane (internal standard) was added and diluted with ethyl acetate. GC analysis of each reaction mixture yielded the ratio of $C_5$-$C_{11}$ and $C_{11}$+ products in Table 13 below. Yields were determined based on acetone.

TABLE 13

Alkylation reaction products in neat conditions

| Pd/C (X mol %) | Base (Y mol %) | Temp (° C.) | Yield (%)[a] $C_5$-$C_{11}$ | $C_{11}$+ | Total | TON[b] | Solvent |
|---|---|---|---|---|---|---|---|
| 0.025 | 32 | 145 | 27 | 15 | 42 | 1574 | Neat |
|  |  | 180 | 36 | 19 | 55 | 2072 |  |
| 0.0125 | 32 | 145 | 22 | 19 | 41 | 3074 |  |
|  |  | 180 | 26 | 17 | 43 | 3220 |  |
| 0.0125 | 16 | 145 | 17 | 11 | 28 | 2080 |  |
|  |  | 180 | 31 | 14 | 45 | 3386 |  |

[a]GC weight yield
[b]Turn Over Number (TON) based on alcohols

Example 21

Time Course Product Distribution

5% palladium on carbon (containing 50% of water, 0.02 mmol), $K_3PO_4$ (9 mmol), and a magnetic stir bar were added to a 12-mL Q-Tube (pressure tube). To the tube, toluene (3 mL), acetone (4.6 mmol), ethanol (2 mmol), and butanol (7.4 mmol) were added. The tube was sealed, and kept in a pre-heated metal block at 145° C. The reaction mixture was stirred for up to 1200 minutes, and then cooled to room temperature. Subsequently, dodecane (internal standard) was added and diluted with ethyl acetate. GC analysis was performed on the reaction mixture to determine yields of the products. Yields were determined based on acetone. FIG. 17A shows the product distribution over time.

As seen in FIG. 17A, monoalkylation of acetone with butanol and ethanol was observed to occur within the first 1-1.5 hours of the reaction to produce 2-pentanone and 2-heptanone. These species were then observed to undergo further reaction to form double alkylated products. Surprisingly, no aldehydes were observed during the reaction, suggesting that the aldehyde intermediates were present in very low concentrations and reacted rapidly with acetone and other ketones. Hence, the formation of Guerbet products was observed to be minimized, and acetone alkylation was observed to predominate.

Example 22

Double Alkylation Reactions to Yield C11-C19 Products

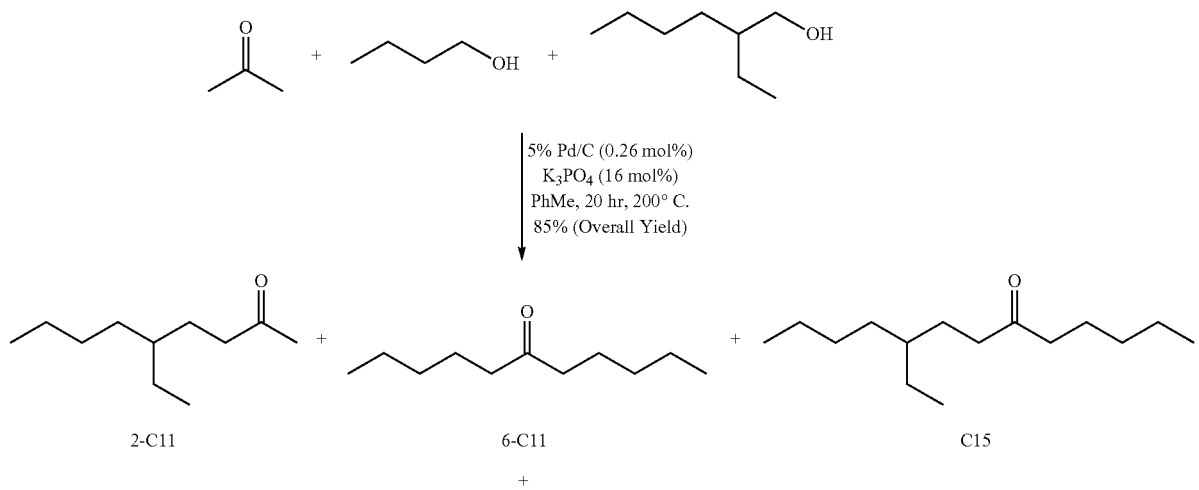

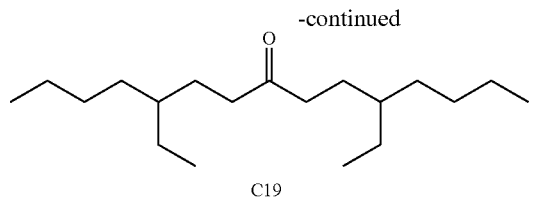

C19

In a 12 mL Q-tube, 5 wt. % palladium on carbon (0.011 g, 0.0026 mmol, water ca. 50%), potassium phosphate tribasic (0.034 g, 0.16 mmol) and a magnetic stir bar were placed. To the reaction mixture, acetone (0.058 g, 1 mmol), 2-ethyl-1-hexanol (1.30 g, 10 mmol), butanol (0.22 g, 3 mmol) and 1 mL toluene were sequentially added. The Q-tube was sealed and the reaction mixture was stirred for 20 hours at 200° C. in a pre-heated metal block. The reaction mixture was cooled to room temperature and dodecane (internal standard) was added. The reaction mixture was diluted with tetrahydrofuran and the GC analysis of the reaction mixture was carried out (85% overall yield, 2-C11: 4%, 6-C11: 22%, C15: 37%, C19: 22%). Thus, this Example showed the selective production of the Guerbet product (2-ethyl-hexanol) in the presence of acetone.

Example 23

Double Alkylation Reactions to Yield C19 Product

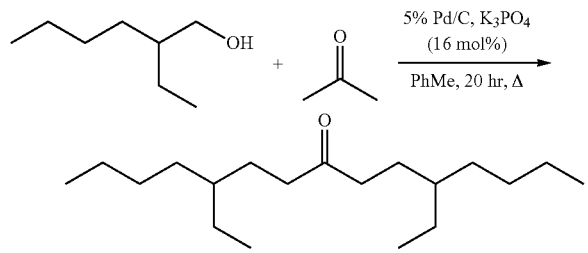

5% palladium on carbon (containing 50% of water, 0.05 mol %), potassium phosphate tribasic (0.16 mol %) and magnetic stir bar were added to a 12 mL Q-Tube (pressure tube). To the reaction mixture, acetone (0.058 g, 1 mmol), 2-ethyl-1-hexanol (0.326 g, 2.5 mmol), and toluene (1 mL) were sequentially added. The Q-tube was sealed and the reaction mixture was stirred for 20 hours at 200° C. in a pre-heated metal block. The reaction mixture was cooled to room temperature and dodecane (internal standard) was added. The reaction mixture was diluted with tetrahydrofuran and the GC analysis of the reaction mixture was carried out (72% overall yield).

Example 24

Variation of Alkylation Reaction Conditions of ABE Mixture to Control Molecular Weight of Products

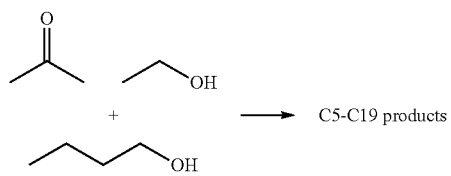

→ C5-C19 products

Alkylation of an ABE mixture was performed under different reaction conditions to control the production of higher molecular weight compounds. In particular, the ratio of ABE, the amount of base, and temperature were varied. Distillation of the ABE mixture with an extractant was also performed in one of the reactions described below.

In the first reaction, 5% palladium on carbon (containing 50% of water, 1 mol %), K₃PO₄ (0.95 equiv), and a magnetic stir bar were added to a 12-mL Q-Tube (pressure tube). To each tube, acetone (2.3 mmol), ethanol (1 mmol), and butanol (3.7 mmol) were added. The tube was sealed, and kept in a pre-heated metal block at a temperature between 190° C. and 210° C. The reaction mixture was stirred for 20 hours, and then cooled to room temperature. Subsequently, dodecane (internal standard) was added and diluted with ethyl acetate. GC analysis was performed on the reaction mixture. Overall yield (57%; C5-C11: 57%; C15: trace amount).

In the second reaction, 5% palladium on carbon (containing 50% of water, 1 mol %), K₃PO₄ (1.3 equiv), and a magnetic stir bar were added to a 12-mL Q-Tube (pressure tube). To the reaction tube, acetone (1.6 mmol), ethanol (1.7 mmol), and butanol (3.7 mmol) were added. The tube was sealed, and kept in a pre-heated metal block at a temperature of about 145° C. The reaction mixture was stirred for 20 hours, and then cooled to room temperature. Subsequently, dodecane (internal standard) was added and diluted with ethyl acetate. GC analysis was performed on the reaction mixture. Overall yield (78%; C5-C11: 72%; C13 (5-ethyl-undecan-b-one): 4%, C15: 2%).

In the third reaction, 5% palladium on carbon (containing 50% of water, 1 mol %), K₃PO₄ (0.95 equiv), and a magnetic stir bar were added to a 12-mL Q-Tube (pressure tube). To each tube, acetone (2.3 mmol), ethanol (1 mmol), and butanol (3.7 mmol) were added. The tube was sealed, and kept in a pre-heated metal block at a temperature of about 145° C. The reaction mixture was stirred for 20 hours, and then cooled to room temperature. Subsequently, dodecane (internal standard) was added and diluted with ethyl acetate. GC analysis was performed on the reaction mixture. Overall yield (79%; C5-C11: 77%; C13: 2%).

In the fourth reaction, the reaction conditions of the third reaction described above were repeated, except that the ABE mixture was first distilled with an extractant (tributyrin). Distillation with the extractant yielded an ABE mixture that mainly included acetone and butanol, which was used in the alkylation reaction. Overall yield (93%; C5-C11: 67.3%, higher alkylated products: 17%, alcohol and related products: 9%).

All yields described above were determined based on acetone.

Example 25

Ir-Catalyzed ABE Condensation Reaction

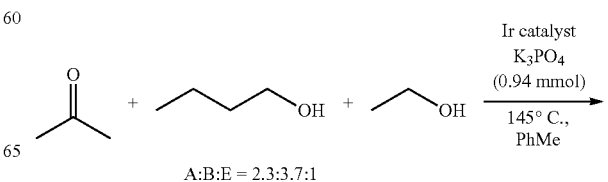

A:B:E = 2.3:3.7:1

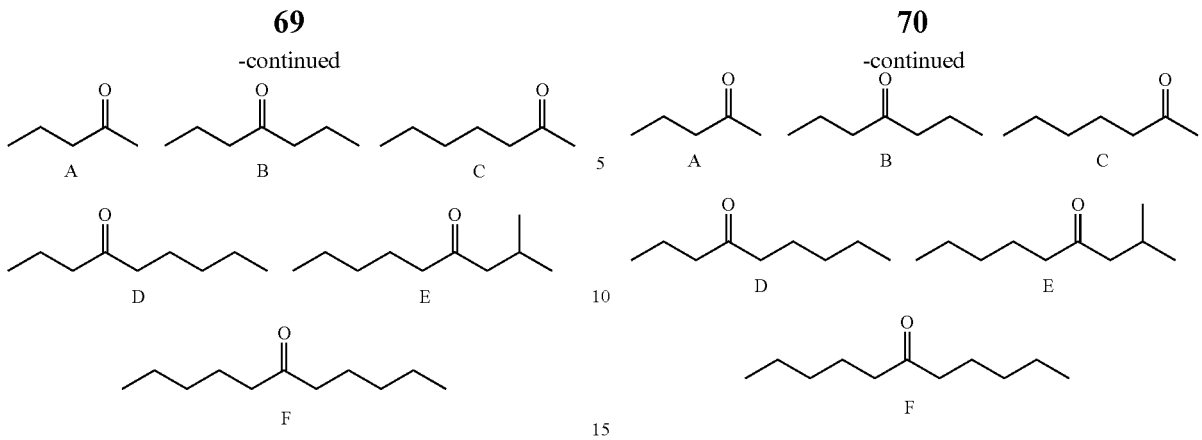

An iridium catalyst (x mol %) listed in Table 14 below, $K_3PO_4$ (0.94 mmol) and a magnetic stir bar were added to a 12-mL Q-Tube (pressure tube). To each tube, 1.5 mL of toluene and acetone (2.3 mmol), ethanol (1 mmol), and butanol (3.7 mmol) were added. Each tube was sealed, and kept in a pre-heated metal block at a temperature of about 145° C. The reaction mixture was stirred for 20 hours, and then cooled to room temperature. GC analysis was performed with internal standard (dodecane) on each reaction sample to determine yields of A-F products as shown in the reaction scheme above. Yields were determined based on acetone.

TABLE 14

Variation of type and amount of Iridium catalyst

| Entry | Ir Catalyst (mol %) | A | B | C | D | E | F | Total |
|---|---|---|---|---|---|---|---|---|
| 1 | [Cp*IrCl₂]₂ (0.5) | 0.7 | 10.8 | 3.5 | 5.0 | 0.9 | 19.8 | 41 |
| 2 | [Cp*IrCl₂]₂ (0.2) | 0.3 | 6.7 | 1.9 | 2.8 | 2.7 | 15.2 | 30 |
| 3 | [Cp*IrCl₂]₂ (0.08) | 0.2 | 7.4 | 1.4 | 2.2 | 3.1 | 11.5 | 26 |
| 4 | [Ir(COD)Cl]₂ (1.7) | 1.4 | 19.3 | 4.8 | 4.7 | 0.4 | 10.2 | 41 |

Example 26

Pd-Catalyzed ABE Reaction—Recycling Experiment Using Calcined Base

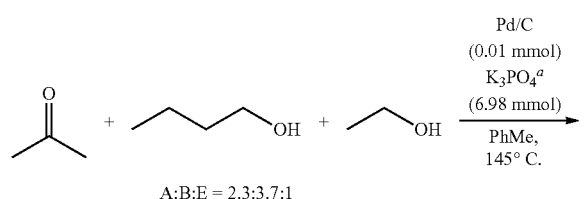

A:B:E = 2.3:3.7:1

The $K_3PO_4$ used in this Example was first calcined at 600° C. for 24 hours prior to use. 5% palladium on carbon (containing 50% of water, 0.01 mmol), $K_3PO_4$ (6.98 mmol), and a magnetic stir bar were added to a 12-mL Q-Tube (pressure tube). To each tube, acetone (2.3 mmol), ethanol (1 mmol), butanol (3.7 mmol), and toluene (2.5 ml) were added. Each tube was sealed, and kept in a pre-heated metal block at a temperature of about 145° C. The reaction mixture was stirred for 10 hours (i.e., Cycle 1 in Table 15 below). Additional acetone (2.3 mmol), ethanol (1 mmol), butanol (3.7 mmol) were added twice at 10 hour intervals to the reaction mixture (i.e., Cycles 2 and 3, respectively in Table 15 below) to show that the base-metal mixture can be recycled. GC analysis of samples taken at the end of each cycle was performed with internal standard (dodecane) on each reaction sample to determine yields of A-F products as shown in the reaction scheme above. Yields were determined based on acetone.

TABLE 15

Results from recycling of base-metal mixture

| Entry | A | B | C | D | E | F | Total |
|---|---|---|---|---|---|---|---|
| Cycle 1 | 0.8 | 3.7 | 6.5 | 23.2 | 1.5 | 63.7 | 99 |
| Cycle 2 | 0.4 | 3.2 | 21.6 | 15.1 | 0.7 | 32.0 | 73 |
| Cycle 3 | 0 | 0.9 | 28.6 | 6.4 | 0.2 | 15.8 | 52 |

What is claimed is:

1. A method of producing two or more compounds of Formula I,

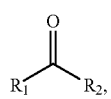

(Formula I)

wherein each $R_1$ and $R_2$ is independently an optionally substituted member selected from the group consisting of alkyl, cycloalkyl, heterocycloalkyl, aryl, heteroaryl, and arylalkyl, wherein the method comprises:
a) contacting biomass or sugars with a fermentation host to produce a fermentation product mixture, wherein the fermentation product mixture comprises acetone and two or more optionally substituted primary alcohols;

b) combining the fermentation product mixture with metal-based catalyst in the presence of base, wherein the metal-based catalyst comprises rhodium, palladium, iridium, or platinum, or a combination thereof; and c) producing two or more compounds of Formula I, wherein at least two of the two or more compounds of Formula I are double-alkylated.

2. The method of claim 1, wherein each $R_1$ and $R_2$ is independently an optionally substituted C1-C20 alkyl.

3. The method of claim 1, wherein the biomass or sugars and the fermentation host are further contacted with an extractant having one or more of the following properties:
  i) is non-toxic to *Clostridium*;
  ii) has partition coefficients for acetone and butanol equal to or greater than 1; and
  iii) has a partition coefficient for ethanol of less than 0.5.

4. The method of claim 3, wherein the extractant is glyceryl tributyrate, glyceryl tripropionate, oleyl alcohol, polypropylene glycol, or a combination thereof.

5. The method of claim 1, wherein the fermentation product mixture has less than 5 wt % water.

6. The method of claim 1, wherein the fermentation product mixture comprises acetone, butanol, and ethanol.

7. The method of claim 1, wherein the metal-based catalyst comprises palladium supported or tethered on a solid support.

8. The method of claim 1, wherein the metal-based catalyst comprises $Pd(OAc)_2$, $Pd_2(dba)_3$, $Pd(OH)_2/C$, Pd/C, $Pd/CaCO_3$, Pd/Alumina, or Pd-polyethylenimines on silica.

9. The method of claim 1, wherein the base is $K_3PO_4$, KOH, $Ba(OH)_2 \cdot 8H_2O$, $K_2CO_3$, KOAc, $KH_2PO_4$, $Na_2HPO_4$, pyridine, $Et_3N$, or a combination thereof.

10. The method of claim 1, wherein the two or more compounds of Formula I are produced at a temperature between 110° C. to 145° C.

11. The method of claim 1, wherein the two or more compounds of Formula I are produced at a temperature between 140° C. to 220° C.

12. The method of claim 1, wherein the yield of the two or more compounds of Formula I relative to the amount of acetone present in the fermentation product mixture is at least 10%.

13. The method of claim 1, wherein the yield of the double-alkylated compounds of Formula I relative to the amount of acetone present in the fermentation product mixture is at least 10%.

14. The method of claim 13, wherein the metal-based catalyst comprises $Pd(OAc)_2$, $Pd_2(dba)_3$, $Pd(OH)_2/C$, Pd/C, $Pd/CaCO_3$, Pd/Alumina, Pd-polytheylenimines on silica, $PtCl_2(COD)$, $[Rh(COD)Cl]_2$, or Pt/C.

* * * * *